(12) United States Patent
Biancucci et al.

(10) Patent No.: US 12,419,949 B2
(45) Date of Patent: Sep. 23, 2025

(54) MODIFIED HUMAN CYTOMEGALOVIRUS PROTEINS

(71) Applicant: GLAXOSMITHKLINE BIOLOGICALS SA, Rixensart (BE)

(72) Inventors: Marco Biancucci, Rockville, MD (US); Sumana Chandramouli, Rockville, MD (US); Newton Muchugu Wahome, Rockville, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 903 days.

(21) Appl. No.: 17/628,351

(22) PCT Filed: Jul. 22, 2020

(86) PCT No.: PCT/IB2020/056913
§ 371 (c)(1),
(2) Date: Jan. 19, 2022

(87) PCT Pub. No.: WO2021/014385
PCT Pub. Date: Jan. 28, 2021

(65) Prior Publication Data
US 2023/0201334 A1    Jun. 29, 2023

Related U.S. Application Data

(60) Provisional application No. 62/877,888, filed on Jul. 24, 2019.

(51) Int. Cl.
*A61K 39/245*    (2006.01)
*C07K 14/005*    (2006.01)

(52) U.S. Cl.
CPC .......... *A61K 39/245* (2013.01); *C07K 14/005* (2013.01)

(58) Field of Classification Search
CPC .............. A61K 39/245; A61K 2039/51; A61K 2039/572; A61K 2039/575; A61K 2039/627; A61K 39/12; C07K 14/005; C07K 2319/00; C07K 2319/20; C12N 2710/16122; C12N 2710/16134; A61P 31/20

See application file for complete search history.

(56) References Cited

U.S. PATENT DOCUMENTS

2018/0265551 A1 *    9/2018    Carfi ................... C07K 14/005

FOREIGN PATENT DOCUMENTS

WO    2012/049317 A2    4/2012
WO    WO-2018176103 A1 *    10/2018    .............. A61P 31/14

OTHER PUBLICATIONS

Sponholtz MR, Byrne PO, Lee AG, Ramamohan AR, Goldsmith JA, McCool RS, Zhou L, Johnson NV, et al. Structure-based design of a soluble human cytomegalovirus glycoprotein B antigen stabilized in a prefusion-like conformation. Proc Natl Acad Sci U S A. Sep. 10, 2024;121(37):e2404250121. Epub Sep. 4, 2024. (Year: 2024).*

Sharma S, Wisner TW, Johnson DC, Heldwein EE. HCMV gB shares structural and functional properties with gB proteins from other herpesviruses. Virology. Jan. 20, 2013;435(2):239-49. Epub Oct. 22, 2012. (Year: 2012).*

Gray VE, Hause RJ, Fowler DM. Analysis of Large-Scale Mutagenesis Data to Assess the Impact of Single Amino Acid Substitutions. Genetics. Sep. 2017;207(1):53-61. Epub Jul. 27, 2017. (Year: 2017).*

Backovic, et al., "Characterization of EBV gB indicates properties of both class I and class II viral fusion proteins", Virology, Elsevier, Amsterdam, NL, vol. 368, No. 1, Oct. 23, 2007 (Oct. 23, 2007), pp. 102-113.

Chandramouli, et al., "Structure of HCMV glycoprotein B in the postfusion conformation bound to a neutralizing human antibody", Nature Communications, vol. 6, No. 8176, Sep. 14, 2015 (Sep. 14, 2015), 12 pages.

Vitu, et al., "Extensive Mutagenesis of the HSV-1 gB Ectodomain Reveals Remarkable Stability of Its Postfusion Form", Journal of Molecular Biology, Academic Press, United Kingdom, vol. 425, No. 11, Mar. 13, 2013 (Mar. 13, 2013), pp. 2056-2071.

European Patent Office as Int'l. Searching Authority, International Search Report and Written Opinion in corresponding International Application No. PCT/IB2020/056913 mailed Oct. 27, 2020 (11 pages).

* cited by examiner

Primary Examiner — Rachel B Gill

(57) ABSTRACT

Modified HCMV gB proteins in a non-post-fusogenic conformation, compositions comprising such proteins, and uses thereof.

14 Claims, 12 Drawing Sheets
Specification includes a Sequence Listing.

FIG. 2A

```
                480        490        500        510        520        530        540
Merlin SEQ ID NO: 1    MLVLVAQLDQDTERGVLPRACHEAEAAVDQRRTLEVFKELSKINPSAILSAIYNRPIARIFK
AD169 SEQ ID NO: 6     MLVLVAQLDQDTERGVLPRACHEAEAAVDQDNTLEVFKELSKINPSAILSAIYNRPIARIFK 550        560        570        580        590
Merlin SEQ ID NO: 1    EPVLGIAESVTINQTSLVKLLRDVNVKESPGRCYSRPVVIFNFANSSYV
AD169 SEQ ID NO: 6     EMLGIAESVTINQTSLVNVLRDVNVKESPGRCYSRPVVIFNFANSSYV 600        610        620        630        640
Merlin SEQ ID NO: 1    QYGCEDNTLLGNHRTEECQLPSLKINIACNSAYEIVPLFKRMTDLS
AD169 SEQ ID NO: 6     QYGCEDNTLLGNHRTEECQLPSLKINIACNSAYEIVPLFKRMTDLS
```

Merlin SEQ ID NO: 1
AD169 SEQ ID NO: 6

```
              650           660           670           680           690
SNSFVPSMTADIDPLEINTDRVMELNSQRELRSMVFBLEEIMBEFNSYK
SNSFVPSMTADIDPLEINTDRVMELNSQRELRSMVFBLEEIMBEFNSYK 700           710           720           730           740
QRVKYVEDKV...VDPLPPYLKCDDLMSIGAAEKAVGVATIGAVGBAVASV
QRVKYVEDKV...VDPLPPYLKCDDLMSIGAAEKAVGVATIGAVGBAVASV

750
EGVAFERKP
EGVAFERKP
```

MODIFIED HUMAN CYTOMEGALOVIRUS PROTEINS

SEQUENCE LISTING

The instant application is filed with an electronically submitted Sequence Listing in ASCII text file format (Name: VU66804US01 SL.txt; Size: 166,216 bytes; and Date of Creation: 14 Feb. 2022) which is hereby incorporated by reference in its entirety.

FIELD OF THE INVENTION

This invention relates to recombinant human cytomegalovirus (HCMV) gB proteins.

BACKGROUND OF THE INVENTION

Human cytomegalovirus (HCMV) is a double stranded DNA virus of the β-herpesvirus subfamily. Congenital HCMV infection is the leading cause of hearing loss, vision loss and neurological disability. In addition, HCMV causes life-threatening illnesses in individuals with a compromised immune system, such as AIDS patients or transplant recipients. A vaccine against HCMV is needed.

At least twenty viral proteins are expressed on the HCMV envelope, including glycoproteins B, L and O (gB, gL and gO, respectively), and proteins UL128, UL130 and UL131A. The glycoprotein gB trimer and gH/gL heterodimer form a core fusion machinery. HCMV cell entry consists of a two-step mechanism: receptor binding and membrane fusion. While the gH/gL/gO and gH/gL/UL128/UL130/UL131A (corresponding to the HCMV pentamer) oligomers recognize their cognate receptors on cell membranes and regulate cell tropism, the gB trimer mediates membrane fusion and acts as a viral fusogen. Based on their structural properties, viral fusogens are divided into three classes, with HCMV gB belonging to class III. Viral fusogens are anchored into the viral envelope and reside in a metastable pre-fusion state on the viral membrane. Upon triggering, viral fusogens undergo a conformational rearrangement, switching to a stable post-fusion conformation and facilitating the merging of the viral lipid envelope with the host cell membrane.

There is a need to develop stable and soluble HCMV gB proteins that are not in a post-fusion conformation and to produce recombinant HCMV gB antigens in a non-post-fusion conformation.

SUMMARY OF THE INVENTION

The present inventors designed constructs that produce HCMV gB proteins in non-post-fusion conformation, or that interfere with the transition of the HCMV gB protein from pre-fusion to post-fusion conformation. Without wishing to be bound by theory, it is believed that the "non-post-fusion" conformation referred to herein is the "pre-fusion" conformation. To do so, the inventors replaced the amino acid residues c-terminal to the residue corresponding to K724 of SEQ ID NO: 1 with a heterologous trimerization domain that promotes the formation of stable trimers, such as a GCN4 Leucine Zipper domain. Stated another way, the gB protein was truncated by deleting the amino acids c-terminal to the residue corresponding to K724 of SEQ ID NO: 1, thus removing a part of the membrane proximal region as well as both the transmembrane domain and the cytoplasmic domain. A heterologous multimerization domain, such as GCN4 Leucine Zipper domain (GCN4 domain), was added to the C-terminus of the truncated gB protein. This modification is sufficient to produce gB proteins in non-post-fusion conformation. The present result is surprising because GCN4 domain insertions into other herpesvirus gB proteins (those from HSV and EBV) have been reported as failing to either stabilize the recombinant gB protein in a non-post-fusion conformation or to interfere with the transition from pre-fusion to post-fusion conformation. See Vitu et al. 2013 J. Mol. Biol. 425(11): 2056-2071 (regarding HSV gB) and Backovic et al. 2007 Virology 368(1): 102-113 (regarding EBV gB). The present result is particularly surprising in view of at least Vitu et al. (2013 J. Mol. Biol. 425(11): 2056-2071) who postulate that the transmembrane region and cytodomain are required for the stability of prefusion conformation.

The present inventors further modified the gB molecule with one or more proline substitution(s) (such as one or two proline substitutions) (in particular, a proline substitution at a residue corresponding to any one of N478-R511; or more specifically A503-R511) (see Table 2 and the Examples herein) which substitutions increased the percentage of molecules produced in the non-post-fusion conformation. Combining one or more of these proline substitutions with c-terminal truncation and addition of a heterologous trimerization domain will drive protein production toward gB molecules in non-post-fusion conformation and away from gB molecules in post-fusion conformation (see FIGS. 3A, 3B, 4A, and 4B). This result is surprising because combining a GCN4 domain insertion with modification of ectodomain residues in other herpesvirus gB molecules has not been reported as disrupting the transition of gB from pre-fusion to post-fusion conformation (see Vitu et al. 2013 J. Mol. Biol. 425(11): 2056-2071).

To increase the percentage of molecules in the non-post-fusion conformation, the gB molecule may additionally be modified with any helix-breaking substitution(s) or insertion(s) of one or more G, S, A, or P residues. Such helix-breaking modifications occur at one or more (e.g., one or two) residues corresponding to N478-R511; or more specifically A503-R511 (numbered according to SEQ ID NO:1). See Table 2 herein. Combining one or more of these modifications with the addition of a heterologous trimerization domain modification as described herein (c-terminal truncation and addition of trimerization domain such as GCN4) will drive protein production toward gB molecules in non-post-fusion conformation and away from gB molecules in post-fusion conformation.

Without wishing to be bound by theory, the present inventors believe that c-terminal truncation and addition of a heterologous trimerization domain, as described herein, in an HCMV gB protein (specifically in an HCMV Merlin strain gB protein or HCMV AD169 strain gB protein) is sufficient to disrupt the transition of the viral gB protein from pre-fusion to post-fusion conformation or to stabilize the gB protein in a non-post-fusion conformation. More specifically, the heterologous trimerization domain is located c-terminally adjacent to the residue corresponding to K724 of SEQ ID NO: 1.

The present inventors further describe incorporating an additional modification (a proline substitution) of at least one of the following (such as one or two of the following), to increase production of HCMV gB proteins in non-post-fusion conformation:
  HCMV Merlin gB residues N478-R511 of SEQ ID NO: 1;
  HCMV AD169 gB residues N477-R510 of SEQ ID NO: 6.

Protein expression of the modified HCMV gB proteins as described herein increases the percentage of gB proteins produced in the non-post-fusion conformation (as compared to production of non-modified HCMV gB proteins).

One aspect of the present invention provides a modified HCMV gB protein comprising a heterologous trimerization domain operably linked c-terminal to the residue corresponding to 724 numbered according to SEQ ID NO: 1 (specifically K724 numbered according to SEQ ID NO: 1). The modified gB protein herein may be truncated, i.e., not comprise the native amino acid residues c-terminal to the residue corresponding to 724, numbered according to SEQ ID NO: 1 (specifically, does not comprise the native amino acid residues corresponding to 725-907 of SEQ ID NO: 1). Such native amino acid residues form a portion of the MPR domain, the transmembrane domain, and the cytoplasmic domain (FIG. 1).

In another aspect, the modified HCMV gB protein has an amino acid linker sequence between the residue corresponding to 724, numbered according to SEQ ID NO: 1 (i.e., the c-terminal-most residue of the truncated MPR) and the GCN4 domain. Suitable linker sequences include a single amino acid (such as a single proline, serine, glycine or alanine residue), two amino acid residues (such as two proline (P), serine (S), glycine (G) or alanine (A) residues, or any combination thereof), or any short amino acid sequence that functions as a linker sequence.

In certain aspects, the heterologous trimerization domain is a GCN4 Leucine Zipper domain (GCN4); a suitable GCN4 domain comprises or consists of the amino acid sequence provided as SEQ ID NO: 2. Additional multimerization domains that drive the symmetric self-assembly of trimers of soluble proteins are known in the art (Engel et al. 2000 Matrix Biology 19.4:283-288), and may be used in the present invention. Examples of suitable multimerization domains include: (1) the GCN4 leucine zipper (Harbury et al. 1993 Science 262: 1401-1407); (2) the phage T4 fibritin foldon (Miroshnikov et al. 1998 Protein Eng 11:329-414 (3) collagen (McAlinden et al. 2003 Biol Chem 278:42200-42207; see also US patent publication 2017/0182151), and (4) De novo designed trimeric oligomers (Boyken et al. 2016 Science 352:680-687).

In certain aspects, the modified HCMV gB protein comprises a substitution modification of one or more furin cleavage site amino acid, including but not limited to R457S and R460S substitutions (numbered per SEQ ID NO:1).

In certain aspects, the modified HCMV gB protein comprises a substitution modification of one or more fusion loop amino acids, including but not limited to substitution modifications at FL1 residues 155-157 and/or FL2 residues 240-242 (numbered per SEQ ID NO: 1), such as Y155G, I156H, H157R, W240F, L241F, and Y242H (numbered per SEQ ID NO: 1).

In other aspects, the modified HCMV gB protein comprises a purification tag (e.g., a 6-histidine purification tag) and may also comprise a cleavage linker (e.g., a TEV cleavage linker).

In one aspect, the modified HCMV gB protein comprises a proline substitution of one or more Domain III Coiled-coil (DIIIcc) Region amino acid residues corresponding to N478-R511 numbered according to SEQ ID NO: 1. In a further aspect such DIIIcc amino acid residues are any one or more (such as one or two) of the residues listed within Table 2.

In one aspect, the modified HCMV gB protein comprises a helix-breaking substitution (amino acid substitution of one or more G, S, A, or P residues) for one or more Domain III Coiled-coil (DIIIcc) Region amino acid residues corresponding to N478-R511 numbered according to SEQ ID NO: 1. In a further aspect such DIIIcc amino acid residues are any one or more (such as one or two) of the residues listed within Table 2.

In another aspect, the modified HCMV gB protein is operably linked to a carrier. In certain aspects, the carrier is a nanoparticle. In further aspects, the nanoparticle is, or is derived from, lumazine synthase or ferritin proteins, or other bacterial, viral proteins, or de novo designed symmetric carriers (Yeates et al. 2017 Annual Reviews of Biophysics 46:23-42) that form nanoparticles.

In another aspect is provided isolated nucleic acids comprising a polynucleotide sequence encoding the modified HCMV gB proteins herein. The nucleic acid may be an RNA. The RNA may be self-replicating RNA, optionally an alphavirus replicon. An alphavirus replication particle (VRP) may comprise the alphavirus replicon.

In another aspect is provided immunogenic compositions comprising a modified HCMV gB protein, nucleic acid, or VRP of herein. Immunogenic compositions may comprise an adjuvant, and the adjuvant may comprise aluminum salt, a TLR7 agonist, TLR4 agonist, MPL, 3D-MPL, saponin, or an oil-in-water emulsion. Immunogenic compositions herein may comprise a modified HCMV gB protein and at least one additional protein or nucleic acid antigen. The at least one additional antigen may be an HCMV protein, or immunogenic fragment thereof, such as gO, gH, gL, pUL128, pUL130, pUL131, pp65, IE1, or a combination thereof.

In one aspect is provided a recombinant vector comprising a nucleic acid described herein.

In a further aspect is provided an isolated host cell comprising a nucleic acid as described herein. The nucleic acid may comprise a polynucleotide that is DNA and such DNA may be stably incorporated into the genomic DNA of the host cell. The host cell may be a mammalian cell. The mammalian cell may be a CHO cell or HEK-293 cell.

In an aspect is provided a cell culture comprising a host cell as described herein.

In another aspect is provided processes of producing a modified HCMV gB protein comprising culturing a host cell undersuitable conditions, and optionally then collecting the modified gB protein from the cultured host cell(s), and optionally purifying the modified gB protein.

In further aspects is provided processes of producing a population of host cells, comprising culturing host cells under suitable conditions for expression of a modified HCMV gB protein as described herein and optionally purifying the modified gB protein, wherein at least 35%, 36%, 37%, 38%, 39%, 40%, 41%, 42%, 43%, 44%, or 45% of the purified modified gB proteins are in pre-fusogenic conformation.

In one aspect is provided a population of host cells wherein at least 35%, 36%, 37%, 38%, 39%, 40%, 41%, 42%, 43%, 44%, or 45% of the modified HCMV gB proteins expressed from said host cells are in pre-fusogenic conformation.

In another aspect is provided an isolated antibody, or antigen-binding fragment thereof, specific for a modified HCMV gB protein described herein. A pharmaceutical composition may comprise such antibody, or antigen-binding fragment thereof.

Another aspect provides uses of the modified HCMV gB proteins, nucleic acids, VRPs, immunogenic compositions, vectors, antibodies or antibody fragments, or pharmaceutical compositions described herein for the prevention or treatment of HCMV infection, for inducing an immune response against HCMV, for the manufacture of a medicament for inducing an immune response against HCMV, or for the manufacture of a medicament for inhibiting HCMV entry into a cell.

Also provided are methods of inhibiting membrane fusion of HCMV to a cell, inhibiting HCMV entry into a cell, or inducing an immune response against HCMV in a subject, comprising contacting the cell with the modified HCMV gB proteins, nucleic acids, VRPs, immunogenic compositions, vectors, antibodies or antibody fragments, or pharmaceutical compositions described herein.

In another aspect is provided kits for identifying the presence of a modified HCMV gB protein within a composition, for the purification of a modified HCMV gB protein from a composition, for detecting a modified HCMV gB protein in pre-fusion conformation or a non-post-fusion conformation, or for the prevention or treatment of HCMV virus infection; comprising the antibody or antigen-binding fragment as described herein. Such kits may include instructions for using the antibody or antigen-binding fragment thereof.

BRIEF DESCRIPTION OF THE FIGURES

FIG. 2A and FIG. 2B provide an alignment spanning the Domain III Coiled-coil (DIIIcc) Region and Membrane Proximal Region (MPR) amino acid residues of (top to bottom) HCMV Merlin strain gB (SEQ ID NO: 1), HCMV AD169 strain gB (SEQ ID NO: 6). Residue numbering is provided with respect to SEQ ID NO: 1 and, in this way, demonstrates what is meant by an HCMV AD169 gB amino acid residue that "corresponds to" a residue "numbered according to SEQ ID NO: 1".

DETAILED DESCRIPTION

1. Overview

The crystal structure of the post-fusion HCMV gB ectodomain revealed a trimeric oligomer with five defined structural domains (Chandramouli et al. 2015 Nat. Comm. 6(8176): 1-12 and Burke & Heldwein 2015 PLOS Path. DOI: 10.1371).

Figure 1:
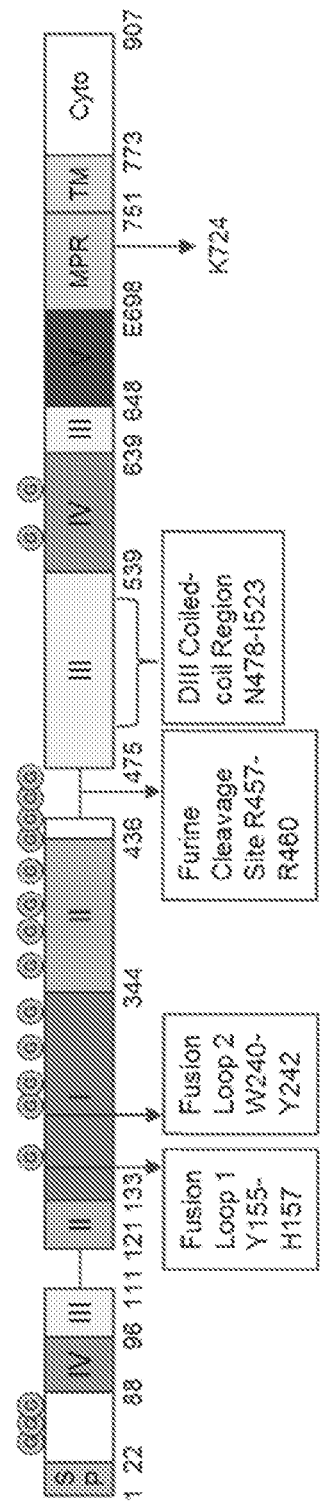
FIG. 1 is a schematic representation of the HCMV gB protein from the Merlin strain. Abbreviations therein are as follows: "TM" meaning transmembrane domain; "Cyto" meaning cytoplasmic domain; "SP" meaning signal peptide; "MPR" meaning membrane proximal region; "I" meaning Domain I; "II" meaning Domain II; "µI" meaning Domain III; "IV" meaning Domain IV; and "V" meaning Domain V. The amino acid numbering and residues are based on HCMV Merlin strain gB sequence SEQ ID NO: 1 (see also Chandramouli et al., 2015 Nat. Commun. 6(8176):1-12; and WO 2016/092460 (corresponding to US 2018/0265551)). Circled 'G' represents N glycosylation site. Fusion loops, Furine Cleavage Site, and DIII Coiled-coil region are indicated according to the HCMV Merlin strain gB sequence (SEQ ID NO:1).

A HCMV vaccine containing soluble post-fusion gB adjuvanted with MF59 has been reported as inducing a potent immunogenic response against gB in a Phase I trial (Frey et al. 1999 J. Infect. Dis. 180(5):1700-1703; Li et al. 2017 NPJ Vaccines 2(36) DOI: 10.1038/s41541-017-0038-0). In addition, different Phase II studies with post-fusion HCMV gB+MF59 reported 50% efficacy for prevention of primary HCMV infection in postpartum women, 43% efficacy in seronegative adolescent girls and reduced viremia in solid-transplant-recipients with seropositive organ donors (Pass et al. 2009 New Engl. J. Med. 360:1191-1199; Griffiths et al. 2011 Lancet 377(9773):1256-1263; Bernstein et al. 2016 Vaccine 34(3):313-319). Recently, two independent studies reported that protection conferred by HCMV post-fusion gB subunit vaccine is not dependent on neutralizing antibodies (Nelson et al. 2018 PNAS 115(24): 6267-6272; Baraniak et al. 2018 PNAS 115(24): 6273-6278), possibly indicating that vaccine-induced neutralizing responses should target epitopes in the pre-fusion form. A high-resolution structure of the pre-fusion HCMV gB has not yet been determined. A recent study on whole HCMV virions purports to show a low-resolution model of the pre-fusogenic state based on cryo-electron tomography and resolved to 21 Å (EMDB ID EMD-9328 with primary publication by Si et al. 2018 PLOS Path. 14(12): e1007452). This supposed pre-fusion gB model has a Christmas tree-like conformation, where the apical part seems to belong to the coiled-coil region of Domain III (which is usually buried in the post-fusion conformation) (FIG. 1). But the low-resolution model by Si Z. et al. does not allow for structural design of an HCMV gB molecule (e.g., one that is not in post-fusion conformation) and, in particular, structural design of a stable HCMV gB molecule in the pre-fusion conformation.

As described and exemplified herein, the inventors have discovered that certain modifications introduced to HCMV gB protein stabilize it in a non-post-fusion conformation, or interfere with the protein's transition from pre-fusion to post-fusion conformation. In particular, the gB protein is truncated within the Membrane Proximal Region (MPR) and operably linked to a heterologous trimerization domain (such as a GCN4 Leucine Zipper domain), optionally with an amino acid linker sequence (such as two proline residued) inserted between the truncated MPR and the heterologous trimerization domain. In particular, the MPR truncation comprises a deletion of the amino acids that are c-terminal to the residues listed in Table 1.

The modified HCMV gB molecules may be further modified in the Domain III Coiled-coil Region, to include any helix-breaking amino acid substitution(s) or insertion(s), such as with one or more G, S, A, or P residues. The substitution of one or more of the residues listed in Table 2 to proline is one such modification.

Other modifications as described herein or as known by the art (e.g., modification of a furin cleavage site, a fusion loop(s), or addition of a purification tag) may also be included in the modified HCMV gB proteins of the present invention.

2. Aspects and Definitions

HCMV gB is an envelope glycoprotein B having numerous roles, one of which is the involvement in the fusion of the cytomegalovirus with host cells. It is encoded by the UL55 gene of HCMV genome. The size of the native form of HCMV gB depends on the size of the open reading frame (ORF) which may vary a little according to the strain. For example, the ORF of AD169 strain, which is 2717 bp long, encodes a full length gB of 906 amino acids, whereas the ORF of Towne and Merlin strains encode a full length gB of 907 amino acids. Although the present invention is applicable to gB proteins originating from any HCMV strain, in order to facilitate its understanding, when referring to amino acid positions in the present specification, the numbering is given in relation to the amino acid sequence of the gB protein of SEQ ID NO:1 originating from the clinical isolate Merlin strain, unless otherwise stated. The present invention is not, however, limited to the HCMV Merlin strain.

Figure 5:
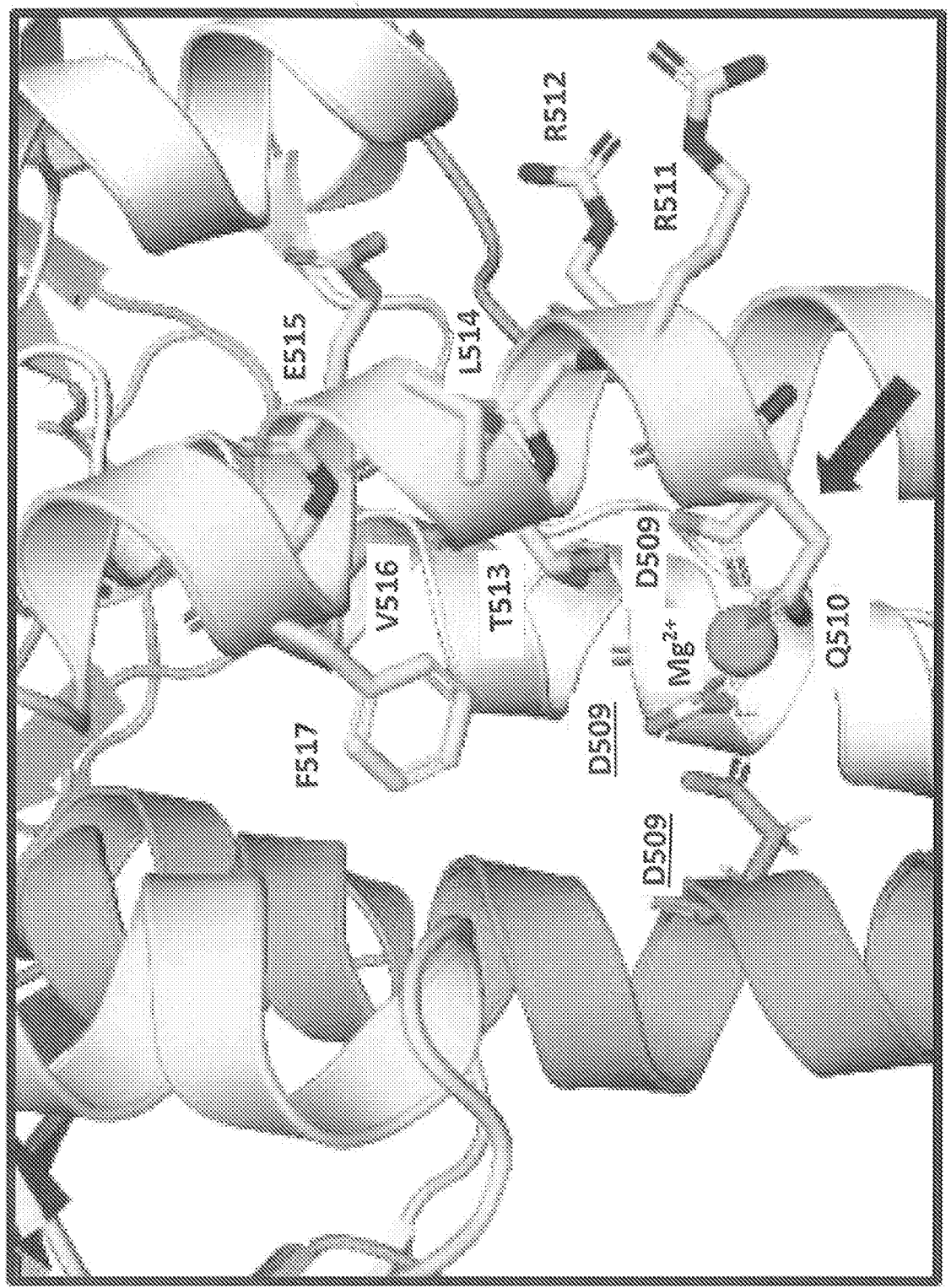
FIG. 5 depicts HCMV Merlin strain gB as a trimer and indicates alpha helices residues D509 (three shown due to trimer), Q510, R511, R512, T513, L514, E515, V516, and F517 (numbered according to SEQ ID NO: 1). Also shown is the magnesium ion (Mg2+) between the alpha helices. Residue Q510 is denoted with an arrow.

Therefore, when referring to "comparable" or "corresponding" amino acid positions or specific amino acids in a gB protein of any other HCMV strain (also relevant in the context of nucleic acids), such "comparable" or "corresponding" residues (or nucleic acids) can be determined by those of ordinary skill in the art using known information (see FIG. 5 of Deckers et al. 2009 Vir. J. 6(210): 1-12; Foglierini et al. 2019 Front. Micro. 19(1005): 1-8; WO 2012/049317 (corresponding to US 2013/0216613); and WO 2016/092460 (corresponding to US 2018/0265551; and Burke & Heldwein 2015 PLOS Path. DOI: 10.1371) and by sequence alignment using readily available and well-known alignment algorithms (such as BLAST, using default settings; ClustalW2, using default settings; or algorithm disclosed by Corpet, Nucleic Acids Research, 1998, 16(22): 10881-10890, using default parameters). An example of using sequence alignment to determine which residues "correspond to" a referenced residue is provided at FIGS. 2A and 2B (see also FIG. 2 of Burke & Heldwein 2015 PLOS Path. DOI: 10.1371). Accordingly, when referring to a "HCMV gB protein", it is to be understood as a HCMV gB protein from any strain. The actual residue location number and residue identity may have to be adjusted for gB proteins from HCMV other than HCMV Merlin strain, depending on the actual sequence alignment. (See also Table 1 and FIGS. 2A and 2B).

In one aspect, the modified HCMV gB protein comprises a helix-breaking substitution (amino acid substitution of one or more G, S, A, or P residues) for one or more Domain III Coiled-coil (DIIIcc) Region amino acid residues corresponding to N478-R511 (numbered according to SEQ ID NO: 1). Such DIIIcc amino acid residues include any one or more (such as one or two) of the residues listed within Table 2. Suitable proline substitutions include K723P of HCMV AD169 strain gB amino acid sequence SEQ ID NO: 6 (corresponding to K724 residue of SEQ ID NO:1).

TABLE 1

Summary of Corresponding
MPR Residues

| HCMV Merlin Strain gB SEQ ID NO: 1 UniProtKB F5HB53 MPR residue K724 | HCMV AD169 Strain gB SEQ ID NO: 6 UniProtKB P06473 MPR residue K723 |
|---|---|

Amino acid residues corresponding to position 478 of SEQ ID NO: 1 from SEQ ID NO: 6 are set forth below in Table 2, numbered according to (or "with respect to") SEQ ID NO: 1. A gB residue that "corresponds to" a residue in a different HCMV gB may have a different position number, may be a different amino acid, or both (see also FIGS. 2A-2B).

TABLE 2

Summary of Corresponding
Domain III Coiled-coil (DIIIcc)
Region Residues
(Read By Rows)

| DIIIcc Amino Acid position | HCMV Merlin Strain gB SEQ ID NO: 1 UniProtKB F5HB53 | HCMV AD169 Strain gB SEQ ID NO: 6 UniProtKB P06473 |
|---|---|---|
| 1 | N478 | N477 |
| 2 | L479 | L478 |
| 3 | V480 | V479 |
| 4 | Y481 | Y480 |
| 5 | A482 | A481 |
| 6 | Q483 | Q482 |
| 7 | L484 | L483 |
| 8 | Q485 | Q484 |
| 9 | F486 | F485 |
| 10 | T487 | T486 |
| 11 | Y488 | Y487 |
| 12 | D489 | D488 |
| 13 | T490 | T489 |
| 14 | L491 | L490 |
| 15 | R492 | R491 |
| 16 | G493 | G492 |
| 17 | Y494 | Y493 |
| 18 | I495 | I494 |
| 19 | N496 | N495 |
| 20 | R497 | R496 |
| 21 | A498 | A497 |
| 22 | L499 | L498 |
| 23 | A500 | A499 |
| 24 | Q501 | Q500 |
| 25 | I502 | I501 |
| 26 | A503 | A502 |
| 27 | E504 | E503 |
| 28 | A505 | A504 |
| 29 | W506 | W505 |
| 30 | C507 | C506 |
| 31 | V508 | V507 |
| 32 | D509 | D508 |
| 33 | Q510 | Q509 |
| 34 | R511 | R510 |

As yet a further example, it would be well understood by the art that, for example, the HCMV AD-169 strain gB Fusion Loop 1 (FL1) sequence $^{155}$YIY$^{157}$ "corresponds to" or is "comparable to" the HCMV Merlin strain gB FL1 sequence $^{155}$YIH$^{157}$ (Y$^{157}$ from AD-169 strain gB corresponding to H$^{157}$ of Merlin strain gB) (compare WO 2012/049317 (corresponding to US 2013/0216613) and WO 2016/092460 (corresponding to US 2018/0265551).

Orientation within a polypeptide is generally recited in an N-terminal to C-terminal direction, defined by the orientation of the amino and carboxy moieties of individual amino acids. Polypeptides are translated from the N-terminal or amino-terminus towards the C-terminal or carboxy-terminus.

The native form of HCMV Merlin strain gB is set forth in FIG. 1 and generally contains, in the N-terminal to C-terminal direction of the protein, (i) an amino acid signal sequence or signal peptide (here designated as residues 1-22 of SEQ ID NO: 1, but designated by some as residues 1-24 of SEQ ID NO: 1 (see UniProtKB Accession No. F5HB53)), known to be involved in the polypeptide intracellular trafficking including targeting the polypeptide towards secretion, followed by (ii) a region called the leader sequence, (iii) an extracellular domain containing five structural domains (I-V) and an endoproteolytic furin cleavage site (with Domain I comprising two fusion loops), (iv) a Membrane Proximal Region (MPR), (v) a transmembrane domain and (vi) a C-terminal cytoplasmic domain.

In general, the HCMV gB protein forms a monomeric trimer (comprising three gB proteins, also referred to as subunits) that can be used as an antigen against HCMV. However, the monomeric trimer comprises an exposed hydrophobic surface, which can cause significant problems in both antigen production and purification. For example, the hydrophobic surface can cause aggregation of recombinantly produced gB protein (e.g., two monomeric trimers can form a dimeric trimer via the hydrophobic surface, which may cause production problems). The hydrophobic surface also causes the monomeric gB trimer to adhere to the host cell (e.g., to cell membrane, ER membrane, other hydrophobic proteins, aggregated proteins, etc.). To reduce aggregation and/or increase protein secretion of a gB protein, one or more residues within either or both of Fusion Loop 1 and Fusion Loop 2 corresponding to residues 155-157 and 240-242, respectively, of SEQ ID NO: 1 may be modified (e.g., by amino acid residue substitution) (see Chandramouli et al. 2015 Nat. Comm. 6(8176): 1-12; WO 2012/049317 (corresponding to US 2013/0216613) and WO 2016/092460 (corresponding to US 2018/0265551).

Proteins (or polypeptides) herein may be modified to carry further modifications, such as for instance, modifications at endoproteolytic cleavage sites so that said sites are made ineffectual. For example, the furin cleavage site located around amino acids 457 to 460 of the sequence set forth in SEQ ID NO:1, or at a corresponding position in other gB proteins originating from different HCMV strains, may be modified. See WO 2012/049317 (corresponding to US 2013/0216613) and WO 2016/092460 (corresponding to US 2018/0265551).

The term "fragment," in reference to a polypeptide, refers to a portion (that is, a subsequence) of a polypeptide. An "immunogenic fragment" of a gB protein refers to a fragment that retains at least one immunogenic epitope (e.g., a predominant immunogenic epitope or a neutralizing epitope) of the full-length gB protein. Several antigenic domains (AD) of gB have been described (e.g., AD-1, AD-2, AD-3, AD-4, AD-5). See, e.g., Chandramouli et al. 2015 Nat. Comm. 6(8176): 1-12 and WO 2016/092460 (corresponding to US 2018/0265551). In certain aspects of the invention, the immunogenic fragment described herein comprises an antigenic domain selected from the group consisting of AD-1, AD-2, AD-3, AD-4, AD-5, and a combination thereof. An "immunogenic fragment" of a modified gB protein still comprises all of the modifications made to, or present in, the corresponding portion of the full length, referenced modified gB protein.

While their structure is distinct from non-modified polypeptides, the modified gB proteins of the present invention maintain immunogenic properties or epitope(s), so it is a further object of the present invention to utilize the modified polypeptides and modified fragments thereof in polypeptide/antibody interactions. The invention therefore provides antibodies which recognise a modified HCMV gB protein as described herein and, further, an antibody that is specific for such modified HCMV gB protein. The antibodies of the present invention may be a monoclonal antibody, polyclonal antibody, multispecific antibody (e.g., bispecific antibodies), labelled antibody, or antibody fragment so long as they exhibit the desired antigen-binding activity. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

Alternatively, the modified HCMV gB proteins herein may be used to identify antibodies using in vitro selection methods, such as phage display using diverse antibody libraries. The invention also provides a method for raising antibodies using a modified gB protein of the invention. An antibody or antibody fragment of the invention may be human or humanised. The antibodies of the invention may be used in a diagnostic assay and may be labelled directly or indirectly. In some embodiments, the antibodies of the invention may be used in therapy, for example in the treatment HCMV infection and may be in the form of neutralizing antibodies, which can inhibit or neutralize a gB protein's biological activity.

Attachment of a glycan to a gB protein creates a physical barrier (as well as a more hydrophilic surface) to reduce aggregation/adhesion via the hydrophobic surface. Glycosylation sites can be introduced into desired locations by suitable modification of amino acid sequences of the gB protein. See WO 2016/092460 (corresponding to US 2018/0265551). Preferably, N-linked glycosylation sites, comprising the N—X-S/T/C motif, are introduced. Preferably, the motif is N-X-S/T. Preferably, X is not proline. Similarly, sites for O-linked glycosylation can also be added. In O-linked glycosylation, the carbohydrate moiety is linked to the hydroxyl oxygen of serine and threonine. In addition, O-linked glycosylation also occurs at tyrosine, 5-hydroxylysine, and 4-hydroxyproline.

Amino acids may be substituted for (replaced by) a "hydrophilic" or "comparatively more hydrophilic" amino acid. The hydrophobicity of a particular amino acid sequence can be determined using a hydrophobicity scale, such as the Kyte and Dolittle scale (Kyte et al. 1982. J. Mol. Bio. 157: 105-132). Hydrophobicity of an amino acid sequence or a fragment thereof is dictated by the type of amino acids composing this sequence or a fragment thereof. Amino acids are commonly classified into distinct groups according to their side chains. For example, some side chains are considered non-polar, i.e. hydrophobic, while some others are considered polar, i.e. hydrophilic. Alanine (A), glycine (G), valine (V), leucine (L), isoleucine (I), methionine (M), proline (P), phenylalanine (F) and tryptophan (W) are considered to be hydrophobic amino acids, while serine (S), threonine (T), asparagine (N), glutamine (Q), tyrosine (Y), cysteine (C), lysine (K), arginine (R), histidine (H), aspartic acid (D) and glutamic acid (E) are considered to be polar amino acids. Regardless of their hydrophobicity, amino acids are also classified into subgroups based on common properties shared by their side chains. For example, phenylalanine, tryptophan and tyrosine are jointly classified as aromatic amino acids and will be considered as aromatic amino acids within the meaning of the present invention. Aspartate (D) and glutamate (E) are among the acidic or negatively charged amino acids, while lysine (K), arginine (R) and histidine (H) are among the the basic or positively charged amino acids, and they will be considered as such in the sense of the present invention. Hydrophobicity scales are available which utilize the hydrophobic and hydrophilic properties of each of the 20 amino acids and allocate a hydrophobic score to each amino acid, creating thus a hydrophobicity ranking. As an illustrative example only, the Kyte and Dolittle scale may be used (Kyte et al. 1982. J. Mol. Bio. 157: 105-132). This scale allows one skilled in the art to calculate the average hydrophobicity within a segment of predetermined length. Accordingly, hydrophobic regions in an amino acid sequence may be identified by the skilled person as potential targets for modification in accordance with the present invention. The ability of the modification of said regions to induce an improved product profile of the resulting modified protein, i.e. favoring the monomeric trimers proportion within the population, may then be tested as described below. The modification of a hydrophobic region may be an addition, deletion, or substitution of amino acid(s) within the hydrophobic surface (e.g., substituting hydrophobic amino acids with polar amino acids).

Further modifications not described herein but known to the art (specifically known to the art regarding HCMV gB proteins), as well as combinations of modifications described herein, may be performed. The resulting modifications can be analyzed, e.g., by scanning electron microscope (SEM), computer modeling, sedimentation (such as analytical ultracentrifugation (AUC)), chromatography etc., to assess the production of monomeric trimer. For example, size exclusion chromatography (SEC), such as size exclusion chromatography based on UV (SEC-UV) may be used. Alternatively, the sample can be treated with a cross-linking agent, so as to form covalent bonds between two proteins. After cross-linking, loading the sample on a gel in denaturing conditions, such as SDS-PAGE, and staining the gel for the presence of proteins, for example with Coomassie blue or silver nitrate, will display aggregates, if any, which are separated according to their molecular weight. See WO 2016/092460 (corresponding to US 2018/0265551).

A modification of HCMV gB protein residue C246 of SEQ ID NO:1 (or at a corresponding position in other HCMV gB proteins) may be introduced. Such modification can be, e.g., C246S, C246A, or C246G (or corresponding residues). It appears that C246 is an unpaired cysteine and modifying this unpaired cysteine can reduce the undesired formation of inter-molecular disulfide bonds. There is another potential unpaired cysteine at the C-terminal region (residue 779 of SEQ ID NO:1). If present, this cysteine (or corresponding cysteines in other HCMV gB proteins) may also be modified. See WO 2016/092460 (corresponding to US 2018/0265551).

Optionally, to facilitate expression and recovery, the HCMV gB protein (or immunogenic fragment thereof) may include a signal peptide at the N-terminus. A signal peptide can be selected from among numerous signal peptides known in the art, and is typically chosen to facilitate production and processing in a system selected for recombinant expression of the HCMV gB protein (or immunogenic fragment thereof). In general, signal peptides are 5-30 amino acids long, and are typically present at the N-terminus of a newly synthesized protein. The core of the signal peptide generally contains a long stretch of hydrophobic amino acids that has a tendency to form a single alpha-helix. In addition, many signal peptides begin with a short hydrophilic (usually positively charged) stretch of amino acids, which may help to enforce proper topology of the polypeptide during translocation. At the end of the signal peptide (C-terminus), there is typically a stretch of hydrophilic amino acids that is recognized and cleaved by signal peptidase. Signal peptidase may cleave either during or after completion of translocation to generate a free signal peptide and a mature protein.

In certain embodiments, the signal peptide included in the modified HCMV gB peptide is the signal peptide naturally present in the native HCMV gB protein, where "native" means naturally occurring or as found in nature. For Merlin and AD169 strains, the signal peptide is located at residues 1-22 (i.e., 1-22 of SEQ ID NO:1). Signal peptide from other HCMV strains can be identified by sequence alignment. Alternatively, the signal peptide may be a heterologous sequence in that the sequence arises from a protein distinct from gB. Exemplary signal peptides suitable for use in the context of the HCMV gB protein (or an immunogenic fragment thereof) described herein include signal peptides of tissue plasminogen activator (tPA), Herpes Simplex Virus (HSV) gD protein, human endostatin, HIV gp120, CD33, human Her2Neu, gp67, or Epstein Barr Virus (EBV) gp350. The signal peptide can be non-native and may comprise modifications, such as substitutions, insertions, or deletions of amino acids. In particular, modifications can be introduced at C-terminal part of the signal peptide.

Optionally, the modified HCMV gB proteins (or immunogenic fragment thereof) of the invention can include the addition of an amino acid sequence that constitutes a tag, which can facilitate detection (e.g. an epitope tag for detection by monoclonal antibodies) and/or purification (e.g. a polyhistidine-tag to allow purification on a nickel-chelating resin) of the proteins. Examples of affinity-purification tags include, e.g., 6×His tag (hexahistidine, binds to metal ion), maltose-binding protein (MBP) (binds to amylose), glutathione-S-transferase (GST) (binds to glutathione), FLAG tag (Asp-Tyr-Lys-Asp-Asp-Asp-Asp-Lys (SEQ ID NO: 7), binds to an anti-flag antibody), Strep tag (Ala-Trp-Arg-His-Pro-Gln-Phe-Gly-Gly (SEQ ID NO: 8), or Trp-Ser-His-Pro-Gln-Phe-Glu-Lys (SEQ ID NO: 9), or Trp-Ser-His-Pro-Gln-Phe-Glu-Lys-Gly-Gly-Gly-Ser-Gly-Gly-Gly-Ser-Gly-Gly-Gly-Ser-Trp-Ser-His-Pro-Gln-Phe-Glu-Lys (SEQ ID NO:10) binds to streptavidin or a derivative thereof), HA tag, MYC tag, or combination thereof.

In a certain embodiment, cleavable linkers may be used. This allows for the tag to be separated from the purified complex, for example by the addition of an agent capable of cleaving the linker. A number of different cleavable linkers are known to those of skill in the art. Such linkers may be cleaved for example, by irradiation of a photolabile bond or acid-catalyzed hydrolysis. There are also polypeptide linkers which incorporate a protease recognition site and which can be cleaved by the addition of a suitable protease enzyme including, for example, a Tobacco Etch Virus (TEV) cleavage linker (or cleavage site). It may be more desirable to express HCMV gB (or immunogenic fragment thereof) without an exogenous tag sequence (i.e., without a 6×His tag and TEV cleavage site), for example, for clinical safety or efficacy reasons.

When a host cell herein is cultured under suitable conditions, the nucleic acid can express a modified HCMV gB protein (or an immunogenic fragment thereof) as described herein. The modified HCMV gB protein may then be secreted from the host cell. Suitable host cells include, for example, insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster)), avian cells (e.g., chicken, duck, and geese), bacteria (e.g., *E. coli, Bacillus subtilis*, and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), Tetrahymena cells (e.g., Tetrahymena *thermophila*) or combinations thereof.

For modified HCMV gB proteins that comprise a glycosylation site, the host cell should be one that has enzymes that mediate glycosylation. Bacterial hosts are generally not suitable for such modified proteins, unless the host cell is modified to introduce glycosylation enzymes; instead, a eukaryotic host, such as insect cell, avian cell, or mammalian cell should be used.

Suitable insect cell expression systems, such as baculovirus systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. For example, for expression in insect cells a suitable baculovirus expression vector, such as pFastBac (Invitrogen), is used to produce recombinant baculovirus particles. The baculovirus particles are amplified and used to infect insect cells to express recombinant protein. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)).

Avian cell expression systems are also known to those of skill in the art and described in, e.g., U.S. Pat. Nos. 5,340, 740; 5,656,479; 5,830,510; 6,114,168; and 6,500,668; European Patent No. EP 0787180B; European Patent Application No. EP03291813.8; WO 03/043415; and WO 03/076601. Suitable avian cells include, for example, chicken embryonic stem cells (e.g., EBx cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression and will be apparent to those skilled in the art and in the references cited herein, including, e.g., Freshney (1994) Culture of Animal Cells, a Manual of Basic Technique, third edition, Wiley-Liss, New York and the references cited therein. Expression products corresponding to the nucleic acids of the invention can also be produced in non-animal cells such as plants, yeast, fungi, bacteria and the like. In addition to Sambrook, Berger and Ausubel, details regarding cell culture can be found in Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla. In bacterial systems, a number of expression vectors can be selected depending upon the use intended for the expressed product. For example, when large quantities of a polypeptide or fragments thereof are needed for the production of antibodies, vectors which direct high level expression of proteins that are readily purified are favorably employed. Such vectors include, but are not limited to, multifunctional E. coli cloning and expression vectors such as BLUESCRIPT (Stratagene), in which the coding sequence of interest, e.g., a polynucleotide of the invention as described above, can be ligated into the vector in-frame with sequences forthe amino-terminal translation initiating methionine and the subsequent seven residues of beta-galactosidase producing a catalytically active beta galactosidase fusion protein; pIN vectors (Van Heeke & Schuster (1989) J Biol Chem 264: 5503-5509); pET vectors (Novagen, Madison Wis.), in which the amino-terminal methionine is ligated in frame with a histidine tag; and the like. Similarly, in yeast, such as *Saccharomyces cerevisiae*, a number of vectors containing constitutive or inducible promoters such as alpha factor, alcohol oxidase and PGH can be used for production of the desired expression products. For reviews, see Berger, Ausubel, and, e.g., Grant et al. (1987; Methods in Enzymology 153:516-544). In mammalian host cells, a number of expression systems, including both plasmids and viral-based systems, can be utilized.

A host cell is optionally chosen for its ability to modulate the expression of the inserted sequences or to process the expressed protein in the desired fashion, including, but not limited to, glycosylation, acetylation, carboxylation, phosphorylation, lipidation, and acylation. Post-translational processing for example, which cleaves a precursor form into a mature form of the protein (for example, by a furin protease) is optionally performed in the context of the host cell. Different host cells such as 3T3, COS, CHO, HeLa, HEK, BHK, MDCK, 293, WI38, etc. have specific cellular machinery and characteristic mechanisms for such post-translational activities and can be chosen to ensure the correct modification and processing of the introduced, foreign protein. For long-term, high-yield production of modified gB protein encoded by the nucleic acids disclosed herein, stable expression systems are typically used. For example, cell lines which stably express a modified HCMV gB protein of the invention are obtained by introducing into the host cell expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding a modified HCMV gB protein are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium and purified. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption. Modified gB proteins can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxyapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art, including, e.g., those set forth in Sandana (1997) Bioseparation of Proteins, Academic Press, Inc.; and Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, U.K.; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ.

Preferably, the host cells are mammalian cells (e.g., human, non-human primate, horse, cow, sheep, dog, cat, and rodent (e.g., hamster). Suitable mammalian cells include, for example, Chinese hamster ovary (CHO) cells, human embryonic kidney cells (HEK-293 cells NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like.

In certain embodiments, the host cell is a CHO cell. In certain embodiments, the nucleic acid encoding the modified HCMV gB protein (or immunogenic fragment thereof) described herein is stably integrated into the genome of the CHO cell.

Various CHO cell lines are also available from European Collection of Cell Cultures (ECACC), or American Type Culture Collection (ATCC), such as CHO cell lines hCBE11 (ATCC PTA-3357™), E77.4 (ATCC PTA-3765™), hLT-B: R-hG1 CHO #14 (ATCC CRL-11965™), MOR-CHO-MORAb-003-RCB (ATCC PTA-7552™), AQ.C2 clone 11B (ATCC PTA-3274™), AQ.C2 clone 11B (ATCC PTA- 3274™), hsAQC2 in CHO-DG44 (ATCC PTA-3356™), xrs5 (ATCC CRL-2348™), CHO-K1 (ATCC CCL-61 ™), Led [originally named Pro-5WgaRI3C] (ATCC CRL-1735™), Pro-5 (ATCC CRL-1781 ™), ACY1-E (ATCC 65421™) ACY1-E (ATCC 65420™), pgsE-606 (ATCC CRL-2246™), CHO-CD36 (ATCC CRL-2092™), pgsC-605 (ATCC CRL-2245™), MC2/3 (ATCC CRL-2143™), CHO-ICAM-1 (ATCC CRL-2093™), and pgsB-618 (ATCC CRL-2241 ™). Any one of these CHO cell lines may be used.

Other commercially available CHO cell lines include, e.g., FREESTYLE™ CHO-S Cells and FLP-IN™-CHO Cell Line from Life Technologies.

Methods for expressing recombinant proteins in CHO cells in general have been disclosed. See, e.g., in U.S. Pat. Nos. 4,816,567 and 5,981,214.

In certain embodiments, the recombinant nucleic acids are codon optimized or codon-pair optimized for expression in a selected prokaryotic or eukaryotic host cell.

To facilitate replication and expression, the nucleic acids can be incorporated into a vector, such as a prokaryotic or a eukaryotic expression vector. Exemplary vectors include plasmids that are able to replicate autonomously or to be replicated in a host cell. Typical expression vectors contain suitable promoters, enhancers, and terminators that are useful for regulation of the expression of the coding sequence(s) in the expression construct. The vectors may also comprise selection markers to provide a phenotypic trait for selection of transformed host cells (such as conferring resistance to antibiotics such as ampicillin or neomycin). Nucleic acid or vector modification may be undertaken in a manner known by the art, see e.g., WO 2012/049317 (corresponding to US 2013/0216613) and WO 2016/092460 (corresponding to US 2018/0265551). For example, the nucleic acids that encode a modified HCMV gB protein as described herein are cloned into a vector suitable for introduction into mammalian cells (e.g., CHO cells). In this exemplary embodiment, the polynucleotide sequence that encodes the modified HCMV gB protein is introduced into the pMax vector developed by Amaxa. The polypeptide is expressed under a constitutive promoter, the immediate early CMV promoter. Selection of the stably transfected cells expressing the polypeptide is made based on the ability of the transfected cells to grow in the presence of kanamycin. Cells that have successfully integrated the pMax are able to grow in the presence of kanamycin, because the pMax vector expresses a kanamycin resistance gene. Selected cells can be clonally expanded and characterized for expression of the modified HCMV gB proteins. Alternatively, the polynucleotide sequences that encode the modified gB proteins of the invention may be introduced into the pTT5 vector developed by NRC, which expresses an ampicillin resistance gene.

Following transfection and induction of expression (according to the selected promoter and/or enhancers or other regulatory elements), the expressed polypeptides are recovered (e.g., purified, isolated, or enriched). To facilitate purification, the modified HCMV gB protein(s) may include a C-terminal polyhistidine tag (e.g., 6×His tag) and, optionally, further include a cleavage site (e.g., a TEV cleavage site).

The term "purification" or "purifying" refers to the process of removing components from a composition or host cell or culture, the presence of which is not desired. Purification is a relative term and does not require that all traces of the undesirable component be removed from the composition. In the context of vaccine production, purification includes such processes as centrifugation, dialyzation, ion-exchange chromatography, and size-exclusion chromatography, affinity-purification or precipitation. Thus, the term "purified" does not require absolute purity; rather, it is intended as a relative term. A preparation of substantially pure nucleic acid or protein can be purified such that the desired nucleic acid, or protein, represents at least 50% of the total nucleic acid content of the preparation. In certain embodiments, a substantially pure nucleic acid, or protein, will represent at least 60%, at least 70%, at least 80%, at least 85%, at least 90%, or at least 95% or more of the total nucleic acid or protein content of the preparation. Immunogenic molecules or antigens or antibodies which have not been subjected to any purification steps (i.e., the molecule as it is found in nature) are not suitable for pharmaceutical (e.g., vaccine) use.

In the sense of the present invention, a "purified" or an "isolated" biological component (such as a nucleic acid molecule, or protein) has been substantially separated or purified away from other biological components in the cell of the organism in which the component naturally occurs or was produced, such as, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

In certain embodiments, the modified HCMV gB protein (or immunogenic fragment thereof) described herein is purified or isolated. The modified gB protein (or immunogenic fragment thereof) can be purified using any suitable methods, such as HPLC, various types of chromatography (such as hydrophobic interaction, ion exchange, affinity, chelating, and size exclusion), electrophoresis, density gradient centrifugation, solvent extraction, or the like. For example, methods for purifying HCMV gB protein by immunoaffinity chromatography has been disclosed. Ruiz-Arguello et al., J. Gen. Virol., 85:3677-3687 (2004). As appropriate, the modified gB protein (or immunogenic fragment thereof) may be further purified, as required, so as to remove substantially any proteins which are also secreted in the medium or result from lysis of host cells, so as to provide a product which is at least substantially free of host debris, e.g., proteins, lipids and polysaccharides. See, e.g., those set forth in Sandana (1997) Bioseparation of Proteins, Academic Press, Inc.; and Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, U.K.; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ. If desired, the modified gB protein (or immunogenic fragment thereof) can include a "tag" that facilitates purification, as described above.

Exemplary procedures sufficient to guide one of ordinary skill in the art through the production of modified HCMV gB proteins and nucleic acids encoding them can be found in Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2003); and Ausubel et al., Short Protocols in Molecular Biology: A Compendium of Methods from Current Protocols in Molecular Biology, 4th ed., Wiley & Sons, 1999.

"Recombinant" as used herein to describe a polynucleotide means a polynucleotide of genomic, cDNA, RNA (including mRNA) semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

A "heterologous" sequence with regard to a HCMV gB protein refers to an amino acid or nucleotide sequence that is not found in naturally occurring HCMV gB protein, or in a nucleic acid encoding an HCMV gB protein, respectively. When a nucleic acid molecule is operably linked to another polynucleotide that it is not associated with in nature, the nucleic acid molecule may be referred to as "heterologous" (i.e., the nucleic acid molecule is heterologous to at least the polynucleotide). Similarly, when a polypeptide is in contact with or in a complex with another protein that it is not associated with in nature, the polypeptide may be referred to as "heterologous" (i.e., the polypeptide is heterologous to the protein). Further, when a host cell comprises a nucleic acid molecule or polypeptide that it does not naturally comprise, the nucleic acid molecule and polypeptide may be referred to as "heterologous" (i.e., the nucleic acid molecule is heterologous to the host cell and the polypeptide is heterologous to the host cell).

It will be understood by those of skill in the art, that the similarity between modified HCMV gB proteins (or polynucleotide sequences), as for protein (or nucleotide sequences) in general, can be expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid (or polynucleotide) sequences, the more similar are the higher order structures resulting from folding and assembly. Variants of HCMV gB proteins and polynucleotide sequences (e.g., those originating from different HCMV strains) can have one or a small number of amino acid deletions, additions or substitutions as compared to another, but will nonetheless share a very high percentage of their amino acid, and generally their polynucleotide sequence. Methods of determining sequence identity are well known in the art. Various programs and alignment algorithms are described in: Smith and Waterman, Adv. Appl. Math. 2:482, 1981; Needleman and Wunsch, J. Mol. Biol. 48:443, 1970; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. USA 85:2444, 1988. Altschul et al., Nature Genet. 6:119, 1994, presents a detailed consideration of sequence alignment methods and homology calculations. The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Sequence identity between polypeptide sequences is preferably determined by pairwise alignment algorithm using the Needleman-Wunsch global alignment algorithm (Needleman and Wunsch, A General Method Applicable to the Search for Similarities in the Amino Acid Sequence of Two Proteins, 1970 J. Mol. Biol. 48(3): 443-453), using default parameters (e.g. with Gap opening penalty=10.0, and with Gap extension penalty=0.5, using the EBLOSUM62 scoring matrix). This algorithm is conveniently implemented in the needle tool in the EMBOSS package (Rice et al., EMBOSS: The European Molecular Biology Open Software Suite, 2000 Trends Genetics 16: 276-277). Sequence identity should be calculated over the entire length of the polypeptide sequence of the invention.

A "subject" is a living multi-cellular vertebrate organism. In the context of this disclosure, the subject can be an experimental subject, such as a non-human mammal, e.g., a mouse, a cotton rat, or a non-human primate. Alternatively, the subject can be a human subject.

An "antigen" is a compound, composition, or substance that can stimulate an immune response by producing antibodies and/or a T cell response in a mammal, including compositions that are injected, absorbed or otherwise introduced into a mammal. The term "antigen" includes all related antigenic epitopes. The term "epitope" or "antigenic determinant" refers to a site on an antigen to which B and/or T cells respond. The "predominant antigenic epitopes" are those epitopes to which a functionally significant host immune response, e.g., an antibody response or a T-cell response, is made. Thus, with respect to a protective immune response against a pathogen, the predominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"), such as an HCMV antigen. If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

Typically, the immune response elicits an immune response characterized by the production of Th1 type cytokines, e.g. a Th1-type immune response. A "Th1" type immune response is characterized CD4+T helper cells that produce IL-2 and IFN-γ. In contrast, a "Th2" type immune response is characterized by CD4+ helper cells that produce IL-4, IL-5, and IL-13.

An "effective amount" means an amount sufficient to cause the referenced effect or outcome. An "effective amount" can be determined empirically and in a routine manner using known techniques in relation to the stated purpose. An "immunologically effective amount" is a quantity of a composition (typically, an immunogenic composition) sufficient to elicit an immune response in a subject (either in a single dose or in a series). Commonly, the desired result is the production of an antigen (e.g., pathogen)-specific immune response that is capable of or contributes to protecting the subject against the pathogen, such as HCMV. However, to obtain a protective immune response against a pathogen can require multiple administrations of the immunogenic composition. Thus, in the context of this disclosure, the term immunologically effective amount encompasses a fractional dose that contributes in combination with previous or subsequent administrations to attaining a protective immune response.

Also provided are immunogenic compositions or pharmaceutical compositions, such as vaccines, that comprise a modified HCMV gB protein and a pharmaceutically acceptable diluent, carrier or excipient. An "immunogenic composition" is a pharmaceutical composition of matter suitable for administration to a human or non-human mammalian subject that is capable of eliciting a specific immune response, e.g., against a pathogen, such as HCMV. As such, an immunogenic composition includes one or more antigens (for example, polypeptide antigens or an RNA or DNA that encodes a polypeptide antigen) or antigenic epitopes, such as for instance, the modified HCMV gB protein of the inventions. An immunogenic composition can also include one or more additional components capable of enhancing an immune response, such as an excipient, carrier, and/or adjuvant.

In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., HCMV) following exposure of the subject to the pathogen. In the context of this disclosure, the term immunogenic composition will be understood to encompass compositions that are intended for administration to a subject or population of subjects for the purpose of eliciting a protective or palliative immune response against HCMV.

The immunogenic compositions according to the invention are not limited to compositions consisting of modified HCMV gB proteins. The present invention also contemplates immunogenic compositions, such as vaccines, comprising the modified HCMV gB protein of the invention and at least one or more HCMV antigens. Such one or more HCMV antigens may be pp65, IE1, gO, gL, gH, pUL128, pUL130, pUL131, or any combination thereof, or any complex-forming fragment thereof. As an example, a composition comprising a modified HCMV gB protein as described herein and pp65 is contemplated. Further, a composition comprising a modified protein as described herein and IE1 is contemplated. Further, a composition comprising a modified HCMV gB protein as described herein and gL, gH, pUL128, pUL130, and pUL131 is contemplated. It is contemplated that the compositions herein may comprise one or more nucleic acids (e.g., an RNA) that together encode a modified HCMV gB protein as described herein and one or more of a gO, gL, gH, pUL128, pUL130, pUL131, pp65, or IE1 protein (e.g., encode a HCMV gO, gL, gH, pUL128, pUL130, pUL131, pp65, or IE1 protein). By "complex-forming fragment" it is meant any part or portion of the polypeptide that retains the ability to form a complex (e.g., the pentameric complex, gH/gL dimer, and gH/gL/gO trimer) with other polypeptides of the complex. As used herein, a "complex-forming fragment" of a modified protein comprises the one or more modified amino acid residues (i.e., the fragment of a modified protein comprises the modification(s)). Where the composition comprises gL, gH, pUL128, pUL130, or pUL131 (five proteins that together form what is called a "pentamer complex"), a "pentamer-forming" fragment of gL, gH, pUL128, pUL130, or pUL131 may be utilized (see WO 2014/005959 (corresponding to U.S. Pat. No. 9,683,022); WO2016/116904 (corresponding to U.S. Pat. No. 10,167,321); and WO 2018/193307). Wherein the composition comprises gH (e.g., HCMV gH), the gH may be a complex-forming fragment that lacks a transmembrane domain (see WO 2014/005959 (corresponding to U.S. Pat. No. 9,683,022). Wherein the composition comprises gL (e.g., HCMV gL), the gL may be a modified gL protein having a modification within a protease recognition site, e.g., a modification within a protease recognition site that reduces protease cleavage of gL (see WO2016/116904 (corresponding to U.S. Pat. No. 10,167,321)). Wherein the composition comprises one or more HCMV gL, gH, pUL128, pUL130, or pUL131 proteins; such one or more HCMV proteins may comprise one or more stabilizing modification as previously disclosed within WO 2018/193307.

Numerous pharmaceutically acceptable diluents and carriers and/or pharmaceutically acceptable excipients are known in the art and are described, e.g., in Remington's Pharmaceutical Sciences, by E. W. Martin, Mack Publishing Co., Easton, Pa., 15th Edition (1975). The adjective "pharmaceutically acceptable" indicates that the diluent, or carrier, or excipient, is suitable for administration to a subject (e.g., a human or non-human mammalian subject). In general, the nature of the diluent, carrier and/or excipient will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. In certain formulations (for example, solid compositions, such as powder forms), a liquid diluent is not employed. In such formulations, non-toxic solid carriers can be used, including for example, pharmaceutical grades of trehalose, mannitol, lactose, starch or magnesium stearate. Suitable carriers are typically large, slowly metabolized macromolecules such as proteins (e.g., nanoparticles), polysaccharides, polylactic acids, polyglycolic acids, polymeric amino acids, amino acid copolymers, lipid aggregates (such as oil droplets or liposomes), and inactive virus particles. Such carriers are well known in the art.

Accordingly, suitable excipients and carriers can be selected by those of skill in the art to produce a formulation suitable for delivery to a subject by a selected route of administration. Excipients include, without limitation: glycerol, polyethylene glycol (PEG), glass forming polyols (such as, sorbitol, trehalose)N-lauroylsarcosine (e.g., sodium salt), L-proline, non detergent sulfobetaine, guanidine hydrochloride, urea, trimethylamine oxide, KCl, Ca2+, Mg2+, Mn2+, Zn2+(and other divalent cation related salts), dithiothreitol (DTT), dithioerytrol, R-mercaptoethanol, detergents (including, e.g., TWEEN 80, TWEEN 20, TRITON X-100, NP-40, EMPIGEN BB, Octylglucoside, Lauroyl maltoside, ZWITTERGENT 3-08, ZWITTERGENT 3-10, ZWITTERGENT 3-12, ZWITTERGENT 3-14, ZWITTERGENT 3-16, CHAPS, sodium deoxycholate, sodium dodecyl sulphate, and cetyltrimethylammonium bromide.

In certain embodiments, the antigen(s) may be conjugated to a bacterial toxoid, such as a toxoid from diphtheria, tetanus, cholera, *H. pylori*, or another pathogen.

In certain examples, the modified HCMV gB protein is operably linked to a carrier wherein the carrier is a nanoparticle. Pharmaceutically acceptable nanoparticles as carriers as well as methods of using them to present an antigen (e.g., present an antigen on the surface of the nanoparticle) are known and include ferritin or lumazine synthase nanoparticles or nanoparticles derived therefrom (see WO 2005/121330 (corresponding to U.S. Pat. No. 8,685,670); WO 2013/044203 (corresponding to U.S. Pat. No. 10,137,190); and WO 2016/037154). Such nanoparticles may be "self-assembling" (see WO 2015/048149 (corresponding to US 2015/0110825)). Nanoparticles operably linked to an antigen in pre-fusion conformation has been demonstrated for RSV F proteins (U.S. Pat. No. 9,738,689).

The pharmaceutical formulations are conventionally administered parenterally, e.g., by injection, either subcutaneously, intraperitoneally, transdermally, or intramuscularly. Some embodiments will be administered through an intramucosal route such as intra-orally, intra-nasally, intra-vaginally, and intra-rectally. Additional formulations suitable for other modes of administration include oral and pulmonary formulations, suppositories, and transdermal applications. Oral formulations may be preferred for certain viral proteins. Dosage treatment may be a single dose schedule or a multiple dose schedule. The immunogenic composition may be administered in conjunction with other immunoregulatory agents. Any suitable route of administration can be used. For example, a composition can be administered intramuscularly, intraperitoneally, subcutaneously, or transdermally. Compositions can be administered according to any suitable schedule.

Typically, the pharmaceutical formulations are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

In certain examples, the immunogenic composition also includes an adjuvant. Suitable adjuvants for use in immunogenic compositions containing modified HCMV gB proteins of the invention are adjuvants that in combination with said polypeptides disclosed herein are safe and having acceptable reactogenicity when administered to a subject.

An "adjuvant" is an agent that enhances the production of an immune response in a non-specific manner. Common adjuvants include suspensions of minerals (alum, aluminum hydroxide, aluminum phosphate) onto which antigen may be adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll Receptor agonists (particularly, TLR2, TLR4, TLR7/8 and TLR9 agonists), and various combinations of such components. In certain embodiment, the adjuvant is a TLR7 agonist, such as imidazoquinoline or imiquimod. In certain embodiment, the adjuvant is an aluminum salt, such as aluminum hydroxide, aluminum phosphate, aluminum sulfate. The adjuvants described herein can be used singularly or in any combination, such as alum/TLR7 agonist combination.

Suitable adjuvants for use in combination with the modified gB proteins of the invention are saponins. Accordingly, immunogenic compositions of the invention may comprise the saponin QS21 (WO8809336A1; U.S. Pat. No. 5,057,540A). QS21 is well known in the art as a natural saponin derived from the bark of Quillaja *saponaria* Molina, which induces CD8+ cytotoxic T cells (CTLs), Th1 cells and a predominant IgG2a antibody response. For the avoidance of doubt reference to QS21 includes OPT-821. In a suitable form of the present invention, the immunogenic compositions of the invention comprise QS21 in substantially pure form, that is to say, the QS21 is at least 80%, at least 85%, at least 90% pure, for example at least 95% pure, or at least 98% pure.

The immunogenic compositions comprising the modified HCMV gB proteins of the invention may comprise QS21 and a sterol, cholesterol in particular. Such compositions show a decreased reactogenicity when compared to compositions in which the sterol is absent, while the adjuvant effect is maintained. Reactogenicity studies may be assessed according to the methods disclosed in WO 96/33739. Suitably the sterol is associated to the saponin adjuvant as described in WO 96/33739. In a particular embodiment, the cholesterol is present in excess to that of QS21, for example, the ratio of QS21:sterol will typically be in the order of 1:100 to 1:1 (w/w), suitably between 1:10 to 1:1 (w/w), and preferably 1:5 to 1:1 (w/w). In particular, the ratio of QS21:sterol being at least 1:2 (w/w). In a particular embodiment, the ratio of QS21:sterol is 1:5 (w/w). Suitable sterols include β-sitosterol, stigmasterol, ergosterol, ergocalciferol and cholesterol. In one particular embodiment, the compositions of the invention comprise cholesterol as sterol. These sterols are well known in the art, for example cholesterol is disclosed in the Merck Index, 11th Edn, page 341, as a naturally occurring sterol found in animal fat. Accordingly, in a specific embodiment, immunogenic compositions comprising the modified modified gB proteins of the invention comprise QS21 in its less reactogenic composition where it is quenched with a sterol, such as cholesterol for example. Several particular forms of less reactogenic compositions wherein QS21 is quenched with a cholesterol exist. In a specific embodiment, the saponin/sterol is in the form of a liposome structure (WO 96/337391). Thus, for example, modified HCMV gB proteins of the invention can suitably be employed in immunogenic compositions with an adjuvant comprising a combination of QS21 and cholesterol.

The term "liposome(s)" generally refers to uni- or multilamellar (particularly 2, 3, 4, 5, 6, 7, 8, 9, or 10 lamellar depending on the number of lipid membranes formed) lipid structures enclosing an aqueous interior. Liposomes and liposome formulations are well known in the art. Lipids, which are capable of forming liposomes include all substances having fatty or fat-like properties. Lipids which can make up the lipids in the liposomes can be selected from the group comprising of glycerides, glycerophospholipids, glycerophosphinolipids, glycerophosphonolipids, sulfolipids, sphingolipids, phospholipids, isoprenolides, steroids, stearines, sterols, archeolipids, synthetic cationic lipids and carbohydrate containing lipids. Liposomes may suitably comprise a phospholipid. Suitable phospholipids include (but are not limited to): phosphocholine (PC) which is an intermediate in the synthesis of phosphatidylcholine; natural phospholipid derivates: egg phosphocholine, egg phosphocholine, soy phosphocholine, hydrogenated soy phosphocholine, sphingomyelin as natural phospholipids; and synthetic phospholipid derivates: phosphocholine (didecanoyl-L-α-phosphatidylcholine [DDPC], dilauroylphosphatidylcholine [DLPC], dimyristoylphosphatidylcholine [DMPC], dipalmitoyl phosphatidylcholine [DPPC], distearoyl phosphatidylcholine [DSPC], dioleoyl phosphatidylcholine [DOPC], 1-palmitoyl, 2-oleoylphosphatidylcholine [POPC], dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-d istearoyl-sn-g lycero-3-phosphoethanolamine DSPE 1,2-Dioleoyl-sn-Glycero-3-Phosphoethanolamine [DOPE]), phoshoserine, polyethylene glycol [PEG] phospholipid (mPEG-phospholipid, polyglycerin-phospholipid, funcitionilized-phospholipid, terminal activated-phosholipid). In one embodiment the liposomes comprise 1-palmitoyl-2-oleoyl-glycero-3-phosphoethanolamine. In one embodiment highly purified phosphatidylcholine is used and can be selected from the group comprising phosphatidylcholine (Egg), phosphatidylcholine hydrogenated (Egg) phosphatidylcholine (Soy) phosphatidylcholine hydrogenated (Soy). In a further embodiment the liposomes comprise phosphatidylethanolamine [POPE] or a derivative thereof. Liposome size may vary from 30 nm to several µm depending on the phospholipid composition and the method used for their preparation. In particular embodiments of the invention, the liposome size will be in the range of 50 nm to 500 nm and in further embodiments 50 nm to 200 nm. Dynamic laser light scattering is a method used to measure the size of liposomes well known to those skilled in the art. Liposomes of the invention may comprise dioleoyl phosphatidylcholine [DOPC] and a sterol, in particular cholesterol. Thus, in a particular embodiment, immunogenic compositions comprising the modified HCMV gB proteins of the invention, comprise QS21 in the form of a liposome, wherein said liposome comprises dioleoyl phosphatidylcholine [DOPC] and a sterol, in particular cholesterol.

Immunogenic compositions of the invention may comprise one or more further immunostimulants. In one embodiment, immunogenic compositions comprising the modified HCMV gB proteins of the invention as described herein further comprise a lipopolysaccharide, suitably a non-toxic derivative of lipid A, particularly monophosphoryl lipid A or more particularly 3-Deacylated monophoshoryl lipid A (3D-MPL). 3D-MPL is sold under the name MPL by GlaxoSmithKline Biologicals and is referred throughout the specification as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL can be used. Small particle 3D-MPL has a particle size such that it can be sterile-filtered through a 0.22 µm filter. Such preparations are described in WO94/21292.

In other embodiments, the lipopolysaccharide can be a β1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. In addition to the described immunostimulants (that are similar in structure to that of LPS or MPL or 3D-MPL), acylated monosaccharide and disaccharide derivatives that are a sub-portion to the above structure of MPL are also suitable adjuvants. In other embodiments, the adjuvant is a synthetic derivative of lipid A, some of which are described as TLR-4 agonists (see WO 95/14026; WO 99/64301 and WO 00/0462; WO 01/46127).

Combinations of different adjuvants, such as those mentioned hereinabove, can also be used in compositions with modified HCMV gB proteins. For example, as already noted, QS21 can be formulated together with 3D-MPL. The ratio of QS21: 3D-MPL will typically be in the order of 1:10 to 10:1; such as 1:5 to 5:1, and often substantially 1:1. Typically, the ratio is in the range of 2.5:1 to 1:1 3D-MPL: QS21. Accordingly, in some embodiments, immunogenic compositions comprising modified gB proteins of the invention comprise at least QS21 and 3D-MPL.

The immunogenic compositions comprising the modified HCMV gB proteins of the invention may also be suitably formulated with an oil-in-water emulsion. The oil in water emulsion comprises a metabolisable oil (i.e. biodegradable). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also suitable. Accordingly, oil-in-water emulsions used in combination with the modified HCMV gB proteins of the invention comprise a metabolisable oil. In a particular embodiment, oil-in-water emulsions comprise squalene (for example between about 4% and 6% [v/v]). The oil-in-water emulsion may further comprise a surfactant. Oil-in-water emulsions of the invention comprise one or more surfactants. Suitable surfactants are well known to the skilled person and include, but are not limited to, polyoxyethylene sorbitan monooleate (TWEEN 80, Polysorbate 80), sorbitan triolate (SPAN 85), phosphatidylcholine (lecithin), polyoxyethylene (12) cetostearyl ether and octoxynol-9 (TRITON X-100). In a particular embodiment of the invention, oil-in-water emulsions comprise is polyoxyethylene sorbitan monooleate (TWEEN 80, Polysorbate 80). In a further embodiment, oil in water emulsions of the invention comprise polyoxyethylene sorbitan monooleate (TWEEN 80) and a further surfactant, in particular sorbitan trioleate (SPAN 85). Oil-in-water emulsions of the invention may also comprise a tocol. Tocols are well known in the art and are described in EP0382271. In particular, the tocol is α-tocopherol or a derivative thereof such as alpha-tocopherol succinate (also known as vitamin E succinate). In a particular embodiment of the invention, there is provided immunogenic compositions comprising the modified gB protein of the invention in combination with an oil-in-water emulsion comprising squalene (for example about 5% [v/v]) and α-tocopherol (for example about 5% [v/v]). In a particular embodiment, the oil-in-water emulsion comprises a metabolisable oil (e.g. squalene), a tocol (e.g. α-tocopherol) and a surfactant (e.g. polyoxyethylene sorbitan monooleate [Polysorbate 80]). In a further embodiment of the invention, oil-in-water emulsions of the invention comprise a metabolisable oil (e.g. squalene), a surfactant (e.g. polyoxyethylene sorbitan monooleate [Polysorbate 80]), and optionally a second surfactant (e.g. sorbitan trioleate [SPAN 85]). In a further embodiment of the invention, oil-in-water emulsions of the invention comprise a metabolisable oil (e.g. squalene), a polyoxyethylene alkyl ether hydrophilic non-ionic surfactant (e.g. polyoxyethylene (12) cetostearyl ether) and a hydrophobic non-ionic surfactant (e.g. polyoxyethylene sorbitan monooleate [Polysorbate 80]), or sorbitan trioleate [SPAN 85]). In some embodiments, immunogenic compositions comprise an oil-in-water emulsion comprising squalene, alpha-tocopherol, and Polysorbate 80.

Suitably, the oil-in-water comprises 11 mg metabolisable oil (such as squalene) or below, for example between 0.5-11 mg, 0.5-10 mg or 0.5-9 mg 1-10 mg, 1-11 mg, 2-10 mg, 4-8 mg, or 4.5-5.5 mg, and 5 mg emulsifying agent (such as polyoxyethylene sorbitan monooleate) or below, for example between 0.1-5 mg, 0.2-5 mg, 0.3-5 mg, 0.4-5 mg, 0.5-4 mg, 1-2 mg ort-3 mg per dose of the vaccine. Suitably tocol (e.g. alpha-tocopherol) where present is 12 mg or below, for example between 0.5-12 mg, 10-11 mg, 1-11 mg, 2-10 mg, 4-9 mg, or 5-7 mg per human vaccine dose. By the term "vaccine human dose" is meant a dose which is in a volume suitable for human use. Generally, this is between 0.25 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the pediatric population, a human dose may be less than 0.5 ml such as between 0.25 and 0.5 ml.

An immunogenic composition typically contains an immunoprotective quantity (or a fractional dose thereof) of the antigen and can be prepared by conventional techniques. Preparation of immunogenic compositions, such as vaccines, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of protein in each dose of the immunogenic composition is selected as an amount which induces an immunoprotective response without significant, adverse side effects in the typical subject.

Immunoprotective in this context does not necessarily mean completely protective against infection; it means protection against symptoms or disease, especially severe disease associated with the virus. The amount of antigen can vary depending upon which specific immunogen is employed. The amount utilized in an immunogenic composition is selected based on the subject population (e.g., infant or elderly). An optimal amount for a particular composition can be ascertained by standard studies involving observation of antibody titres and other responses in subjects. Following an initial vaccination, subjects can receive a boost in about four weeks.

In some embodiments, modified HCMV gB proteins (or immunogenic fragments thereof) and/or one or more additional immunogenic protein (e.g., HCMV antigen) described herein are delivered using alphavirus replicon particles (VRP). As used herein, the term "alphavirus" has its conventional meaning in the art and includes various species such as Venezuelan equine encephalitis virus (VEE; e.g., Trinidad donkey, TC83CR, etc.), Semliki Forest virus (SFV), Sindbis virus, Ross River virus, Western equine encephalitis virus, Eastern equine encephalitis virus, Chikungunya virus, S.A. AR86 virus, Everglades virus, Mucambo virus, Barmah Forest virus, Middelburg virus, Pixuna virus, O'nyong-nyong virus, Getah virus, Sagiyama virus, Bebaru virus, Mayaro virus, Una virus, Aura virus, Whataroa virus, Banbanki virus, Kyzylagach virus, Highlands J virus, Fort Morgan virus, Ndumu virus, and Buggy Creek virus.

An "alphavirus replicon particle" (VRP) or "replicon particle" is an alphavirus replicon packaged with alphavirus structural proteins.

An "alphavirus replicon" (or "replicon") is an RNA molecule which can direct its own amplification in vivo in a target cell. The replicon encodes the polymerase(s) which catalyze RNA amplification (nsPI, nsP2, nsP3, nsP4) and contains cis RNA sequences required for replication which are recognized and utilized by the encoded polymerase(s). An alphavirus replicon typically contains the following ordered elements: 5' viral sequences required in cis for replication, sequences which encode biologically active alphavirus nonstructural proteins (nsPI, nsP2, nsP3, nsP4), 3' viral sequences required in cis for replication, and a polyadenylate tract. An alphavirus replicon also may contain one or more viral subgenomic "junction region" promoters directing the expression of heterologous nucleotide sequences, which may, in certain embodiments, be modified in order to increase or reduce viral transcription of the subgenomic fragment and heterologous sequence(s) to be expressed. Other control elements can be used, such as IRES or 2A sequences.

Recombinant nucleic acids that encode the modified HCMV gB proteins or immunogenic fragments described herein can be administered to induce production of the encoded modified gB proteins or immunogenic fragments and an immune response thereto.

The recombinant nucleic acid can be DNA (e.g., plasmid or viral DNA) or RNA, preferably self-replicating RNA, and can be monocistronic or polycistronic. Any suitable DNA or RNA can be used as the nucleic acid vector that carries the open reading frames that encode HCMV gB proteins or immunogenic fragments thereof. Suitable nucleic acid vectors have the capacity to carry and drive expression of one or more modified HCMV gB proteins or immunogenic fragments. Such nucleic acid vectors are known in the art and include, for example, plasmids, DNA obtained from DNA viruses such as vaccinia virus vectors (e.g., NYVAC, see U.S. Pat. No. 5,494,807), adenoviral vectors and poxvirus vectors (e.g., ALVAC canarypox vector, Sanofi Pasteur), and RNA obtained from suitable RNA viruses such as alphavirus. If desired, the recombinant nucleic acid molecule can be modified, e.g., contain modified nucleobases and or linkages as described further herein.

The self-replicating RNA molecules of the invention are based on the genomic RNA of RNA viruses, but lack the genes encoding one or more structural proteins. The self-replicating RNA molecules are capable of being translated to produce non-structural proteins of the RNA virus and modified HCMV gB proteins encoded by the self-replicating RNA.

The self-replicating RNA generally contains at least one or more genes selected from the group consisting of viral replicase, viral proteases, viral helicases and other nonstructural viral proteins, and also comprise 5'- and 3'-end cis-active replication sequences, and a heterologous sequence that encodes one or more desired modified HCMV gB proteins. A subgenomic promoter that directs expression of the heterologous sequence(s) can be included in the self-replicating RNA. If desired, a heterologous sequence may be fused in frame to other coding regions in the self-replicating RNA and/or may be under the control of an internal ribosome entry site (IRES).

Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sindbis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus, the delivered RNA leads to the production of multiple daughter RNAs. These transcripts are antisense relative to the delivered RNA and may be translated themselves to provide in situ expression of encoded HCMV protein, or may be transcribed to provide furthertranscripts with the same sense as the delivered RNA which are translated to provide in situ expression of the encoded HCMV protein(s).

A preferred self-replicating RNA molecule thus encodes (i) a RNA-dependent RNA polymerase which can transcribe RNA from the self-replicating RNA molecule and (ii) one or more modified HCMV gB proteins or immunogenic fragments thereof. The polymerase can be an alphavirus replicase e.g. comprising alphavirus non-structural proteins nsP1-nsP4.

The self-replicating RNA molecules of the invention can contain one or more modified nucleotides and therefore have improved stability and be resistant to degradation and clearance in vivo, and other advantages. There are more than 96 naturally occurring nucleoside modifications found on mammalian RNA. See, e.g., Limbach et al., Nucleic Acids Research, 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated herein by reference in their entirety, and many modified nucleosides and modified nucleotides are commercially available. If desired, the self-replicating RNA molecule can contain phosphoramidate, phosphorothioate, and/or methylphosphonate linkages.

The self-replicating RNA described herein is suitable for delivery in a variety of modalities, such as naked RNA delivery or in combination with lipids, polymers or other compounds that facilitate entry into the cells. Self-replicating RNA molecules can be introduced into target cells or subjects using any suitable technique, e.g., by direct injection, microinjection, electroporation, lipofection, biolistics, and the like. The self-replicating RNA molecule may also be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine amino acids), which is itself coupled to an integrin receptor-binding moiety (e.g., a cyclic peptide having the sequence Arg-Gly-Asp).

The self-replicating RNA molecules can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The self-replicating RNA can be delivered as naked RNA (e.g. merely as an aqueous solution of RNA) but, to enhance entry into cells and also subsequent intercellular effects, the self-replicating RNA is preferably administered in combination with a delivery system, such as a particulate or emulsion delivery system. A large number of delivery systems are well known to those of skill in the art. Three particularly useful delivery systems are (i) liposomes, (ii) non-toxic and biodegradable polymer microparticles, and (iii) cationic submicron oil-in-water emulsions.

The invention also provides immunogenic composition comprising the nucleic acid (e.g., self-replicating RNA) described herein. The immunogenic composition may comprise an adjuvant, as described above. Preferred adjuvants include, e.g., an aluminum salt or an oil-in-water emulsion (such as MF59).

A nucleic acid approach for the prevention or treatment of HCMV using gB protein optionally in combination with other HCMV protein(s) was described previously, e.g., WO 2012/051211 and John et al. 2018 Vaccine 36(12): 1689-1699.

Methods of inducing an immune response against HCMV may comprise the production of neutralizing antibodies against HCMV. In certain embodiments, the neutralizing antibodies are complement-independent. Alternatively, the induced immune response can comprise a humoral immune response, a cell-mediated immune response, or both. In some embodiments an immune response is induced against each delivered HCMV gB protein and, as relevant, other virus antigens having been delivered (e.g., pentamer complex). A cell-mediated immune response can comprise a helper T-cell (Th) response, a CD8+ cytotoxic T-cell (CTL) response, or both. In some embodiments the induced immune response comprises a humoral immune response, and the antibodies are neutralizing antibodies. Neutralizing antibodies block viral infection of cells. With regard to HCMV, the HCMV infects epithelial cells and also fibroblast cells and, in some embodiments the immune response reduces or prevents HCMV infection of both cell types. Neutralizing antibody responses can be complement-dependent or complement-independent. In some embodiments the induced neutralizing antibody response is complement-dependent. In some embodiments the induced neutralizing antibody response is cross-neutralizing; e.g., with regard to HCMV, an antibody generated against an administered composition neutralizes a HCMV virus of one or more strains in addition to the strain used in the composition.

An immune response can be stimulated by administering proteins, DNA molecules, RNA molecules (e.g., self-replicating RNA molecules), or VRPs to an individual subject, typically a mammal, including a human. In some embodiments the immune response induced is a protective immune response, i.e., the response reduces the risk or severity of HCMV infection. Stimulating a protective immune response is particularly desirable in populations particularly at risk for HCMV infection, including solid organ transplant (SOT) patients, bone marrow transplant patients, and hematopoietic stem cell transplant (HSCT) patients. VRPs can be administered to a transplant donor pre-transplant, or a transplant recipient pre- and/or post-transplant. Because vertical transmission of HCMV from mother to child is a common source of infection in infants, administering VRPs to a woman who is pregnant or can become pregnant is particularly useful.

The invention provides a kit for identifying the presence of a modified HCMV gB protein within a composition, for the purification of a modified HCMV gB protein from a composition, or for detecting a modified HCMV gB protein in pre-fusion or non-post-fusion conformation; the kit comprising an antibody or antigen-binding fragment thereof that is specific for the modified HCMV gB protein. The invention further provides a pharmaceutical kit for the prevention or treatment of HCMV virus infection comprising a pharmaceutical composition comprising an effective amount of an antibody or antigen-binding fragment thereof that is specific for a modified HCMV gB protein as described herein. The kit also contains instructions for using the antibody or antigen-binding fragment thereof for identifying the presence of a modified HCMV gB protein within a composition, for the purification of a modified HCMV gB protein from a composition, or for the prevention or treatment of HCMV infection. The kit may also contain excipients, diluents, adjuvants, syringes, other appropriate means of administering the antibody or antigen-binding fragment thereof, or instructions for decontamination or disposal.

By "adjacent", it is meant "next to" or "side-by-side". By "immediately adjacent", it is meant adjacent to with no material structures in between (e.g., in the context of an amino acid sequence, two residues being "immediately adjacent" to each other means there are atoms between the two residues sufficient to form the bonds necessary for a polypeptide sequence, but not a third residue (a third residue being a "material structure" in that context)).

By "c-terminally" or "c-terminal" to, it is meant toward the c-terminus. Therefore, by "c-terminally adjacent" it is meant "next to" and on the c-terminal side (i.e., on the right side if reading from left to right).

By "n-terminally" or "n-terminal" to, it is meant toward the n-terminus. Therefore, by "n-terminally adjacent" it is meant "next to" and on the n-terminal side (i.e., on the left side if reading from left to right).

By "truncated" it is meant cut short, e.g., "truncated after residue 724" herein means the amino acid sequence comprises residue 724, but the residues c-terminal thereto (i.e., 725->-C) have been deleted. Optionally, the c-terminal (or 3'-end) of a truncated protein or polynucleotide (respectively) may be extended by operably linking it to another (heterologous) amino acid or nucleic acid sequence. In this way, the location of truncation does not always correspond with the c-terminal end (or 3' end) of the sequence. If a gB protein or polynucleotide is "truncated" herein it is generally meant that the gB protein or polynucleotide is truncated as compared to a wild type or control gB protein or polynucleotide (i.e., it is the native amino acids or nucleic acids, found within a wild type gB protein or polynucleotide, which have been deleted).

"Operably linked" means connected so as to be "operational", for example, the configuration of polynucleotide sequences for recombinant protein expression. In certain embodiments, "operably linked" refers to the art-recognized positioning of, e.g., nucleic acid components such that the intended function (e.g., expression) is achieved. A person with ordinary skill in the art will recognize that under certain circumstances (e.g., a cleavage site or purification tag), two or more components "operably linked" together are not necessarily adjacent to each other in the nucleic acid or amino acid sequence. A coding sequence that is "operably linked" to a "control sequence" (e.g., a promoter, enhancer, or IRES) is ligated in such a way that expression of the coding sequence is under the influence or control of the control sequence, but it would be recognized in the art that such a ligation is not limited to adjacent ligation. Further, and by example, it would be understood that to construct an HCMV gB amino acid sequence into which a heterologous amino acid sequence has been inserted, the heterologous sequence must be operably linked to the native HCMV gB amino acids (likewise the polynucleotide sequence encoding the heterologous sequence must be operably linked to the polynucleotide sequence encoding the native HCMV gB amino acids). A person with ordinary skill in the art will recognize that a variety of configurations are functional and encompassed.

The singular terms "a", "an", and "the" include plural referents unless context clearly indicates otherwise. The term "plurality" refers to two or more.

The terms "about" or "approximately" mean roughly, around, or in the regions of. The terms "about" or "approximately" further mean within an acceptable contextual error range for the particular value as determined by one of ordinary skill in the art, which will depend in part on how the value is measured or determined, i.e. the limitations of the measurement system or the degree of precision required for a particular purpose, e.g. the amount of a complex within media. When the terms "about" or "approximately" are used in conjunction with a numerical range, it modifies that range by extending the boundaries above and below the numerical values set forth. For example, "between about 5.5 to 6.5 mg/ml" means the boundaries of the numerical range extend below 5.5 and above 6.5 so that the particular value in question achieves the same functional result as within the range. For example, "about" and "approximately" can mean within one or more than one standard deviation as per the practice in the art. Alternatively, "about" and "approximately" can mean a range of up to 20%, preferably up to 10%, more preferably up to 5%, and more preferably up to 1% of a given value.

It is further to be understood that all base sizes or amino acid sizes, and all molecular weight or molecular mass values, given for nucleic acids or polypeptides are approximate and are provided for description. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "—") 200 pg.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specifically stated, a process comprising a step of mixing two or more components does not require any specific order of mixing. Thus, components can be mixed in any order.

Where there are three components then two components can be combined with each other, and then the combination may be combined with the third component, etc. Similarly, while steps of a method may be numbered (such as (1), (2), (3), etc. or (i), (ii), (iii)), the numbering of the steps does not mean that the steps must be performed in that order (i.e., step 1 then step 2 then step 3, etc.). The word "then" may be used to specify the order of a method's steps.

Although methods and materials similar or equivalent to those described herein can be used in the practice or testing of this disclosure, suitable methods and materials are described below. The term "comprises" means "includes". Thus, unless the context requires otherwise, the word "comprises", and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or group thereof. The abbreviation, "e.g." is derived from the Latin exempli gratia, and is used herein to indicate a non-limiting example. Thus, the abbreviation "e.g." is synonymous with the term "for example."

This invention is further illustrated by the following examples which should not be construed as limiting.

EXAMPLES

Example 1

HCMV Merlin strain gB (SEQ ID NO: 1 and UniProtKB Accession No. F5HB53) was modified with previously described furin cleavage site modifications to reduce processing during protein expression (Chandramouli et al. 2015 Nat. Comm. 6(8176): 1-12; Burke & Heldwein 2015 PLOS Path. DOI: 10.1371; see also WO 2012/049317 (corresponding to US 2013/0216613); and WO 2016/092460 (corresponding to US 2018/0265551). In particular, residue R457 (numbered per SEQ ID NO: 1) was substituted to serine (R457S) and residue R460 (numbered per SEQ ID NO: 1) was substituted to serine (R460S). To prevent aggregation, Fusion Loop 1 (FL1) and Fusion Loop 2 (FL2) (corresponding to residues 155-157 and 240-242, respectively, of SEQ ID NO: 1) were modified as previously described: hydrophobic residues within FL1 or FL2 were replaced with their (generally) more hydrophilic HSV-1 counterparts (Burke & Heldwein 2015 PLOS Path. DOI: 10.1371; see also WO 2012/049317 (corresponding to US 2013/0216613); and WO 2016/092460 (corresponding to US 2018/0265551)). In particular, the following substitutions were made (numbered per SEQ ID NO: 1) Y155G, I156H, H157R, W240A, L241F, and Y242H. A HCMV Merlin strain gB having such furin cleavage site and fusion loops modifications forms a trimer and has post-fusion conformation (see Chandramouli et al. 2015 Nat. Comm. 6:8176).

HCMV Merlin strain gB molecules having the above furin cleavage site modifications (R457S and R460S) and the above FL1 and FL2 modifications (Y155G, I156H, H157R, W240A, L241F, and Y242H) are referred to herein as "gB'2" or 'gB prime 2'.

HCMV AD169 strain gB (SEQ ID NO: 6) was modified to contain the furin cleavage site modifications and fusion loop modifications corresponding to those in HCMV Merlin strain gB'2. The resulting modified HCMV AD169 gB molecules are referred to herein as "g B'1" or 'gB prime one'.

GCN4 Leucine Zipper domain operably linked to truncated MPR

The gB'2 molecule as described above was further modified to provide gB'-GCN4 (SEQ ID NO: 3) by: truncation of the residues C-terminal to MPR residue K724 (MPR corresponds to residues D699-P751 (inclusive) of SEQ ID NO: 1); insertion of two proline residues C-terminally adjacent to residue K724; and addition of the General Control Nonderepressible (GCN) 4 Leucine Zipper domain in a trimeric oligomerization state ("GCN4" herein) having the sequence SEQ ID NO: 2 (see Protein Data Bank 4DME and Oshaben et al. 2012 Biochem. 51(47): 9581-9591). The GCN4 sequence is placed c-terminally adjacent to the c-terminal-most inserted proline residue. This modified gB molecule is referred to herein as gB'-GCN4 (SEQ ID NO: 3). Such a modified gB molecule can be represented by N'-K724-P-P-GCN4-C'.

For purification purposes, gB'-GCN4 (SEQ ID NO: 3) was further modified by operably linking a TEV-cleavage site and 6×HIS-tag (SEQ ID NO: 5) to the C-terminus of the GCN4 domain, to provide SEQ ID NO: 4 (gB'-GCN4-TEV).

The gB'1, gB'2 and gB'-GCN4 constructs were made and expressed in transiently transfected Expi293 cells. The presence of antigenic domain 5 (AD-5) epitope in gB'1, gB'2, and gB'-GCN4 was confirmed via binding to a neutralizing antibody (see Chandramouli et al. 2015 Nat. Comm. 6(8176): 1-12 regarding AD-5; data not shown).

Figure 3A:
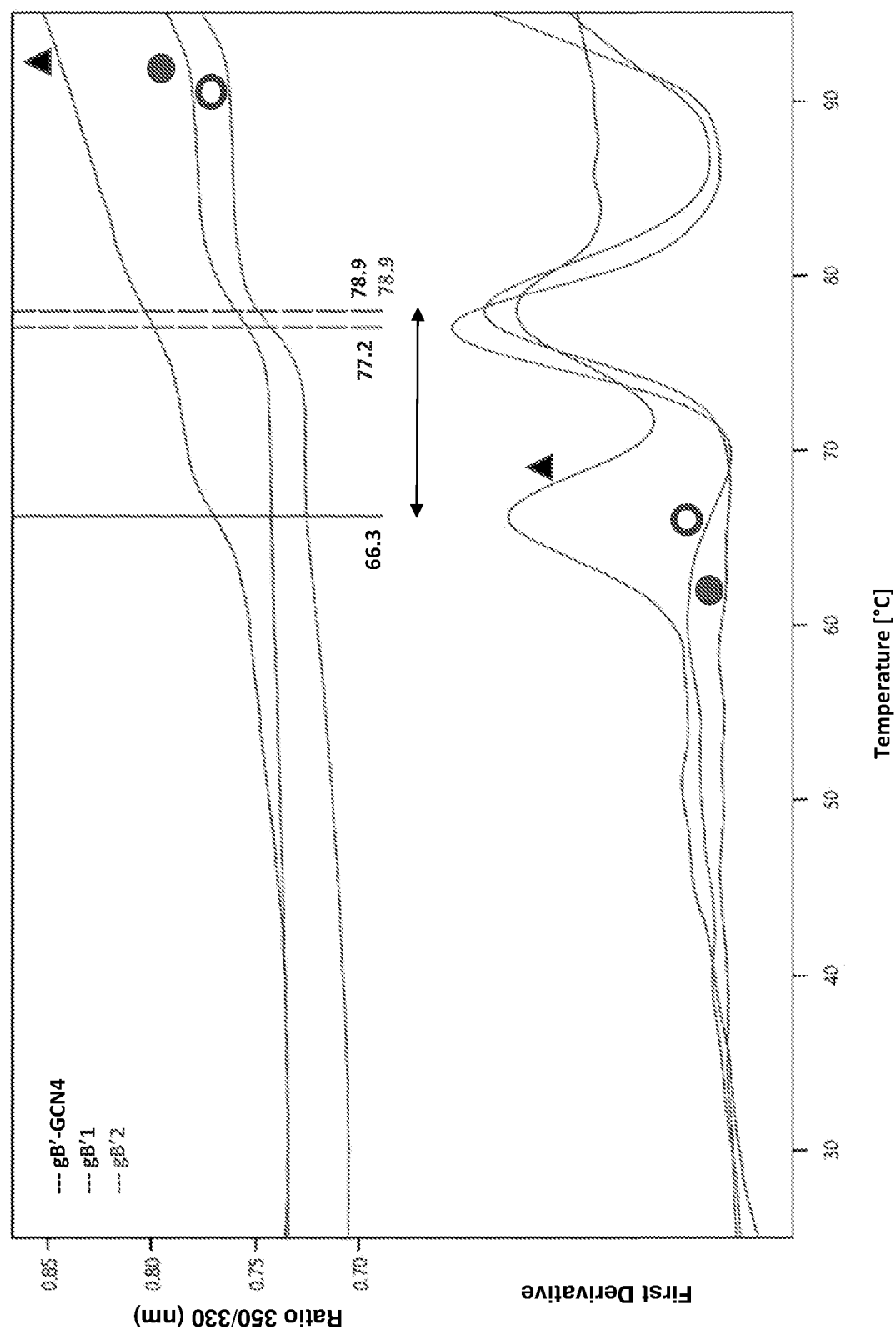
FIG. 3A depicts the results of NanoDSF analysis (raw data and first derivative, Ratio 350 nm/330 nm) conducted on gB'-GCN4 and two gB' proteins (denoted gB'1 and gB'2 therein, which are based on HCMV AD169 strain and Merlin strain, respectively). gB'GCN4 provides two peaks (one at a melting temperature of about 66.3 degrees Celsius and the other at a melting temperature of about 78.9 degrees Celsius) whereas gB'1 only provides one peak (at 77.2 degrees Celsius) and gB'2 only provides one peak (at 78.9 degrees Celsius). The labels on the left side are, from top to bottom, 0.85, 0.80, 0.75, and 0.70, and represent the ratio of the fluorescence signal at 350 nm/330 nm. The temperature (degrees Celsius) labels along the bottom are, from left to right, 30, 40, 50, 60, 70, 80, and 90. Lines corresponding to gB'-GCN4 are indicated by a solid triangle; those corresponding to gB'1 by a solid circle; those corresponding to gB'2 by an open circle.

Nano Differential Scanning Fluorimetry (NanoDSF) analysis was then conducted on gB'1, gB'2, and gB'-GCN4 to determine melting temperatures. Results (FIG. 3A) demonstrate that while gB'1 and gB'2 (each without a GCN4 domain) produce one peak (hereinafter referred to as "peak I"), the gB'-GCN4 molecule produces two peaks (hereinafter referred to as "peak II" and "peak I" from left to right of FIGS. 3A and 3B).

Figure 3B:
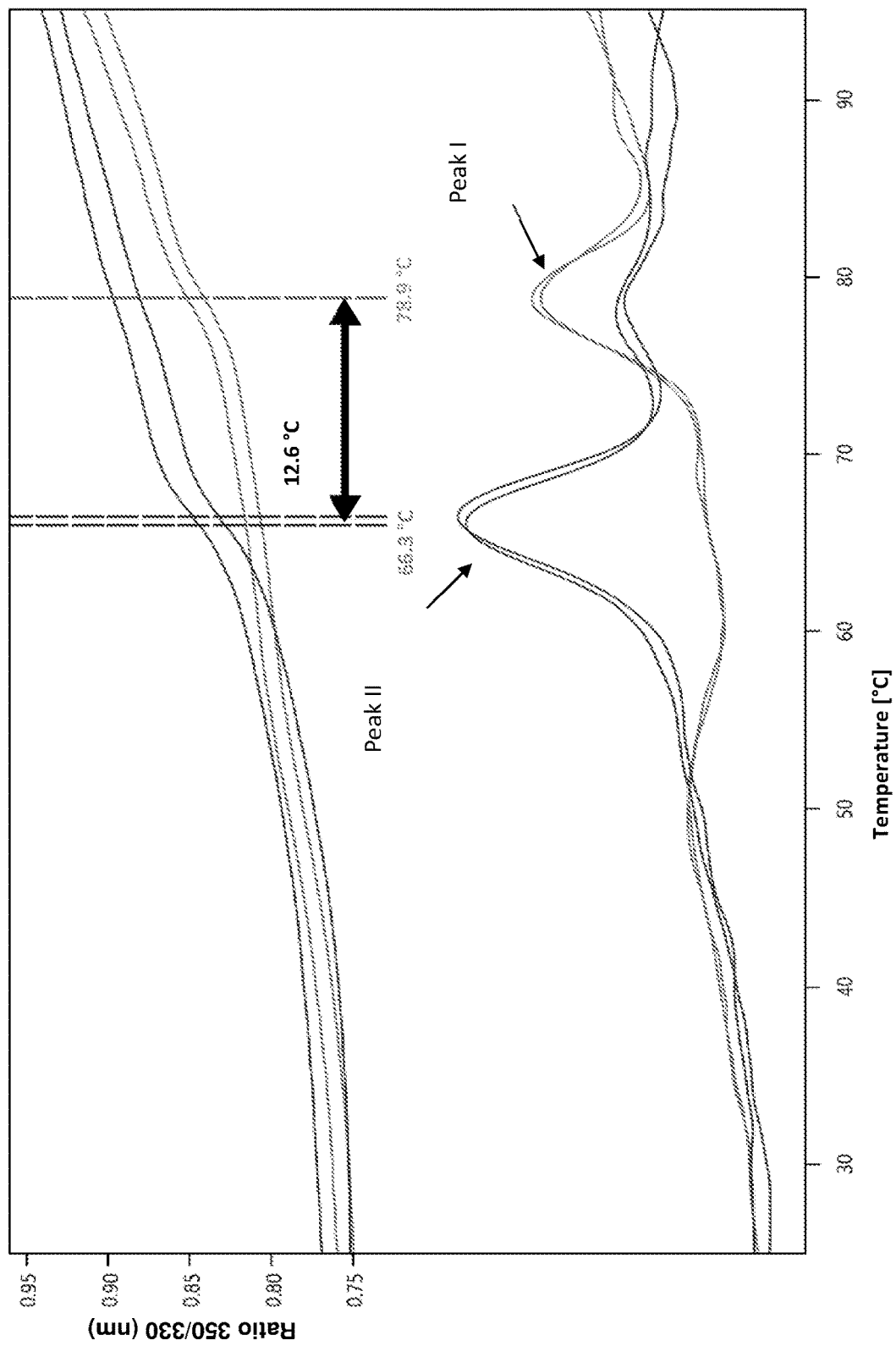
FIG. 3B depicts NanoDSF results for gB'-GCN4 only and confirms that gB'-GCN4 provides two peaks: peak I having a melting temperature of 78.9 degrees Celsius and another, peak II (left-hand peak), having a melting temperature at 66.3 degrees Celsius (12.6 degrees below that of peak I). The labels on the left side are, from top to bottom, 0.95, 0.90, 0.85, 0.80, and 0.75, and represent the ratio of the fluorescence signal at 350 nm/330 nm. The temperature (degrees Celsius) labels along the bottom are, from left to right, 30, 40, 50, 60, 70, 80, and 90.

The inventors confirmed that the molecules at peak I have effectively the same molecular weight as those at peak II, but as is shown in FIG. 3B, peak II molecules have a lower melting temperature (Tm) (left peak) than the molecule at peak I (right peak). Peak I is at a Tm known to correspond to that of post-fusion HCMV gB molecules (data not shown). Negative stain visual inspection revealed that the molecules at peak I have the characteristic post-fusion gB elongated shape whereas the molecules at peak II do not (images not shown). Without wishing to be bound by theory, it is believed that the "non-post-fusion" conformation referred to herein is the "pre-fusion" conformation. These data show that the presence of a trimerization domain, such as a GCN4 domain, C-terminally adjacent to the residue corresponding to K724 of SEQ ID NO: 1, causes a mixed population of gB molecules to be produced, including those in a post-fusion-like conformation (peak I) and those in a non-post-fusion conformation (peak II). The GCN4 domain causes a gB molecule which would otherwise transition to post-fusion conformation (e.g., gB'1, gB'2, or wild type gB), to reside in a non-post-fusion conformation.

Without wishing to be bound by theory, it is believed that the non-post-fusion conformation of the modified gB (gB'-GCN4) revealed through these studies is the pre-fusogenic conformation of gB. Also not wishing to be bound by theory, but based on these results and the knowledge in the art, it is believed that inclusion of the GCN4 Leucine Zipper domain having SEQ ID NO: 2 C-terminally adjacent to the residue corresponding to 724 of SEQ ID NO: 1 in other HCMV gB strains (e.g., AD169 or Towne), will also result in producing a gB protein in non-post-fusion conformation.

Domain III Coiled-Coil (DIIIcc) Region Modifications

Figure 4A:
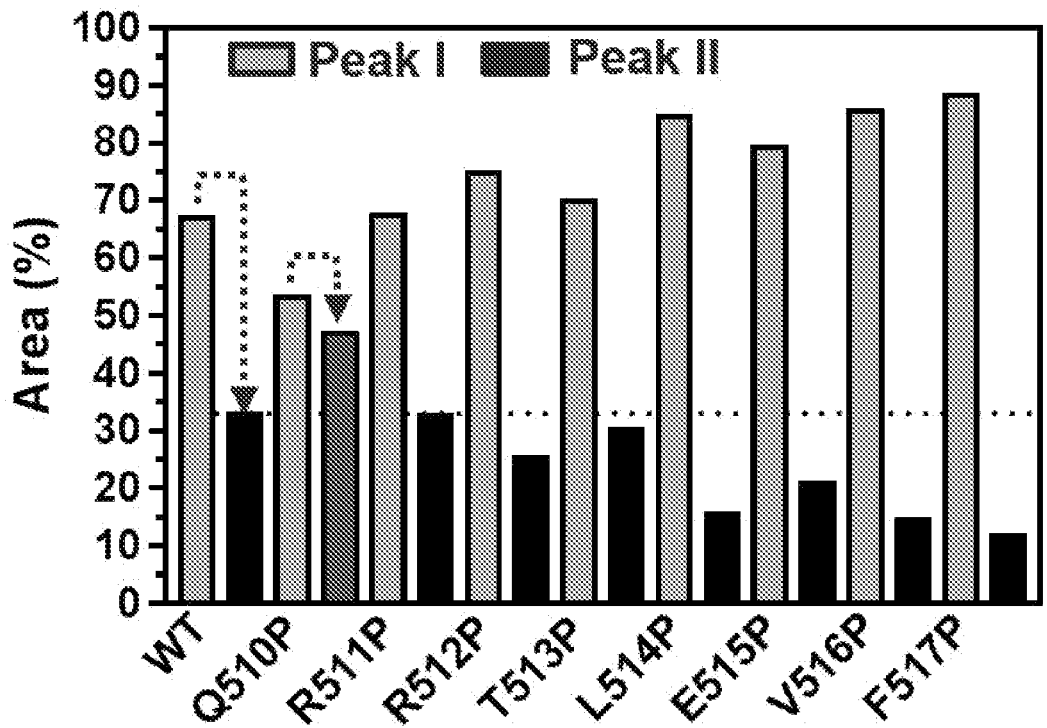
FIG. 4A summarizes, for differently modified gB proteins, what percentage of the modified gB protein had a melting temperature as at peak I and what percentage had a melting temperature as at peak II, determined via the results of SEC-HPLC and NanoDSF analysis. "WT" indicates gB'-GCN4 (SEQ ID NO:3); Q510P, R511P, R512P, T513P, L514P, E515P, V516P, and F517P indicate gB'-GCN4 (SEQ ID NO:3) with the indicated proline substitution (numbered according to SEQ ID NO:1).

The proportion of gB'-GCN4 molecules in non-post-fusion conformation (peak II) to post-fusion-like conformation (peak I) is less than 50%, as shown by the first two columns of FIG. 4A (where gB'-GCN4 is labeled as "WT"). While the GCN4 modification is sufficient to produce a gB molecule in non-post-fusion conformation, it is desirable to increase the proportion (ratio) of non-post-fusion gBs to post-fusion gBs.

Based on the results of proline scanning of the DIIIcc region (see below), it was determined that increasing the ratio of gB in non-post-fusion conformation to gB in post-fusion conformation during gB production could be achieved by further modifying the gB'-GCN4 molecules to comprise one or more proline substitutions of a Domain III Coiled-coil region amino acid ("DIIIcc region"). Specifically, while the Domain III Coiled-coil region of HCMV gB, for example, spans amino acids N478 to 1523 (inclusive) of SEQ ID NO: 1 (see Explanation of Sequences section below for a description of corresponding DIIIcc Region residues within SEQ ID NO: 6), the analysis herein suggests that a proline substitution modification at one or more (e.g., one or two) of the amino acids N478-R511 (inclusive) of SEQ ID NO: 1 will stabilize the modified gB protein (gB'-DIIIcc-GCN4) in non-post-fusion conformation and will therefore drive host cell production towards the non-post-fusion gB conformation and away from the post-fusion gB conformation. Thus, within a production lot, the ratio of non-post-fusion gB to post-fusion gB will increase when at least one proline substitution is made within the residues corresponding to N478-R511 (inclusive) of SEQ ID NO: 1, in a gB molecule having a C-terminus truncation and addition of GCN4 domain as described herein (e.g., gB'-GCN4)).

Proline Scanning of DIIIcc Region

Proline scanning was conducted on the DIIIcc Region of gB'-GCN4 (SEQ ID NO: 3). In particular, nine residues within the DIIIcc Region were independently modified to (substituted with) proline: D509, Q510, R511, R512, T513, L514, E515, V516, and F517 (numbered according to SEQ ID NO: 1). Constructs were made and expressed in transiently transfected Expi293 cells then purified; the following eight molecules were obtained:

(1) gB'-Q510P-GCN4,
(2) gB'-R511P-GCN4,
(3) gB'-R512P-GCN4,
(4) gB'-T513P-GCN4,
(5) gB'-L514P-GCN4,
(6) gB'-E515P-GCN4,
(7) gB'-V516P-GCN4, and
(8) gB'-F517P-GCN4.

(Proline scanning of D509 was inconclusive due to suspected cloning failure). The presence of epitopes was assessed via binding to 1G2 neutralizing antibody. The recombinant HCMV gB molecules ((1)-(8), above) bound to 1G2 antibody, therefore confirming the presence of AD5 epitope and providing further evidence that the recombinant gB molecules described herein are immunogenic (see Chandramouli et al. 2015 Nat. Comm. 6(8176): 1-12 regarding AD-5 and 1G2).

Figure 4B:
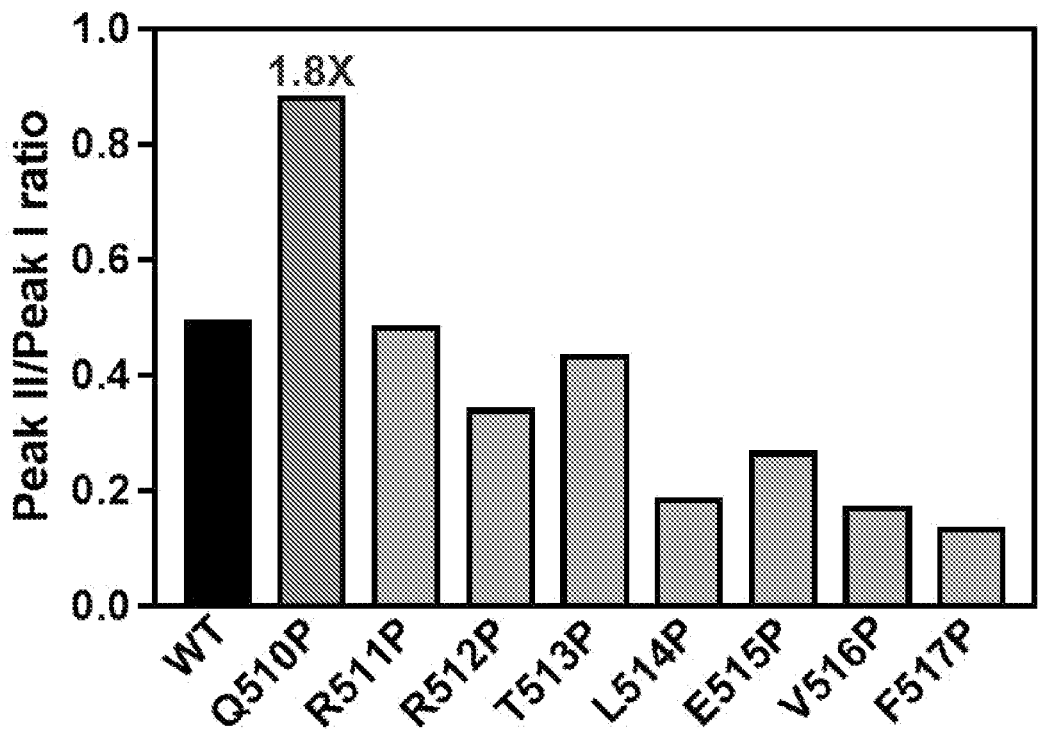
FIG. 4B summarizes the ratio of modified gB proteins having a melting temperature as at peak II to those having a melting temperature as at peak I. "WT" indicates gB'-GCN4 (SEQ ID NO:3); additional proteins indicated as in FIG. 4A.

All of molecules (1)-(8) were subjected to Size Exclusion Chromatography (SEC)-High Performance Liquid Chromatography (HPLC), and NanoDSF analysis (as described above) using gB'-GCN4 (SEQ ID NO: 3) as control. The area below each peak (peak 1 and peak 2) was calculated and is summarized in FIG. 4A. The results show that only gB'-Q510P-GCN4 is able to further stabilize gB'-GCN4 in non-post-fusion conformation (FIGS. 4A and 4B), compared to gB'-GCN4 (indicated as "WT" on FIGS. 4A and 4B). About 35% or less of the population of gB molecules from each the other constructs, including gB'-GCN4 (denoted as wild type (WT) within FIGS. 4A and 4B), were in non-post-fusion conformation (peak II) whereas the gB'-Q510P-GCN4 construct produced a population of gB molecules having at least about 45% of molecules in non-post-fusion conformation (FIG. 4A, columns indicated as 'Q510P')). The ratio of gB molecules in non-post-fusion conformation (peak II) to those in post-fusion-like conformation (peak I) in gB'-Q510P-GCN4 was about 0.9 whereas the ratio in a population of gB'-GCN4 ("WT" in FIG. 4B), gB'-R511P-GCN4, gB'-R512P-GCN4, gB'-T513P-GCN4, gB'-L514P-GCN4, gB'-E515P-GCN4, gB'-V516P-GCN4, or gB'-F517P-GCN4 cells was about 0.5 (FIG. 4B). Therefore, the Q510P substitution being added to a gB-GCN4 construct as described herein increases the yield of gB molecules in non-post-fusion conformation (peak II) by a factor of 1.8 (FIG. 4B).

Structural analysis revealed that the residue Q510 (numbered according to HCMV gB sequence SEQ ID NO: 1) is proximal to a metal ion binding site and a disulfide bridge in the post-fusion structure (FIG. 5). Without wishing to be bound by theory, it is believed that substitution of Q510 (numbered per SEQ ID NO: 1) with proline (or another helix-breaking residue such as G,S, or A), prevents formation of the post-fusion helix in the DIIIcc Region, thereby stabilizing gB'-GCN4 in a non-post-fusion conformation or interfering with the transition to post-fusion conformation. It is further believed that the R511P, R512P, T513P, L514P, E515P, V516P, and F517P substitutions did not further stabilize gB'-GCN4 in non-post-fusion conformation because those residues do not prevent formation of the post-fusion helix in the DIIIcc Region (FIG. 5). From those results, DIIIcc Region residues N478-Q510 (inclusive), specifically N478-W506 and V508-Q510 (inclusive), numbered according to SEQ ID NO: 1 were believed to impact the transition of a gB protein into its post-fusion conformation (but see the further experimental results described below). From these results, a proviso was assumed that the cysteine residue corresponding to C507 (of SEQ ID NO: 1) may be excluded from the DIIIcc residues suitable for further Peak II stabilization by proline substitution because this residue is known to be involved in a structurally significant disulfide bond and, therefore, it was believed that a substitution at this residue may be deleterious to gB production or may not stabilize the gB molecule in a non-post-fusion conformation. But as demonstrated herein below, a C507P substitution surprisingly produces Peak II population at a level similar to gB'-GCN4.

Example 2

Figure 6B:
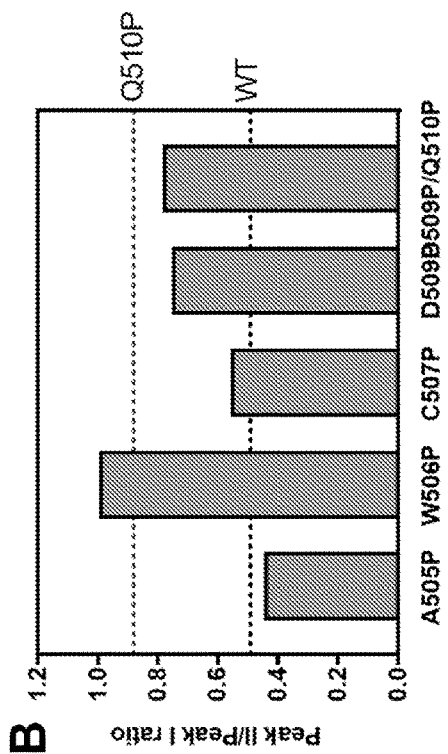
FIG. 6B depicts Peak II/Peak I ratio gB'-A505P-GCN4, gB'-W506P-GCN4, gB'-Q507P-GCN4, gB'-D509P-GCN4, and gB'-D509P-Q510P-GCN4 molecules. Dotted lines indicate the Peak II/Peak I ratio of gB'-GCN4 (designated as "WT" therein) and of the gB'-GCN4-Q510P mutant that is described elsewhere herein (designated as "Q510P" therein).
Figure 6A:
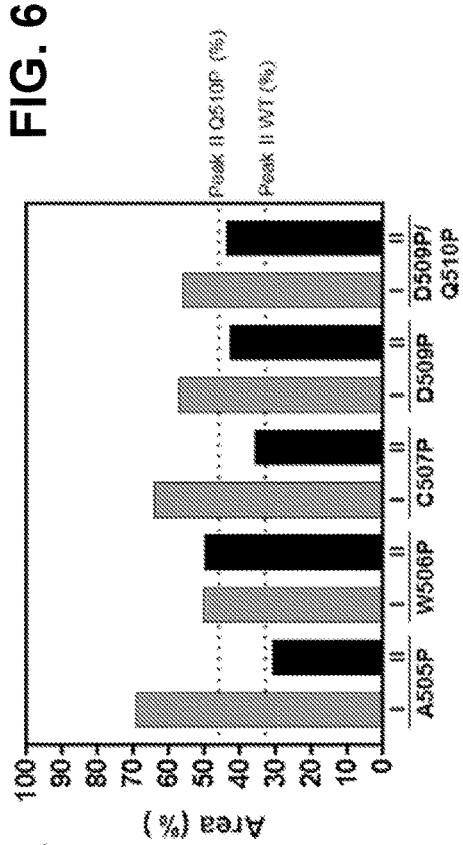
FIG. 6A depicts quantification (in percent) of Peak I and Peak II population by SEC-HPLC of gB'-A505P-GCN4, gB'-W506P-GCN4, gB'-Q507P-GCN4, gB'-D509P-GCN4, and gB'-D509P-Q510P-GCN4 molecules. Dotted lines indicate the Peak II percentage of gB'-GCN4 (designated as "WT" therein) and of the gB'-GCN4-Q510P mutant that is described elsewhere herein (designated as "Q510P" therein).

Additional gB'-GCN4 proline mutants were designed and evaluated for their effect on Peak II/Peak I ratio. In particular, A505P, W506P, C507P, D509P, D509P/Q510P double mutant and Q510P/R511P double mutant (all numbered with respect to SEQ ID NO: 1) were designed. With exception of the Q510P/R511P double mutant (that was not expressed due to a believed contamination issue with the sample), all proteins were expressed in 30 ml of expression media, purified by single step purification using NI SEPHAROSE EXCEL (GE Healthcare), or analyzed by NanoDSF and SEC-HPLC. SEC-HPLC revealed that W506P produced more Peak II than any other construct. A505P and C507P had Peak II level similar to gB'-GCN4 (which is referred to as Wild Type (WT) in FIGS. 6A and 6B). Peak II population for D509P and double mutant D509P/Q510P were slightly lower than Q510P (FIGS. 6A and 6B). These results indicate that the W506P proline mutation should increase the Peak II population and that the W506P and Q510P proline substitutions (here numbered according to SEQ ID NO: 1) should be combined to further increase the size of the Peak II population. It is notable that the W506 and Q510 residues point to the same interface within Domain III.

Example 3

Another modified HCMV gB molecule was generated (referred to as "gB$_{698}$-GCN4" herein) by further modifying the gB'2 molecule (described above) so that the entire MPR is deleted (i.e., residues D699-P751 of SEQ ID NO: 1 are deleted). For clarification, gB'-GCN4 described herein above comprises a truncated MPR (residues 699-724 of SEQ ID NO: 1) versus this gB$_{698}$-GCN4 molecule has had the entire MPR deleted (both molecules are based on the HCMV Merlin strain gB). gB$_{698}$-GCN4 is characterized by having a truncation of the MPR residues D699-P751 (inclusive) of SEQ ID NO: 1; insertion of two proline residues C-terminally adjacent to residue E698 (i.e., P699 and P700 of SEQ ID NO: 11); and the c-terminal-most proline (P700) being operably linked to the GCN4 with sequence SEQ ID NO: 2. gB$_{698}$-GCN4 can be represented by N'-E698-P-P-GCN4-C'. For expression and purification, a TEV cleavage site and 6×His tag (SEQ ID NO: 5) was inserted c-terminally adjacent to the GCN4. See the gB$_{698}$-GCN4 amino acid sequence SEQ ID NO: 11.

Figure 7B:
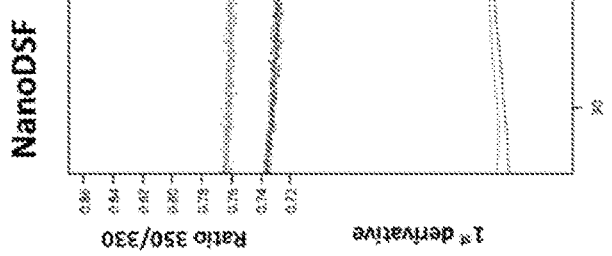
FIG. 7B depicts the thermal transition under NanoDSF analysis of $gB_{698}$-GCN4 and EBV-gB-GCN4 molecules.
Figure 7A:
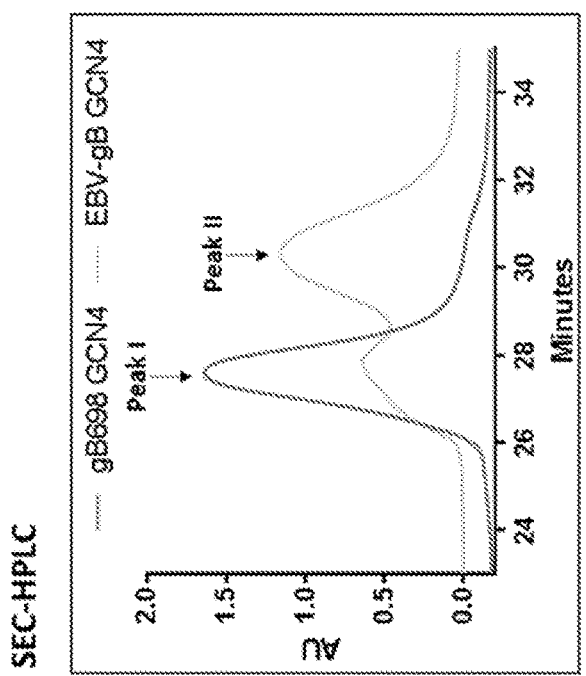
FIG. 7A depicts the elution profiles under SEC-HPLC analysis of $gB_{698}$-GCN4 (left/lower line with only one peak) and EBV-gB-GCN4 (right/top line with two peaks) molecules.

Using the publicly known EBV gB sequence published as UniProtKB Accession P03188 (entry 110 dated Dec. 11, 2019—provided herein as SEQ ID NO: 12), a modified EBV gB molecule was generated (referred to as "EBV-GCN4" herein) by truncating the MPR (i.e., deleting the residues c-terminal to residue Q705); inserting two proline residues C-terminally adjacent to residue Q705 (i.e., P706 and P707 of SEQ ID NO: 13); and operably linking the c-terminal-most proline (P707) to the GCN4 with sequence SEQ ID NO: 2. EBV-GCN4 can be represented by N'-Q705-P-P-GCN4-C'. For expression and purification, a TEV cleavage site and a 6×His tag (SEQ ID NO: 5) was inserted c-terminally adjacent to the GCN4. See the EBV-GCN4 amino acid sequence SEQ ID NO: 13.

gB$_{698}$-GCN4 and EBV-GCN4 were expressed and purified as described above (expressed in 30 ml from EXPi293 mammalian cells and purified by NI SEPHAROSE EXCEL (GE Healthcare) column). gB$_{698}$-GCN4, which does not contain an MPR, showed mainly Peak I under SEC-HPLC analysis (FIG. 7A). This result indicates that a functional MPR region (the region corresponding to residues 699-724 of SEQ ID NO: 1) is necessary for the formation of Peak II. Furthermore, under NanoDSF analysis gB$_{698}$-GCN4 was shown to have a higher Peak I Tm than what is usually observed for postfusion gB. Without wishing to be bound by theory, the higher Tm is believed to be due to the presence of GCN4 (FIGS. 7A and 7B).

EBV-gB GCN4 revealed a major peak corresponding to CMV-gB GCN4 Peak II elution time (FIG. 7A), however NanoDSF revealed a Tm close to 78° C., which is typical of postfusion gB (FIG. 7B). Further analysis can be conducted to assess and confirm the conformation of EBV-gB GCN4.

Example 4

A large batch (1 L) of gB'-Q510P-GCN4 was produced to obtain enough Peak II for structural and stability studies as well as for future uses. gB'-Q510P-GCN4 was initially purified by single step purification using Excel-NiNTA and followed by several runs over preparative gel filtration (used HILOAD 16/600 SUPERDEX (GE Healthcare)). The eluted proteins were tested by SEC-HPLC and NanoDSF (data not shown). SEC fractions were analyzed by NanoDSF to evaluate the relative amount of Peak I and Peak II. Fractions containing mostly Peak II were pooled together and analyzed by NanoDSF and HPLC-SEC (data not shown). The final yield was about 10 mg of 90% pure Peak II of gB'-Q510P-GCN4.

Figure 8:
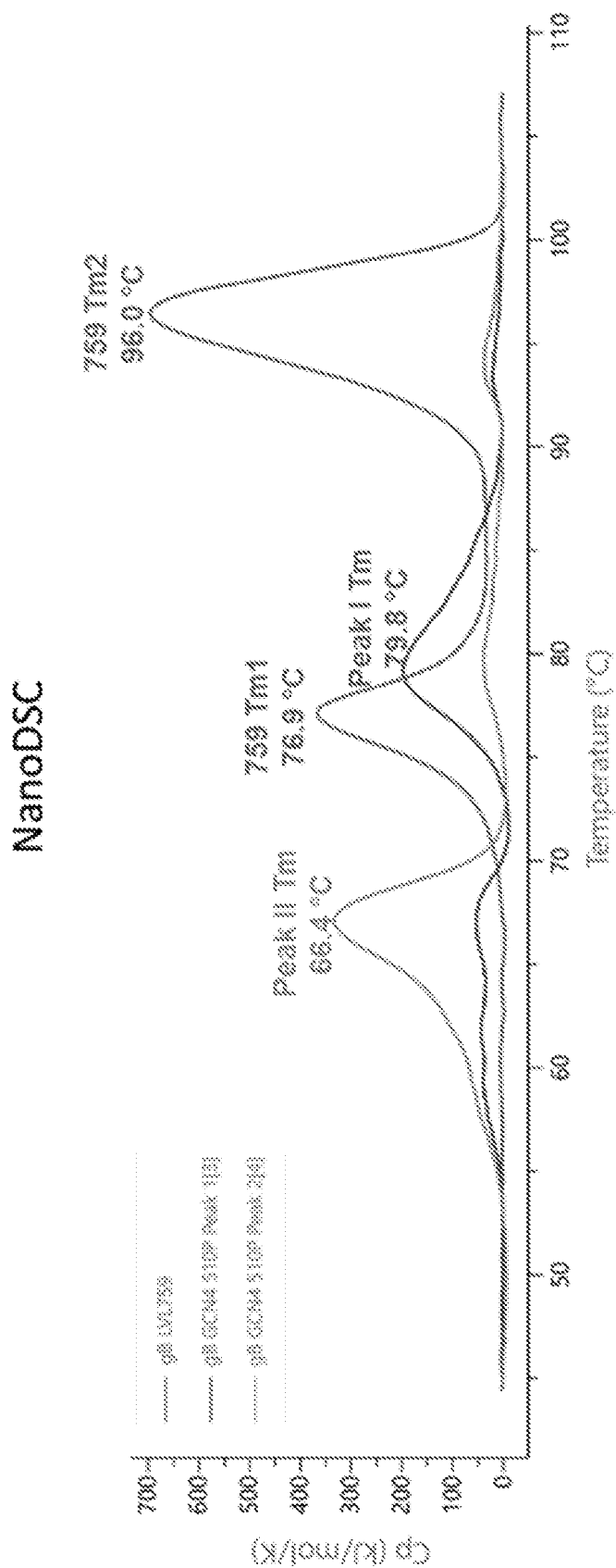
FIG. 8 depicts the thermal transition of Peak I and Peak II of gB'-GCN4-Q510P and LVL759 (control) under NanoDSC.

To fully understand the nature of Peak I and Peak II, the thermal stability of these two populations was evaluated by Differential Scanning Nanocalorimetry (NanoDSC) and postfusion gB molecule "LVL759" from HCMV AD169 strain (described in WO 2012/049317) was used as control. NanoDSC results confirmed that Peak I Tm and Peak II Tm are very different, being 66.4° C. and 76.9° C. respectively. The thermal unfolding of LVL759 revealed an anticipated transition at 79.8° C. and an unexpected additional transition at 96.0° C., which was undetected by NanoDSF due to technical limitations (FIG. 8). The results from previous experiments (herein above) indicated that Peak I molecules have a conformation that corresponds to that of postfusion gB (such molecules being referred to as "post-fusion-like" herein for that reason) because its Tm (~78.5° C.) is similar to that of LVL759 under nanoDSF analysis and it has a more elongated shape, while Peak II molecules have a conformation that corresponds to a non-postfusion conformation because its Tm is lower (~65.5° C.) and it has a more globular shape than Peak I molecules. However, the unfolding profile of LVL759 under NanoDSC analysis suggests that Peak I molecules are also in a non-post-fusion conformation or an intermediate state between pre- and postfusion conformations.

Figure 9:
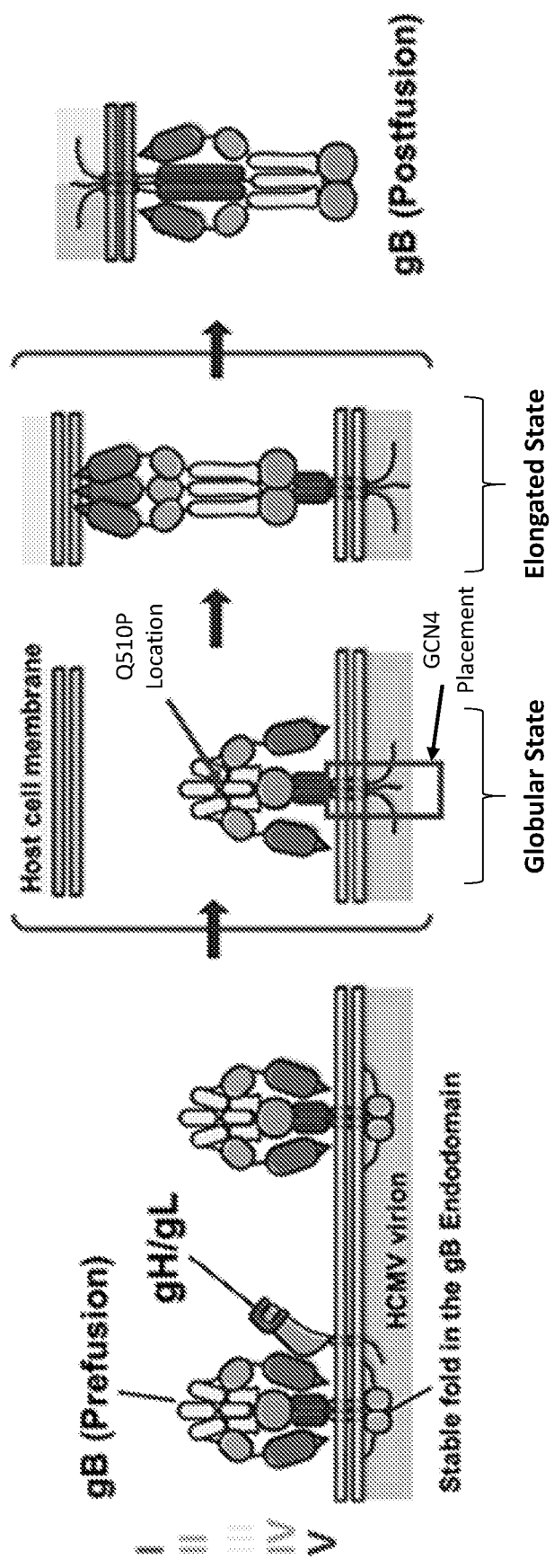
FIG. 9 provides a schematic representation of what is believed to be the transition from pre- to postfusion HCMV gB (schematic adapted from Nishimura & Mori 2019 Ad. Vir. Res. 104: 283-312). The box on the Globular State gB shows where the GCN4 was placed and the arrow on the Globular State shows the location of the Q510P mutation described herein.

These results from NanoDSC analysis fit the hypothesis of the inventors that GCN4 should prevent the Domain V to lock gB in the prefusion conformation. FIG. 9 provides a schematic representation of what is believed to be the transition from pre- to postfusion HCMV gB based on CryoET prefusion model and postfusion crystal structure (FIG. 9 is a modified version of FIG. 4 from Nishimura & Mon "Chapter 8: Entry of betaherpesviruses" 2019 Ad. Vir. Res. 104: 283-312). Overall, the biophysical evidence collected so far (including the results described herein) suggest that Peak II should resemble to the globular state, while Peak I should be like the extended state (FIG. 9).

Example 5

Figure 10A:
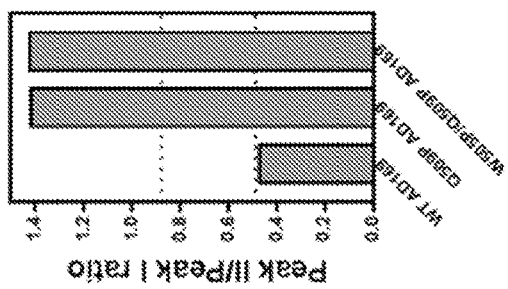
FIG. 10A depicts the quantification of Peak II to Peak I ratio observed for gB'-GCN4 (labeled as "WT") and molecules (1)-(8) from Example 1 following SEC-HPLC analysis (see Examples 1 and 5).
Figure 10B:
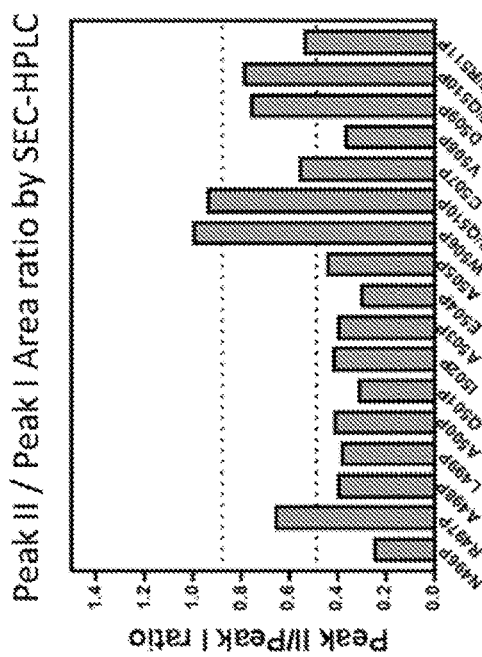
FIG. 10B depicts the quantification of Peak II to Peak I ratio observed for gB'-GCN4 (labeled as "WT") and molecules (9)-(25) following SEC-HPLC analysis (see Example 5). Top dotted line (at about 0.9) indicates the Peak II:Peak I ratio observed for the gB'-Q510P-GCN4 molecule. Bottom dotted line (at about 0.5) indicates the Peak II:Peak I ratio observed for the gB'-GCN4 molecule.
Figure 10C:
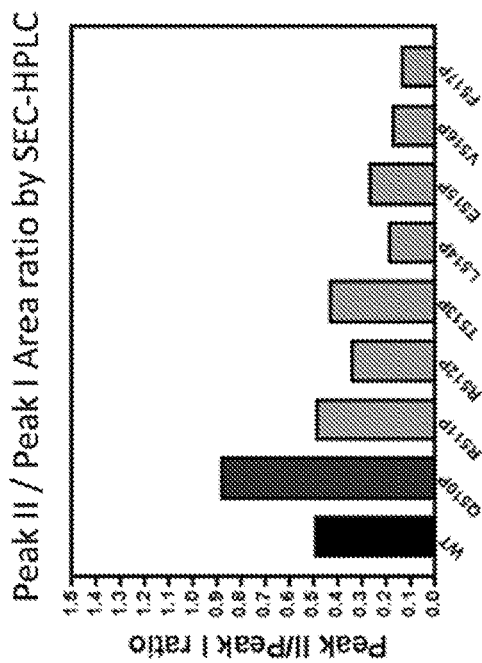
FIG. 10C depicts the quantification of Peak II to Peak I ratio observed for gB$_{698}$-GCN4 (labeled as "WT AD169") and molecules (26)-(27) following SEC-HPLC analysis (see Example 5). Top dotted line (at about 0.9) indicates the Peak II:Peak I ratio observed for the gB'-Q510P-GCN4 molecule. Bottom dotted line (at about 0.5) indicates the Peak II:Peak I ratio observed for the gB'-GCN4 molecule.

It was desirable to generate a modified HCMV gB molecule based on the AD169 strain that has the features of the gB'-GCN4 molecule described above (which is based on the HCMV Merlin strain gB). Therefore, the modified HCMV gB molecule "AD169-GCN4" was generated by truncating the MPR (i.e., deleting the residues c-terminal to residue K723); inserting two proline residues C-terminally adjacent to residue K723 (i.e., P724 and P725 of SEQ ID NO: 14); and operably linking the c-terminal-most proline (P725) to the GCN4 with sequence SEQ ID NO: 2. AD169-GCN4 can be represented by N'-K723-P-P-GCN4-C'. For expression and purification, a TEV cleavage site and a 6×His tag (SEQ ID NO: 5) was inserted c-terminally adjacent to the GCN4. See the AD169-GCN4 amino acid sequence SEQ ID NO: 14.

gB'-GCN4 (based on HCMV Merlin strain, as described above) and Molecules (1)-(8) from Example 1 were expressed in 150 ml of expression media, purified by single step purification, and further analyzed (see FIG. 10A, gB'-GCN4 as "WT" therein). Molecules (9)-(25) listed below (also based on HCMV Merlin strain) were expressed in 30 ml of expression media, purified by single step purification, and further analyzed (see FIG. 10B). AD169-GCN4 (based on HCMV AD169 strain, as described above) and Molecules (26)-(27) were also were expressed in 30 ml of expression media, purified by single step purification, and further analyzed (see FIG. 10C, AD169-GCN4 as "WT AD169" therein). As is also explained elsewhere herein, residues W505 and Q509 of AD169 gB (SEQ ID NO: 6) (see FIG. 10C) correspond to residues W506 and Q510, respectively, of Merlin gB (SEQ ID NO: 1) (see FIG. 10B). Summary of Molecules produced and analyzed here:

(9) gB'-N496P-GCN4,
(10) gB'-R497P-GCN4,
(11) gB'-A498P-GCN4,
(12) gB'-L499P-GCN4,
(13) gB'-A500P-GCN4,
(14) gB'-Q501P-GCN4,
(15) gB'-I502P-GCN4,
(16) gB'-A503P-GCN4,
(17) gB'-E504P-GCN4,
(18) gB'-A505P-GCN4,
(19) gB'-W506P-GCN4,
(20) gB'-W506-Q510P-GCN4,
(21) gB'-Q507P-GCN4,
(22) gB'-V508P-GCN4,
(23) gB'-D509P-GCN4,
(24) gB'-D509P-Q510P-GCN4,
(25) gB'-Q510P-R511P-GCN4,
(26) AD169-Q509P-GCN4 ("Q509P AD169" within FIG. 10C), and
(27) AD169-W505P-Q509P-GCN4 ("W505P/Q509P AD169" within FIG. 10C).

In particular, each protein was analyzed by nanoDSF and showed two thermal transition related to Peak I and Peak II (data not shown). For each, SEC-HPLC was used to quantify the relative amount of Peak II and Peak I and their ratio (FIGS. 10A, 10B, and 10C). gB'-W506-Q510P-GCN4 produced similar amount of Peak II as did gB'-W506P-GCN4 and gB'-Q510P-GCN4 single mutants (FIGS. 10A and 10B), indicating that it is not possible to further increase the production of Peak II (at least in HCMV Merlin strain) above what is obtained by gB'-W506P-GCN4 and gB'-Q510P-GCN4. Surprisingly, both AD169-Q509P-GCN4 and AD169-W505P-Q509P-GCN4 (both based on AD169 strain) dramatically increased the production of Peak II (an about 3-fold increase in the Peak II to Peak I ratio compared to the ratio observed with the control AD169-GCN4 molecule (see FIG. 10C, AD169-GCN4 labeled as "WT AD169" therein)). Without wishing to be bound by theory, it is believed that the results in Merlin-strain-based molecules as compared to AD169-strain-based molecules is due to sequence variability, in particular, sequence variability across the furin cleavage site or at the N-terminus (which is known to be a less conserved region of gB).

The presence of several epitopes in AD169-Q509P-GCN4 was confirmed via Surface Plasmon Resonance (SPR) that showed high affinity binding to several distinct antibodies, including the presence of antigenic domain 5 (AD-5) epitope via high affinity binding to a neutralizing antibody (antibody data not shown; see Chandramouli et al. 2015 Nat. Comm. 6(8176): 1-12 regarding AD-5).

Taken together, these results show that a gB protein that is already in a non-postfusion conformation (e.g., gB'-GCN4, gB$_{698}$-GCN4, or AD169-GCN4) can be further stabilized (or prevented from transitioning into postfusion conformation) by inserting one or more helix-breaking amino acids (such as one or more proline substitutions) into the DIIIcc Region residues (see Table 2). In particular, these results show that the Peak II population of gB'-GCN4 (based on HCMV Merlin strain) may be increased by adding a Q510P (FIG. 10A); R497P, W506P, W506P and Q510P, C507P, D509P, D509P and Q510P, or Q510P and R511P (FIG. 10B) mutation(s) to the gB'-GCN4 molecule. These results also show that the Peak II population of AD169-GCN4 (based on HCMV AD169 strain) may be increased by adding a Q509P or W505P and Q509P mutation(s) to the AD169-GCN4 (FIG. 10C). Based on the results shown with gB'-GCN4 being further modified by introducing one or two proline substitutions, introducing a R496P, W505P, C506P, D508P, D508P and Q509P, or Q509P and R510P substitution(s) (numbered according to SEQ ID NO: 6) to the AD169-GCN4 molecule is likewise expected to increase the peak II population as compared to what was observed for AD169-GCN4.

Example 6

Based on these results, an animal study is carried out with modified gB molecules of peak I and peak II conformation (e.g., from gB'-GCN4 or AD169-GCN4 molecules such as AD169-Q509-GCN4) to verify their antigenicity and immunogenicity.

The various features which are referred to in individual sections above apply, as appropriate, to other sections. Consequently, features specified in one section may be combined with features specified in other sections, as appropriate. Those skilled in the art will recognize or be able to ascertain using no more than routine experimentation, many equivalents to the specific embodiments of the invention (or aspects of the disclosure) described herein. Such equivalents are intended to be encompassed by the following:

1. A modified HCMV gB protein comprising a heterologous trimerization domain, such as a GCN4 Leucine Zipper domain (GCN4)) operably linked C-terminal to the residue corresponding to 724 numbered according to SEQ ID NO: 1 (specifically K724 numbered according to SEQ ID NO: 1).

2. The modified HCMV gB protein of 1 that does not comprise the native amino acid residues c-terminal to the residue corresponding to 724, numbered according to SEQ ID NO: 1 (specifically does not comprise the native amino acid residues corresponding to 725-907 of SEQ ID NO: 1).

3. The modified HCMV gB protein of 2, wherein the native amino acid residues comprise a transmembrane domain, cytoplasmic domain, or both.

4. The modified HCMV gB protein of any one of 1-3, wherein one or two proline residues are between the residue corresponding to 724, numbered according to SEQ ID NO: 1, and the trimerization domain.

5. The modified HCMV gB protein of any one of 1-4, where the trimerization domain is a GCN4 domain comprising SEQ ID NO: 2.

6. The modified HCMV gB protein of any one of 1-5 that is a modified HCMV strain AD169 gB or Merlin strain HCMV gB.

7. The modified HCMV gB protein of any one of 1-6 that is a modified HCMV gB protein and the trimerization domain is operably linked c-terminal to a lysine (K) residue corresponding to 724 of SEQ ID NO: 1 (e.g., linked c-terminal to residue 724 of SEQ ID NO: 1 or 723 of SEQ ID NO: 6).

8. The modified HCMV gB protein of 7 that is a modified HCMV gB protein modified as compared to a HCMV gB protein from Merlin strain.

9. The modified HCMV gB protein of any one of 1-8 that is in pre-fusogenic conformation.

10. The modified HCMV gB protein of any one of 1-9, further comprising:
(i) a substitution of one or more furin cleavage site amino acid (specifically one or more furin cleavage site amino acid at a position corresponding to 457, 458, 459, or 460 of SEQ ID NO: 1),
(ii) a substitution of one or more fusion loop amino acid (specifically one or more fusion loop amino acid at a position corresponding to 155, 156, 157, 240, 241, or 242 of SEQ ID NO: 1), or
(iii) both (i) and (ii).

11. The modified HCMV gB protein of 10, comprising:
(i) a substitution at the furin cleavage site residue corresponding to 458, 460, or both of SEQ ID NO: 1 (specifically at the furin cleavage site residue corresponding to 458 and 460 of SEQ ID NO: 1; more specifically a substitution to serine at the residues corresponding to 458 and 460 of SEQ ID NO: 1);
(ii) a substitution at the fusion loop amino acids corresponding to 155, 156, 157, 240, 241, and 242 of SEQ ID NO: 1 (specifically a substitution to glycine (G) at the residue corresponding to 155 of SEQ ID NO: 1, a substitution to histidine (H) at the residue corresponding to 156 of SEQ ID NO: 1, a substitution to arginine (R) at the residue corresponding to 157 of SEQ ID NO: 1, a substitution to phenylalanine (F) at the residue corresponding to 240 of SEQ ID NO: 1, a substitution to phenylalanine (F) at the residue corresponding to 241 of SEQ ID NO: 1, and a substitution to histidine (H) at the residue corresponding to 242 of SEQ ID NO: 1), or
(iii) both (i) and (ii).

12. The modified HCMV gB protein of any one of 1-11, further comprising a purification tag (specifically a 6-histidine purification tag), optionally that is operably linked to a cleavage linker (specifically a TEV cleavage linker).

13. The modified HCMV gB protein of any one of 1-12, further comprising a proline, glycine, serine, or alanine substitution of one or more (such as one or two) residues corresponding to N478-R511 numbered according to SEQ ID NO: 1.

14. The modified HCMV gB protein of 13 that is:
(I) a modified HCMV gB protein comprising N478P, L479P, V480P, Y481P, A482P, Q483P, L484P, Q485P, F486P, T487P, Y488P, D489P, T490P, L491P, R492P, G493P, Y494P, I495P, N496P, R497P, A498P, L499P, A500P, Q501P, I502P, A503P, E504P, A505P, W506P, C507P, V508P, D509P, Q510P, R511P, or combinations thereof, numbered according to SEQ ID NO: 1;
(II) a modified HCMV gB protein comprising N477P, L478P, V479P, Y480P, A481P, Q482P, L483P, Q484P, F485P, T486P, Y487P, D488P, T489P, L490P, R491P, G492P, Y493P, I494P, N495P, R496P, A497P, L498P, A499P, Q500P, I501P, A502P, E503P, A504P, W505P, C506P, V507P, D508P, Q509P, R510P, or combinations thereof, numbered according to SEQ ID NO: 6;
(III) a modified HCMV gB protein comprising N478G, L479G, V480G, Y481G, A482G, Q483G, L484G, Q485G, F486G, T487G, Y488G, D489G, T490G, L491G, R492G, Y494G, I495G, N496G, R497G, A498G, L499G, A500G, Q501G, I502G, A503G, E504G, A505G, W506G, C507G, V508G, D509G, Q510G, R511G, or combinations thereof, numbered according to SEQ ID NO: 1;
(IV) a modified HCMV gB protein comprising N477G, L478G, V479G, Y480G, A481G, Q482G, L483G, Q484G, F485G, T486G, Y487G, D488G, T489G, L490G, R491G, Y493G, I494G, N495G, R496G, A497G, L498G, A499G, Q500G, I501G, A502G, E503G, A504G, W505G, C506G, V507G, D508G, Q509G, R510G, or combinations thereof, numbered according to SEQ ID NO: 6;
(V) a modified HCMV gB protein comprising N478S, L479S, V480S, Y481S, A482S, Q483S, L484S, Q485S, F486S, T487S, Y488S, D489S, T490S, L491S, R492S, G493S, Y494S, I495S, N496S, R497S, A4985, L499S, A500S, Q501S, I502S, A5035, E5045, A5055, W5065, C5075, V5085, D5095, Q510S, R5115, or combinations thereof, numbered according to SEQ ID NO: 1;
(VI) a modified HCMV gB protein comprising N477S, L478S, V479S, Y480S, A481S, Q482S, L483S, Q484S, F485S, T486S, Y487S, D488S, T489S, L490S, R491S, G492S, Y493S, I494S, N495S, R496S, A497S, L4985, A499S, Q500S, I501S, A502S, E503S, A504S, W505S, C506S, V507S, D508S, Q509S, R510S, or combinations thereof, numbered according to SEQ ID NO: 6;
(VII) a modified HCMV gB protein comprising N478A, L479A, V480A, Y481A, Q483A, L484A, Q485A, F486A, T487A, Y488A, D489A, T490A, L491A, R492A, G493A, Y494A, I495A, N496A, R497A, L499A, Q501A, I502A, E504A, W506A, C507A, V508A, D509A, Q510A, R511A, or combinations thereof, numbered according to SEQ ID NO: 1; or
(VIII) a modified HCMV gB protein comprising N477A, L478A, V479A, Y480A, Q482A, L483A, Q484A, F485A, T486A, Y487A, D488A, T489A, L490A, R491A, G492A, Y493A, I494A, N495A, R496A, L498A, Q500A, I501A, E503A, W505A, C506A, V507A, D508A, Q509A, R510A, or combinations thereof, numbered according to SEQ ID NO: 6.

15. The modified HCMV gB protein of 14 that is:
(I) a modified HCMV gB protein comprising R497P, A503P, E504P, A505P, W506P, C507P, V508P, D509P, Q510P, R511P, or combinations thereof, numbered according to SEQ ID NO: 1; or
(II) a modified HCMV gB protein comprising R496P, A502P, E503P, A504P, W505P, C506P, V507P, D508P, Q509, R510P, or combinations thereof, numbered according to SEQ ID NO: 6.

16. The modified HCMV gB protein of 15 that is:
(I) a modified HCMV gB protein comprising R497P, W506P, C507P, D509P, Q510P, R511P, W506P and Q510P, D509P and Q510P, or combinations thereof, numbered according to SEQ ID NO: 1; or
(II) a modified HCMV gB protein comprising R496P, W505P, C506P, D508P, Q509P, R510P, W505P and Q509P, D508P and Q509P, or combinations thereof, numbered according to SEQ ID NO: 6 (such as a modified HCMV gB protein comprising Q509P, W505P and Q509P, or combinations thereof, numbered according to SEQ ID NO: 6).

17. The modified HCMV gB protein of any one of 1-16 that is a modified HCMV gB protein comprising the substitution Q510P numbered according to SEQ ID NO: 1.

18. The modified HCMV gB protein of any one of 1-17 that is in pre-fusogenic conformation.

19. The modified HCMV gB protein of any one of 1-18, comprising an amino acid sequence with at least 90%, 91%, 92%, 93%, 94%, 95%, 96%, 97%, 98%, 99%, or 100% identity to SEQ ID NO: 3 or 4 (such as a modified HCMV gB protein with an amino acid sequence comprising: residues 23-759 of SEQ ID NO: 3, residues 23-733 of SEQ ID NO: 11, residues 22-740 of SEQ ID NO: 13, residues 23-758 of SEQ ID NO: 14, or one or SEQ ID NOs: 15-30).

20. The modified HCMV gB protein of any one of 1-19 operably linked to a carrier.

21. The modified HCMV gB protein of 20, wherein the carrier is a nanoparticle.

22. The modified HCMV gB protein of 21, wherein the nanoparticle is, or is derived from, a lumazine synthase or ferritin protein.

23. An isolated nucleic acid comprising a polynucleotide sequence encoding the modified HCMV gB protein of any one of 1-19.

24. The nucleic acid of 23, wherein the polynucleotide sequence is an RNA.

26. The nucleic acid of 24, wherein the RNA is a self-replicating RNA, optionally an alphavirus replicon.

27. An alphavirus replication particle (VRP) comprising the alphavirus replicon of 26.

28. An immunogenic composition comprising the modified HCMV gB protein of any one of 1-22, the nucleic acid of any one of 23-26, or the VRP of 27.

29. The immunogenic composition of 28 further comprising an adjuvant.

30. The immunogenic composition of 29, wherein the adjuvant comprises an aluminum salt, a TLR7 agonist, TLR4 agonist, MPL, 3D-MPL, saponin, or an oil-in-water emulsion.

31. A recombinant vector comprising the nucleic acid of any one of 23-26.

32. An isolated host cell comprising the nucleic acid of any one of 23-26, optionally wherein the polynucleotide is DNA and stably incorporated into the genomic DNA of the host cell.

33. The isolated host cell of 32, wherein the host cell is a mammalian cell.

34. The isolated host cell of 33, wherein the mammalian cell is a CHO cell or HEK-293 cell.

35. A cell culture comprising the host cell of any one of 32-34.

36. A process of producing a modified HCMV gB protein comprising culturing the host cell of any one of 32-34 under suitable conditions, thereby expressing the modified HCMV gB protein.

37. The process of 36, further comprising collecting the modified HCMV gB protein from the cultured host cell(s), and optionally purifying the modified HCMV gB protein.

38. A modified HCMV gB protein produced by the process of 36 or 37.

39. A process of producing a population of host cells, comprising culturing host cells according to any one of 32-34 under suitable conditions for expression of a modified HCMV gB protein according to any one of 13-20, thereby producing a population of host cells and optionally purifying the modified HCMV gB protein, wherein at least 35%, 36%, 37%, 38%, 39%, 40%, 41%, 42%, 43%, 44%, or 45% of the purified modified HCMV gB proteins are in pre-fusogenic conformation.

40. The population of host cells produced by the process of 39.

41. The population of host cells of 40, wherein at least 35%, 36%, 37%, 38%, 39%, 40%, 41%, 42%, 43%, 44%, or 45% of the modified HCMV gB proteins expressed from said host cells are in pre-fusogenic conformation.

42. An immunogenic composition comprising the modified HCMV gB protein of any one of 1-22 or 38 and at least one additional HCMV protein, or an immunogenic fragment thereof.

43. The immunogenic composition of 42, wherein the at least one additional HCMV protein, or immunogenic fragment thereof, is gO, gH, gL, pUL128, pUL130, pUL131, pp65, IE1, or a combination thereof.

44. The immunogenic composition of 42 or 43, comprising the modified HCMV gB protein of any one of 1-22 and 38; gH, or an immunogenic pentamer-complex forming fragment thereof; gL, or an immunogenic pentamer-complex forming fragment thereof; pUL128, or an immunogenic pentamer-complex forming fragment thereof; pUL130, or an immunogenic pentamer-complex forming fragment thereof; and pUL131, or an immunogenic pentamer-complex forming fragment thereof.

45. The immunogenic composition of 43 or 44, wherein the gH protein, or immunogenic pentamer-complex forming fragment thereof, lacks a transmembrane domain.

46. The immunogenic composition of one of 43-45, wherein the gL protein, or immunogenic pentamer-complex forming fragment thereof, comprises a modification in a protease recognition site that reduces protease cleavage of said gL or immunogenic pentamer-complex forming fragment.

47. The immunogenic composition of any one of 42-46, further comprising an adjuvant.

48. The immunogenic composition of 47, wherein the adjuvant comprises aluminum salt, a TLR7 agonist, TLR4 agonist, MPL, 3D-MPL, saponin, or an oil-in-water emulsion.

49. An isolated antibody, or antigen-binding fragment thereof, specific for the modified HCMV gB protein of any one of 1-22, 38.

50. A pharmaceutical composition comprising the antibody, or antigen-binding fragment thereof, of 49.

51. Use of the modified HCMV gB protein of any one of 1-22 or 38; nucleic acid of any one of 23-26; VRP of 27; immunogenic composition of any one of 28-30, 42-48; vector of 31; antibody or antibody fragment of 49; or pharmaceutical composition of 50 in the prevention or treatment of a HCMV infection.

52. Use of the modified HCMV gB protein of any one of 1-23 or 38; nucleic acid of any one of 24-26; VRP of 27; immunogenic composition of any one of 28-30, 42-48; vector of 31; antibody or antibody fragment of 49; or pharmaceutical composition of 50 for inducing an immune response against HCMV.

53. Use of the modified HCMV gB protein of any one of 1-23 or 38; nucleic acid of any one of 24-26; VRP of 27; immunogenic composition of any one of 28-30, 42-48; vector of 31; antibody or antibody fragment of 49; or pharmaceutical composition of 50 for the manufacture of a medicament for inducing an immune response against HCMV.

54. Use of the modified HCMV gB protein of any one of 1-22 or 38; nucleic acid of any one of 24-26; VRP of 27; immunogenic composition of any one of 28-30, 42-48; vector of 31; antibody or antibody fragment of 49; or pharmaceutical composition of 50 for the manufacture of a medicament for inhibiting HCMV entry into a cell (specifically, inhibiting membrane fusion for HCMV entry into a cell).

55. The modified HCMV gB protein of any one of 1-22 or 38; nucleic acid of any one of 24-26; VRP of 27; immunogenic composition of any one of 28-30, 42-48; vector of 31; antibody or antibody fragment of 49; or pharmaceutical composition of 50 for use in the prevention or treatment of HCMV infection.

56. The modified HCMV gB protein of any one of 1-22 or 38; nucleic acid of any one of 24-26; VRP of 27; immunogenic composition of any one of 28-30, 42-48; vector of 31; antibody or antibody fragment of 49; or pharmaceutical composition of 50 for use in inducing an immune response against HCMV.

57. The modified HCMV gB protein of any one of 1-22 or 38; nucleic acid of any one of 24-26; VRP of 27; immunogenic composition of any one of 28-30, 42-48; vector of 31; antibody or antibody fragment of 49; or pharmaceutical composition of 50 for use in inhibiting HCMV entry into a cell (specifically, inhibiting membrane fusion for HCMV entry into a cell).

58. A method of inhibiting HCMV entry into a cell (specifically, inhibiting membrane fusion for HCMV entry into a cell), comprising contacting the cell with the modified HCMV gB protein of any one of 1-22 or 38; nucleic acid of any one of 24-26; VRP of 27; immunogenic composition of any one of 28-30, 42-48; vector of 31; antibody or antibody fragment of 49; or pharmaceutical composition of 50.

59. A method of inducing an immune response against HCMV in a subject, comprising administering to the subject an immunologically effective amount of the modified HCMV gB protein of any one of 1-22 or 38; nucleic acid of any one of 24-26; VRP of 27; immunogenic composition of any one of 28-30, 42-48; vector of 31; antibody or antibody fragment of 49; or pharmaceutical composition of 50.

60. A kit for identifying the presence of a modified HCMV gB protein within a composition, for the purification of a modified HCMV gB protein from a composition, for detecting a modified HCMV gB protein in pre-fusion, or for detecting a modified HCMV gB protein in a non-post-fusion conformation, or for the prevention or treatment of HCMV infection; comprising the antibody or antigen-binding fragment thereof of 48, and optionally instructions for using the antibody or antigen-binding fragment thereof.

Explanation of Sequences

SEQ ID NO: 1—Amino acid sequence of wild type, Merlin strain, Human Cytomegalovirus gB protein. See Chandramouli et al. 2015 Nat. Comm. 6(8176) at FIG. 1: See also UniProtKB Accession No. F5HB53 (GB_HCMVM; sequence version 1 last updated Jun. 28, 2011).

Predicted Signal peptide residues M1-A22 (double underlined);
Fusion Loop 1 residues $^{155}$YIH$^{157}$ (underlined);
Fusion Loop 2 residues $^{240}$WLY$^{242}$ (underlined);
Furin Cleavage Site residues R457 and R460 (underlined);
Domain III Coiled-coil Region residues N478-1523 underlined with residues N478-R511 being double underlined;
MPR residues D699-P751 residues (underlined) with residue K724 in bold;
Transmembrane domain residues F752-Y772 (double underlined);
Cytoplasmic domain is from residues T773-V907.

```
            10         20         30         40         50         60
    MESRIWCLVV CVNLCIVCLG AAVSSSSTRG TSATHSHHSS HTTSAAHSRS GSVSQRVTSS 70         80         90        100        110        120
    QTVSHGVNET IYNTTLKYGD VVGVNTTKYP YRVCSMAQGT DLIRFERNIV CTSMKPINED 130        140        150        160        170        180
    LDEGIMVVYK RNIVAHTFKV RVYQKVLTFR RSYAYIHTTY LLGSNTEYVA PPMWEIHHIN 190        200        210        220        230        240
    SHSQCYSSYS RVIAGTVFVA YHRDSYENKT MQLMPDDYSN THSTRYVTVK DQWHSRGSTW 250        260        270        280        290        300
    LYRETCNLNC MVTITTARSK YPYHFFATST GDVVDISPFY NGTNRNASYF GENADKFFIF 310        320        330        340        350        360
    PNYTIVSDFG RPNSALETHR LVAFLERADS VISWDIQDEK NVTCQLTFWE ASERTIRSEA 370        380        390        400        410        420
    EDSYHFSSAK MTATFLSKKQ EVNMSDSALD CVRDEAINKL QQIFNTSYNQ TYEKYGNVSV 430        440        450        460        470        480
    FETTGGLVVF WQGIKQKSLV ELERLANRSS LNLTHNRTKR STDGNNATHL SNMESVHNLV 490        500        510        520        530        540
    YAQLQFTYDT LRGYINRALA QIAEAWCVDQ RRTLEVFKEL SKINPSAILS AIYNKPIAAR 550        560        570        580        590        600
    FMGDVLGLAS CVTINQTSVK VLRDMNVKES PGRCYSRPVV IFNFANSSYV QYGQLGEDNE 610        620        630        640        650        660
    ILLGNHRTEE CQLPSLKIFI AGNSAYEYVD YLFKRMIDLS SISTVDSMIA LDIDPLENTD 670        680        690        700        710        720
    FRVLELYSQK ELRSSNVFDL EEIMREFNSY KORVKYVEDK VVDPLPPYLK GLDDLMSGLG 730        740        750        760        770        780
    AAGKAVGVAI GAVGGAVASV VEGVATFLKN PFGAFTIILV AIAVVIITYL IYTRQRRLCT
```

-continued

```
           790        800        810        820        830        840
    QPLQNLFPYL VSADGTTVTS GSTKDTSLQA PPSYEESVYN SGRKGPGPPS SDASTAAPPY 850        860        870        880        890        900
    TNEQAYQMLL ALARLDAEQR AQQNGTDSLD GRTGTQDKGQ KPNLLDRLRH RKNGYRHLKD

SDEEENV
```

SEQ ID NO: 2—Amino acid sequence of GCN4 Leucine Zipper Domain in a trimeric oligomerization state (see Oshaben et al., 2012 Biochemistry 51(47): 9581-9591; see also Protein 50 Data Bank (PDB) Accession 4DME)

```
            10         20         30
    RMKQLEDKVE ELLSKNYHLE NEVARLKKLV GER
```

SEQ ID NO: 3 (gB'-GCN4)—exemplary amino acid sequence of a modified HCMV gB protein from these studies comprising, as compared to wild type Merlin HCMV gB (SEQ ID NO: 1):

Insertion of two proline residues c-terminally adjacent to residue K724 (underlined);

Insertion of GCN4 sequence SEQ ID NO: 2 c-terminally adjacent to the c-terminal-most inserted proline residue (double underlined);

This sequence may be further modified by operably linking a TEV cleavage site and 6×His tag (SEQ ID NO: 5) to the C-terminus of the GCN4 sequence, as is shown in SEQ ID NO: 4.

```
                    10         20         30         40         50         60
            MESRIWCLVV CVNLCIVCLG AAVSSSSTRG TSATHSHHSS HTTSAAHSRS GSVSQRVTSS 70         80         90        100        110        120
            QTVSHGVNET IYNTTLKYGD VVGVNTTKYP YRVCSMAQGT DLIRFERNIV CTSMKPINED 130        140        150        160        170        180
            LDEGIMVVYK RNIVAHTFKV RVYQKVLTFR RSYAGHRTTY LLGSNTEYVA PPMWEIHHIN 190        200        210        220        230        240
            SHSQCYSSYS RVIAGTVFVA YHRDSYENKT MQLMPDDYSN THSTRYVTVK DQWHSRGSTA 250        260        270        280        290        300
            FHRETCNLNC MVTITTARSK YPYHFFATST GDVVDISPFY NGTNRNASYF GENADKFFIF 310        320        330        340        350        360
            PNYTIVSDFG RPNSALETHR LVAFLERADS VISWDIQDEK NVTCQLTFWE ASERTIRSEA 370        380        390        400        410        420
            EDSYHFSSAK MTATFLSKKQ EVNMSDSALD CVRDEAINKL QQIFNTSYNQ TYEKYGNVSV 430        440        450        460        470        480
            FETTGGLVVF WQGIKQKSLV ELERLANRSS LNLTHNSTKS STDGNNATHL SNMESVHNLV 490        500        510        520        530        540
            YAQLQFTYDT LRGYINRALA QIAEAWCVDQ RRTLEVFKEL SKINPSAILS AIYNKPIAAR 550        560        570        580        590        600
            FMGDVLGLAS CVTINQTSVK VLRDMNVKES PGRCYSRPVV IFNFANSSYV QYGQLGEDNE 610        620        630        640        650        660
            ILLGNHRTEE CQLPSLKIFI AGNSAYEYVD YLFKRMIDLS SISTVDSMIA LDIDPLENTD 670        680        690        700        710        720
            FRVLELYSQK ELRSSNVFDL EEIMREFNSY KQRVKYVEDK VVDPLPPYLK GLDDLMSGLG 730        740        750
            AAGKPPRMKQ LEDKVEELLS KNYHLENEVA RLKKLVGER
```

Predicted Signal peptide residues M1-A22 (underlined, would be removed in mature sequence);

Fusion Loop 1 modifications $^{155}$YIH$^{157}$ to $^{155}$GHR$^{157}$ (underlined);

Fusion Loop 2 modifications 240WLY$^{242}$ to $^{240}$AFH$^{242}$ (underlined);

Furin Cleavage Site residues R457S and R460S (underlined)

A truncation of the residues c-terminal to MPR residue K724 (residue in bold) (i.e., cleavage of the c-terminal end of the MPR and removal of the transmembrane and cytoplasmic domains);

SEQ ID NO: 4 (gB'-GCN4)—exemplary amino acid sequence of a modified HCMV gB protein from these studies comprising, as compared to wild type Merlin HCMV gB (SEQ ID NO: 1):

Predicted Signal peptide residues M1-A22 (would be removed in mature sequence);

Fusion Loop 1 modifications $^{155}$YIH$^{157}$ to $^{155}$GHR$^{157}$ (underlined);

Fusion Loop 2 modifications 240WLY$^{242}$ to $^{240}$AFH$^{242}$ (underlined);

Furin Cleavage Site residues R457S and R460S (underlined)

A truncation of the residues c-terminal to MPR residue K724 (residue in bold) (i.e., cleavage of the C-terminal end of the MPR and removal of the transmembrane and cytoplasmic domains);

Insertion of two proline residues c-terminally adjacent to residue K724 (underlined);

Insertion of GCN4 sequence SEQ ID NO: 2 C-terminally adjacent to the c-terminal-most inserted proline residue (double underlined);

Insertion of SEQ ID NO: 5 (i.e., a TEV cleavage site (underlined) and 6×His tag (double underlined) C-terminally adjacent to the GCN4 sequence).

```
           10         20         30         40         50         60
    MESRIWCLVV CVNLCIVCLG AAVSSSSTRG TSATHSHHSS HTTSAAHSRS GSVSQRVTSS 70         80         90        100        110        120
    QTVSHGVNET IYNTTLKYGD VVGVNTTKYP YRVCSMAQGT DLIRFERNIV CTSMKPINED 130        140        150        160        170        180
    LDEGIMVVYK RNIVAHTFKV RVYQKVLTFR RSYAGHRTTY LLGSNTEYVA PPMWEIHHIN 190        200        210        220        230        240
    SHSQCYSSYS RVIAGTVFVA YHRDSYENKT MQLMPDDYSN THSTRYVTVK DQWHSRGSTA 250        260        270        280        290        300
    FHRETCNLNC MVTITTARSK YPYHFFATST GDVVDISPFY NGTNRNASYF GENADKFFIF 310        320        330        340        350        360
    PNYTIVSDFG RPNSALETHR LVAFLERADS VISWDIQDEK NVTCQLTFWE ASERTIRSEA 370        380        390        400        410        420
    EDSYHFSSAK MTATFLSKKQ EVNMSDSALD CVRDEAINKL QQIFNTSYNQ TYEKYGNVSV 430        440        450        460        470        480
    FETTGGLVVF WQGIKQKSLV ELERLANRSS LNLTHNSTKS STDGNNATHL SNMESVHNLV 490        500        510        520        530        540
    YAQLQFTYDT LRGYINRALA QIAEAWCVDQ RRTLEVFKEL SKINPSAILS AIYNKPIAAR 550        560        570        580        590        600
    FMGDVLGLAS CVTINQTSVK VLRDMNVKES PGRCYSRPVV IFNFANSSYV QYGQLGEDNE 610        620        630        640        650        660
    ILLGNHRTEE CQLPSLKIFI AGNSAYEYVD YLFKRMIDLS SISTVDSMIA LDIDPLENTD 670        680        690        700        710        720
    FRVLELYSQK ELRSSNVFDL EEIMREFNSY KQRVKYVEDK VVDPLPPYLK GLDDLMSGLG 730        740        750        760        770
    AAGKPPRMKQ LEDKVEELLS KNYHLENEVA RLKKLVGERE NLYFQGGHHH HHH
```

SEQ ID NO: 5-a TEV cleavage site (underlined) and 6×His tag (double underlined).

```
           10
    ENLYFQGGHH HHHH
```

SEQ ID NO: 6—AD169 Strain HCMV gB amino acid sequence corresponding to UniProtKB Accession P06473 (version 1 of sequence last updated Jan. 1, 1988; see also FIG. 2 of Burke & Heldwein 2015 PLOS Path. DOI: 10.1371).

Domain III Coiled-coil Region residues N477-1522, corresponding to residues N478-1523 of SEQ ID NO: 1 (FIG. 2A), underlined and residues N477-R510, corresponding to residues N478-R511 of SEQ ID NO: 1, double underlined;

MPR residues D698-P750, corresponding to residues D699-P751 of SEQ ID NO: 1 (FIG. 2B) double underlined with residue K723, which corresponds to residue K724 of SEQ ID NO: 1, in bold.

```
           10         20         30         40         50
    MESRIWCLVV CVNLCIVCLG AAVSSSSTSH ATSSTHNGSH TSRTTSAQTR 60         70         80         90        100
    SVYSQHVTSS EAVSHRANET IYNTTLKYGD VVGVNTTKYP YRVCSMAQGT 110        120        130        140        150
    DLIRFERNII CTSMKPINED LDEGIMVVYK RNIVAHTFKV RVYQKVLTFR
```

```
        160        170        180        190        200
RSYAYIYTTY LLGSNTEYVA PPMWEIHHIN KFAQCYSSYS RVIGGTVFVA 210        220        230        240        250
YHRDSYENKT MQLIPDDYSN THSTRYVTVK DQWHSRGSTW LYRETCNLNC 260        270        280        290        300
MLTITTARSK YPYHFFATST GDVVYISPFY NGTNRNASYF GENADKFFIF 310        320        330        340        350
PNYTIVSDFG RPNAAPETHR LVAFLERADS VISWDIQDEK NVTCQLTFWE 360        370        380        390        400
ASERTIRSEA EDSYHFSSAK MTATFLSKKQ EVNMSDSALD CVRDEAINKL 410        420        430        440        450
QQIFNTSYNQ TYEKYGNVSV FETSGGLVVF WQGIKQKSLV ELERLANRSS 460        470        480        490        500
LNITHRTRRS TSDNNTTHLS SMESVHNLVY AQLQFTYDTL RGYINRALAQ 510        520        530        540        550
IAEAWCVDQR RTLEVFKELS KINPSAILSA IYNKPIAARF MGDVLGLASC 560        570        580        590        600
VTINQTSVKV LRDMNVKESP GRCYSRPVVI FNFANSSYVQ YGQLGEDNEI 610        620        630        640        650
LLGNHRTEEC QLPSLKIFIA GNSAYEYVDY LFKRMIDLSS ISTVDSMIAL 660        670        680        690        700
DIDPLENTDF RVLELYSQKE LRSSNVFDLE EIMREFNSYK ORVKYVEDKV 710        720        730        740        750
VDPLPPYLKG LDDLMSGLGA AGKAVGVAIG AVGGAVASVV EGVATFLKNP 760        770        780        790        800
FGAFTIILVA IAVVIITYLI YTRQRRLCTQ PLQNLFPYLV SADGTTVTSG 810        820        830        840        850
STKDTSLQAP PSYEESVYNS GRKGPGPPSS DASTAAPPYT NEQAYQMLLA 860        870        880        890        900
LARLDAEQRA QQNGTDSLDG QTGTQDKGQK PNLLDRLRHR KNGYRHLKDS

DEEENV

SEQ ID NO: 7-FLAG tag
DYKDDDDK

SEQ ID NO: 8-Streptavidin tag
AWRHPQFGG

SEQ ID NO: 9-Streptavidin tag
WSHPQFEK

SEQ ID NO: 10-Streptavidin tag
WSHPQFEKGGGSGGGSGGGSWSHPQFEK
```

SEQ ID NO: 11 (gB$_{698}$-GCN4 with TEV and 6×His (SEQ ID NO: 5))—exemplary amino acid sequence of a modified HCMV gB protein from these studies comprising, as compared to wild type Merlin HCMV gB (SEQ ID NO: 1):

Predicted Signal peptide residues M1-A22 (underlined, would be removed in mature sequence);
Fusion Loop 1 modifications $^{155}$YIH$^{157}$ to $^{155}$GHR$^{157}$ (underlined);
Fusion Loop 2 modifications $^{240}$WLY$^{242}$ to $^{240}$AFH$^{242}$ (underlined);
Furin Cleavage Site residues R457S and R460S (underlined);
A truncation of the MPR residues (i.e., truncation of residues D699-P751, meaning truncation of the residues c-terminal to residue E698 which is in bold);
Insertion of two proline residues c-terminally adjacent to residue E698 (underlined);
Insertion of GCN4 sequence SEQ ID NO: 2 C-terminally adjacent to the c-terminal-most inserted proline residue (double underlined);
Insertion of SEQ ID NO: 5 (i.e., a TEV cleavage site (underlined) and 6×His tag (double underlined) C-terminally adjacent to the GCN4 sequence).

```
        10         20         30         40         50         60
MESRIWCLVV CVNLCIVCLG AAVSSSSTRG TSATHSHHSS HTTSAAHSRS GSVSQRVTSS
```

```
                70          80          90         100         110         120
        QTVSHGVNET  IYNTTLKYGD  VVGVNTTKYP  YRVCSMAQGT  DLIRFERNIV  CTSMKPINED 130         140         150         160         170         180
        LDEGIMVVYK  RNIVAHTFKV  RVYQKVLTFR  RSYAGHRTTY  LLGSNTEYVA  PPMWEIHHIN
                                                ———

190         200         210         220         230         240
        SHSQCYSSYS  RVIAGTVFVA  YHRDSYENKT  MQLMPDDYSN  THSTRYVTVK  DQWHSRGSTA
                                                                              —
               250         260         270         280         290         300
        FHRETCNLNC  MVTITTARSK  YPYHFFATST  GDVVDISPFY  NGTNRNASYF  GENADKFFIF
        —

310         320         330         340         350         360
        PNYTIVSDFG  RPNSALETHR  LVAFLERADS  VISWDIQDEK  NVTCQLTFWE  ASERTIRSEA 370         380         390         400         410         420
        EDSYHFSSAK  MTATFLSKKQ  EVNMSDSALD  CVRDEAINKL  QQIFNTSYNQ  TYEKYGNVSV 430         440         450         460         470         480
        FETTGGLVVF  WQGIKQKSLV  ELERLANRSS  LNLTHNSTKS  STDGNNATHL  SNMESVHNLV
                                           —————————

490         500         510         520         530         540
        YAQLQFTYDT  LRGYINRALA  QIAEAWCVDQ  RRTLEVFKEL  SKINPSAILS  AIYNKPIAAR 550         560         570         580         590         600
        FMGDVLGLAS  CVTINQTSVK  VLRDMNVKES  PGRCYSRPVV  IFNFANSSYV  QYGQLGEDNE 610         620         630         640         650         660
        ILLGNHRTEE  CQLPSLKIFI  AGNSAYEYVD  YLFKRMIDLS  SISTVDSMIA  LDIDPLENTD 670         680         690         700         710         720
        FRVLELYSQK  ELRSSNVFDL  EEIMREFNSY  KQRVKYVEPP  RMKQLEDKVE  ELLSKNYHLE
                                                   —   ——————————  ——————————
               730         740
        NEVARLKKLV  GERENLYFQG  GHHHHHH
        ——————————  ——————————
```

SEQ ID NO: 12—the wild type EBV gB sequence published as UniProtKB Accession P03188 (entry 110 dated Dec. 11, 2019) and that is characterized by having the following features:

Predicted Signal peptide residues M1-G21 (underlined, would be removed in mature sequence);
Fusion Loop 1 residues [111]GWY[113] (underlined);
Fusion Loop 2 residues [193]WLIW[196] (underlined);
Furin Cleavage Site residues R428 to R431 (underlined);
Domain III Coiled-coil Region residues N455-1500 underlined with residues N455-K488 being double underlined;
MPR residues N680-P732 residues (underlined) with residue Q705 in bold;
Transmembrane domain residues F733-T753 (double underlined);
Cytoplasmic domain is from residues R754-F857 (underlined).

```
                        10          20          30          40          50          60
                MTRRRVLSVV  VLLAALACRL  GAQTPEQPAP  PATTVQPTAT  RQQTSFPFRV  CELSSHGDLF
                —————————— —————————— ——

70          80          90         100         110         120
                RFSSDIQCPS  FGTRENHTEG  LLMVFKDNII  PYSFKVRSYT  KIVTNILIYN  GWYADSVTNR
                                                                                   ———
                       130         140         150         160         170         180
                HEEKFSVDSY  ETDQMDTIYQ  CYNAVKMTKD  GLTRVYVDRD  GVNITVNLKP  TGGLANGVRR 190         200         210         220         230         240
                YASQTELYDA  PGWLIWTYRT  RTTVNCLITD  MMAKSNSPFD  FFVTTTGQTV  EMSPFYDGKN
                             ————

250         260         270         280         290         300
                KETFHERADS  PHVRTNYKIV  DYDNRGTNPQ  GERRAFLDKG  TYTLSWKLEN  RTAYCPLQHW 310         320         330         340         350         360
                QTFDSTIATE  TGKSIHFVTD  EGTSSFVTNT  TVGIELPDAF  KCIEEQVNKT  MHEKYEAVQD 370         380         390         400         410         420
                RYTKGQEAIT  YFITSGGLLL  AWLPLTPRSL  ATVKNLTELT  TPTSSPPSSP  SPPAPSAARG 430         440         450         460         470         480
                STPAAVLRRR  RRDAGNATTP  VPPTAPGKSL  GTLNNPATVQ  IQFAYDSLRR  QINRMLGDLA
                      ————                              ——————  ——————————  ——————————
                       490         500         510         520         530         540
                RAWCLEQKRQ  NMVLRELTKI  NPTTVMSSIY  GKAVAAKRLG  DVISVSQCVP  VNQATVTLRK
                ——————————

550         560         570         580         590         600
                SMRVPGSETM  CYSRPLVSFS  FINDTKTYEG  QLGTDNEIFL  TKKMTEVCQA  TSQYYFQSGN
```

-continued

```
         610        620        630        640        650        660
   EIHVYNDYHH FKTIELDGIA TLQTFISLNT SLIENIDFAS LELYSRDEQR ASNVFDLEGI 670        680        690        700        710        720
   FREYNFQAQN IAGLRKDLDN AVSNGRNQFV DGLGELMDSL GSVGQSITNL VSTVGGLFSS 730        740        750        760        770        780
   LVSGFISFFK NPFGGMLILV LVAGVVILVI SLTRRTRQMS QQPVQMLYPG IDELAQQHAS 790        800        810        820        830        840
   GEGPGINPIS KTELQAIMLA LHEQNQEQKR AAQRAAGPSV ASRALQAARD RFPGLRRRRY 850        857
   HDPETAAALL GEAETEF
```

SEQ ID NO: 13 (EBV-GCN4)—exemplary amino acid sequence of a modified EBV gB protein from these studies comprising, as compared to EBV gB sequence SEQ ID NO: 12 above:
- Predicted Signal peptide residues M1-G21 (underlined, would be removed in mature sequence);
- Fusion Loop 1 modifications $^{111}$GWY$^{113}$ to $^{111}$GHR$^{113}$ (underlined);
- Fusion Loop 2 modifications $^{193}$WLIW$^{196}$ to $^{193}$RVEA$^{196}$ (underlined);
- Furin Cleavage Site modifications of residues $^{428}$RRRR$^{431}$ to $^{428}$SSR$^{5431}$ (underlined);
- A deletion of the MPR residues c-terminal to Q705 (which is in bold) (meaning the MPR is truncated (via deletion of residues 5706-P732) and the transmembrane domain and cytoplasmic domain (residues F733-F857) are also deleted);
- Insertion of two proline residues c-terminally adjacent to residue Q705 (underlined);
- Insertion of GCN4 sequence SEQ ID NO: 2 C-terminally adjacent to the c-terminal-most inserted proline residue (double underlined);
- Insertion of SEQ ID NO: 5 (i.e., a TEV cleavage site (underlined) and 6×His tag (double underlined) C-terminally adjacent to the GCN4 sequence).

```
            10         20         30         40         50         60
   MTRRRVLSVV VLLAALACRL GAQTPEQPAP PATTVQPTAT RQQTSFPFRV CELSSHGDLF 70         80         90        100        110        120
   RFSSDIQCPS FGTRENHTEG LLMVFKDNII PYSFKVRSYT KIVTNILIYN GHRADSVTNR 130        140        150        160        170        180
   HEEKFSVDSY ETDQMDTIYQ CYNAVKMTKD GLTRVYVDRD GVNITVNLKP TGGLANGVRR 190        200        210        220        230        240
   YASQTELYDA PGRVEATYRT RTTVNCLITD MMAKSNSPFD FFVTTTGQTV EMSPFYDGKN 250        260        270        280        290        300
   KETFHERADS FHVRTNYKIV DYDNRGTNPQ GERRAFLDKG TYTLSWKLEN RTAYCPLQHW 310        320        330        340        350        360
   QTFDSTIATE TGKSIHFVTD EGTSSFVTNT TVGIELPDAF KCIEEQVNKT MHEKYEAVQD 370        380        390        400        410        420
   RYTKGQEAIT YFITSGGLLL AWLPLTPRSL ATVKNLTELT TPTSSPPSSP SPPAPSAARG 430        440        450        460        470        480
   STPAAVLSSR SRDAGNATTP VPPTAPGKSL GTLNNPATVQ IQFAYDSLRR QINRMLGDLA 490        500        510        520        530        540
   RAWCLEQKRQ NMVLRELTKI NPTTVMSSIY GKAVAAKRLG DVISVSQCVP VNQATVTLRK 550        560        570        580        590        600
   SMRVPGSETM CYSRPLVSFS FINDTKTYEG QLGTDNEIFL TKKMTEVCQA TSQYYFQSGN 610        620        630        640        650        660
   EIHVYNDYHH FKTIELDGIA TLQTFISLNT SLIENIDFAS LELYSRDEQR ASNVFDLEGI 670        680        690        700        710        720
   FREYNFQAQN IAGLRKDLDN AVSNGRNQFV DGLGELMDSL GSVGQPPRMK QLEDKVEELL 730        740        750
   SKNYHLENEV ARLKKLVGER ENLYFQGGHH HHHH
```

SEQ ID NO: 14 (AD169-GCN4)—exemplary amino acid sequence of a modified HCMV AD169 strain gB protein from these studies comprising, as compared to HCMV AD169 gB sequence SEQ ID NO: 6 above:
- Predicted Signal peptide residues M1-A22 (underlined, would be removed in mature sequence);
- Fusion Loop 1 modifications $^{155}$YIY$^{157}$ to $^{155}$GHR$^{157}$ (underlined);
- Fusion Loop 2 modifications $^{240}$WLY$^{242}$ to $^{240}$AFH$^{242}$ (underlined);

Furin Cleavage Site modifications of residues $^{456}$RTRR$^{459}$ to $^{456}$TTQT$^{459}$ (underlined);

A truncation of the residues c-terminal to MPR residue K723 (residue in bold) (i.e., cleavage of the C-terminal end of the MPR and removal of the transmembrane and cytoplasmic domains);

Insertion of two proline residues c-terminally adjacent to residue K723 (underlined);

Insertion of GCN4 sequence SEQ ID NO: 2 C-terminally adjacent to the c-terminal-most inserted proline residue (double underlined);

Insertion of SEQ ID NO: 5 (i.e., a TEV cleavage site (underlined) and 6×His tag (double underlined) C-terminally adjacent to the GCN4 sequence).

```
          10         20         30         40         50         60
  MESRIWCLVV CVNLCIVCLG AAVSSSSTSH ATSSTHNGSH TSRTTSAQTR SVYSQHVTSS 70         80         90        100        110        120
  EAVSHRANET IYNTTLKYGD VVGVNTTKYP YRVCSMAQGT DLIRFERNII CTSMKPINED 130        140        150        160        170        180
  LDEGIMVVYK RNIVAHTFKV RVYQKVLTFR RSYAGHRTTY LLGSNTEYVA PPMWEIHHIN 190        200        210        220        230        240
  KFAQCYSSYS RVIGGTVFVA YHRDSYENKT MQLIPDDYSN THSTRYVTVK DQWHSRGSTA 250        260        270        280        290        300
  FHRETCNLNC MLTITTARSK YPYHFFATST GDVVYISPFY NGTNRNASYF GENADKFFIF 310        320        330        340        350        360
  PNYTIVSDFG RPNAAPETHR LVAFLERADS VISWDIQDEK NVTCQLTFWE ASERTIRSEA 370        380        390        400        410        420
  EDSYHFSSAK MTATFLSKKQ EVNMSDSALD CVRDEAINKL QQIFNTSYNQ TYEKYGNVSV 430        440        450        460        470        480
  FETSGGLVVF WQGIKQKSLV ELERLANRSS LNITHTTQTS TSDNNTTHLS SMESVHNLVY 490        500        510        520        530        540
  AQLQFTYDTL RGYINRALAQ IAEAWCVDQR RTLEVFKELS KINPSAILSA IYNKPIAARF 550        560        570        580        590        600
  MGDVLGLASC VTINQTSVKV LRDMNVKESP GRCYSRPVVI FNFANSSYVQ YGQLGEDNEI 610        620        630        640        650        660
  LLGNHRTEEC QLPSLKIFIA GNSAYEYVDY LFKRMIDLSS ISTVDSMIAL DIDPLENTDF 670        680        690        700        710        720
  RVLELYSQKE LRSSNVFDLE EIMREFNSYK QRVKYVEDKV VDPLPPYLKG LDDLMSGLGA 730        740        750
  AGKPPRMKQL EDKVEELLSK NYHLENEVAR LKKLVGEREN LYFQGGHHHH HH
```

(gB'-R497P-GCN4)-residues 23-759 of SEQ ID NO: 3 further modified by the R497P substitution (is R475P numbered according to this sequence).

SEQ ID NO: 15

VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINPALAQI

AEAWCVDQRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (gB'-W505P-GCN4)-residues 23-759 ofSEQ ID NO: 3 further modified by the W506P substitution (is W484P numbered according to this sequence).

```
                                                        SEQ ID NO: 16
VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

AEAPCVDQRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (gB'-C507P-GCN4)-residues 23-759 ofSEQ ID NO: 3 further modified by the
C507P substitution (is C485P numbered according to this sequence).
                                                        SEQ ID NO: 17
VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

AEAWPVDQRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (gB'-D509P-GCN4) residues 23-759 ofSEQ ID NO: 3 further modified by the
D509P substitution (is D487P numbered according to this sequence).
                                                        SEQ ID NO: 18
VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

AEAWCVPQRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE
```

-continued

IMREFNSYKQRVKYVEDKVVDPLPPYLKGLDDLMSGLGAAGKPPRMKQLEDKVEELLSKN

YHLENEVARLKKLVGER (gB'-Q510P-GCN4)-residues 23-759 ofSEQ ID NO: 3 further modified by the
Q51 OP substitution (is Q488P numbered according to this sequence).
SEQ ID NO: 19

VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

AEAWCVDPRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (gB'-R511P-GCN4)-residues 23-759 of SEQ ID NO: 3 further modified by the
R511P substitution (is R489P numbered according to this sequence).
SEQ ID NO: 20

VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

AEAWCVDQPRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (gB'-W506P-Q510P-GCN4)-residues 23-759 of SEQ ID NO: 3 further modified
by the two W506P and Q510P substitutions (are W484P and Q488P numbered
according to this sequence).
SEQ ID NO: 21

VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

-continued

AEAPCVDPRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (gB'-D509P-Q510P-GCN4)-residues 23-759 of SEQ ID NO: 3 further modified
by the two D509P and Q510P substitutions (are D487P and Q488P numbered
according to this sequence).
SEQ ID NO: 22

VSSSSTRGTSATHSHHSSHTTSAAHSRSGSVSQRVTSSQTVSHGVNETIYNTTLKYGDVV

GVNTTKYPYRVCSMAQGTDLIRFERNIVCTSMKPINEDLDEGIMVVYKRNIVAHTFKVRV

YQKVLTFRRSYAGHRTTYLLGSNTEYVAPPMWEIHHINSHSQCYSSYSRVIAGTVFVAYH

RDSYENKTMQLMPDDYSNTHSTRYVTVKDQWHSRGSTAFHRETCNLNCMVTITTARSKYP

YHFFATSTGDVVDISPFYNGTNRNASYFGENADKFFIFPNYTIVSDFGRPNSALETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETTGGLVVFWQGIKQKSLVEL

ERLANRSSLNLTHNSTKSSTDGNNATHLSNMESVHNLVYAQLQFTYDTLRGYINRALAQI

AEAWCVPPRRTLEVFKELSKINPSAILSAIYNKPIAARFMGDVLGLASCVTINQTSVKVL

RDMNVKESPGRCYSRPVVIFNFANSSYVQYGQLGEDNEILLGNHRTEECQLPSLKIFIAG

NSAYEYVDYLFKRMIDLSSISTVDSMIALDIDPLENTDFRVLELYSQKELRSSNVFDLEE

IMREFNSYKQRVKYVEDKVVDPLPPYLKGLDDLMSGLGAAGKPPRMKQLEDKVEELLSKN

YHLENEVARLKKLVGER (AD169-R496P-GCN4)-residues 23-758 of SEQ ID NO: 14 further modified by
the R496P substitution (is R474P numbered according to this sequence).
SEQ ID NO: 23

VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINPALAQIA

EAWCVDQRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER (AD169-W505P-GCN4)-residues 23-758 of SEQ ID NO: 14 further modified by
the W505P substitution (is W483P numbered according to this sequence).
SEQ ID NO: 24

VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

-continued

```
YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAPCVDQRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER
```

(AD169-C506P-GCN4)-residues 23-758 of SEQ ID NO: 14 further modified by
the C506P substitution (is C484P numbered according to this sequence).

SEQ ID NO: 25

```
VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAWPVDQRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER
```

(AD169-D508P-GCN4)-residues 23-758 of SEQ ID NO: 14 further modified by
the D508P substitution (is D486P numbered according to this sequence).

SEQ ID NO: 26

```
VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAWCVPQRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER
```

(AD169-Q509P-GCN4)-residues 23-758 ofSEQ ID NO: 14 further modified by
the Q509P substitution (is Q487P numbered according to this sequence).

SEQ ID NO: 27

```
VSSSSTSHATSSTHNGSHTSRTTSAQTRSVYSQHVTSSEAVSHRANETIYNTTLKYGDVV
```

-continued

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAWCVDPRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER (AD169-R510P-GCN4)-residues 23-758 of SEQ ID NO: 14 further modified by
the R510P substitution (is R488P numbered according to this sequence).
SEQ ID NO: 28

VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAWCVDQPRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER (AD169-W505P-Q509P-GCN4)-residues 23-758 of SEQ ID NO: 14 further modified
by the two W505P and Q509P substitutions (are W483P and Q487P numbered
according to this sequence).
SEQ ID NO: 29

VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAPCVDPRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER (AD169-D508P-Q509P-GCN4)-residues 23-758 of SEQ ID NO: 14 further modified
by the two D508P and Q509P substitutions (are D486P and Q487P numbered
according to this sequence).

SEQ ID NO: 30

VSSSSTSHATSSTHNGSHTSRTTSAQTRSVYSQHVTSSEAVSHRANETIYNTTLKYGDVV

GVNTTKYPYRVCSMAQGTDLIRFERNIICTSMKPINEDLDEGIMVVYKRNIVAHTFKVRV

YQKVLTFRRSYAGHRTTYLLGSNTEYVAPPMWEIHHINKFAQCYSSYSRVIGGTVFVAYH

RDSYENKTMQLIPDDYSNTHSTRYVTVKDQWHSRGSTAFHRETCNLNCMLTITTARSKYP

YHFFATSTGDVVYISPFYNGTNRNASYFGENADKFFIFPNYTIVSDFGRPNAAPETHRLV

AFLERADSVISWDIQDEKNVTCQLTFWEASERTIRSEAEDSYHFSSAKMTATFLSKKQEV

NMSDSALDCVRDEAINKLQQIFNTSYNQTYEKYGNVSVFETSGGLVVFWQGIKQKSLVEL

ERLANRSSLNITHTTQTSTSDNNTTHLSSMESVHNLVYAQLQFTYDTLRGYINRALAQIA

EAWCVPPRRTLEVFKELSKINPSAILSAIYNKPIAARFMGDVLGLASCVTINQTSVKVLR

DMNVKESPGRCYSRPVVIFNFANSSYVQYGQLGEDNEILLGNHRTEECQLPSLKIFIAGN

SAYEYVDYLFKRMIDLSSISTVDSMIALDIDPLENTDFRVLELYSQKELRSSNVFDLEEI

MREFNSYKQRVKYVEDKVVDPLPPYLKGLDDLMSGLGAAGKPPRMKQLEDKVEELLSKNY

HLENEVARLKKLVGER

---

The invention claimed is:

1. A modified human cytomegalovirus (HCMV) glycoprotein B (gB) protein comprising a trimerization domain operably linked c-terminal to the residue corresponding to 724 numbered according to SEQ ID NO: 1, wherein an amino acid linker is between the residue corresponding to 724, numbered according to SEQ ID NO: 1, and the trimerization domain, wherein the trimerization domain is a GCN4 Leucine Zipper (GCN4) domain, and wherein the modified HCMV gB protein is in pre-fusogenic conformation, and wherein the modified HCMV gB protein comprises a proline substitution of one or more residues corresponding to N478-R511 numbered according to SEQ ID NO: 1.

2. The modified HCMV gB protein of claim 1, further comprising a purification tag.

3. The modified HCMV gB protein of claim 1 that is:
   (I) a modified HCMV gB protein comprising R497P, W506P, C507P, D509P, Q510P, R511P, W506P and Q510P, or D509P and Q510P, or combinations thereof; numbered according to SEQ ID NO: 1; or
   (II) a modified HCMV gB protein comprising R496P, W505P, C506P, D508P, Q509P, R510P, W505P and Q509P, or D508P and Q509P, or combinations thereof; numbered according to SEQ ID NO: 6.

4. The modified HCMV gB protein of claim 1 comprising an amino acid sequence with at least 92%, 93%, 94%, 95%, 96%, 97%, 98%, 99%, or 100% sequence identity to SEQ ID NO: 3 or SEQ ID NO: 4.

5. The modified HCMV gB protein of claim 1 operably linked to a carrier, wherein the carrier is a nanoparticle.

6. An isolated nucleic acid comprising a polynucleotide sequence encoding the modified HCMV gB protein of claim 1.

7. An immunogenic composition comprising the modified HCMV gB protein of claim 1.

8. The immunogenic composition of claim 7, further comprising an adjuvant.

9. A recombinant vector comprising the nucleic acid of claim 6.

10. An isolated host cell comprising the nucleic acid of claim 6, wherein the polynucleotide is DNA and stably incorporated into the genomic DNA of the host cell.

11. An immunogenic composition comprising the modified HCMV gB protein of claim 1, and at least one additional antigenic protein.

12. The immunogenic composition of claim 11, wherein the at least one additional antigenic protein is gO, gH, gL, pUL128, pUL130, pUL131, pp65, IE1, or an antigenic fragment thereof.

13. A method of inhibiting HCMV entry into a cell, comprising contacting the cell with the modified HCMV gB protein of claim 1.

14. A method of inducing an immune response against HCMV in a subject, comprising administering to the subject an immunologically effective amount of the immunogenic composition of claim 7.

* * * * *

SEQUENCE LISTING

<160> NUMBER OF SEQ ID NOS: 30

<210> SEQ ID NO 1
<211> LENGTH: 907
<212> TYPE: PRT
<213> ORGANISM: Human cytomegalovirus

<400> SEQUENCE: 1

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Tyr
145                 150                 155                 160

Leu Leu Gly Ser Asn Thr Glu Tyr Val Ala Pro Pro Met Trp Glu Ile
```

```
                 165                 170                 175
His His Ile Asn Ser His Ser Gln Cys Tyr Ser Ser Tyr Ser Arg Val
                 180                 185                 190

Ile Ala Gly Thr Val Phe Val Ala Tyr His Arg Asp Ser Tyr Glu Asn
                 195                 200                 205

Lys Thr Met Gln Leu Met Pro Asp Asp Tyr Ser Asn Thr His Ser Thr
                 210                 215                 220

Arg Tyr Val Thr Val Lys Asp Gln Trp His Ser Arg Gly Ser Thr Trp
225                  230                 235                 240

Leu Tyr Arg Glu Thr Cys Asn Leu Asn Cys Met Val Thr Ile Thr Thr
                 245                 250                 255

Ala Arg Ser Lys Tyr Pro Tyr His Phe Phe Ala Thr Ser Thr Gly Asp
                 260                 265                 270

Val Val Asp Ile Ser Pro Phe Tyr Asn Gly Thr Asn Arg Asn Ala Ser
                 275                 280                 285

Tyr Phe Gly Glu Asn Ala Asp Lys Phe Phe Ile Phe Pro Asn Tyr Thr
                 290                 295                 300

Ile Val Ser Asp Phe Gly Arg Pro Asn Ser Ala Leu Glu Thr His Arg
305                  310                 315                 320

Leu Val Ala Phe Leu Glu Arg Ala Asp Ser Val Ile Ser Trp Asp Ile
                 325                 330                 335

Gln Asp Glu Lys Asn Val Thr Cys Gln Leu Thr Phe Trp Glu Ala Ser
                 340                 345                 350

Glu Arg Thr Ile Arg Ser Glu Ala Glu Asp Ser Tyr His Phe Ser Ser
                 355                 360                 365

Ala Lys Met Thr Ala Thr Phe Leu Ser Lys Lys Gln Glu Val Asn Met
                 370                 375                 380

Ser Asp Ser Ala Leu Asp Cys Val Arg Asp Glu Ala Ile Asn Lys Leu
385                  390                 395                 400

Gln Gln Ile Phe Asn Thr Ser Tyr Asn Gln Thr Tyr Glu Lys Tyr Gly
                 405                 410                 415

Asn Val Ser Val Phe Glu Thr Thr Gly Gly Leu Val Val Phe Trp Gln
                 420                 425                 430

Gly Ile Lys Gln Lys Ser Leu Val Glu Leu Glu Arg Leu Ala Asn Arg
                 435                 440                 445

Ser Ser Leu Asn Leu Thr His Asn Arg Thr Lys Arg Ser Thr Asp Gly
                 450                 455                 460

Asn Asn Ala Thr His Leu Ser Asn Met Glu Ser Val His Asn Leu Val
465                  470                 475                 480

Tyr Ala Gln Leu Gln Phe Thr Tyr Asp Thr Leu Arg Gly Tyr Ile Asn
                 485                 490                 495

Arg Ala Leu Ala Gln Ile Ala Glu Ala Trp Cys Val Asp Gln Arg Arg
                 500                 505                 510

Thr Leu Glu Val Phe Lys Glu Leu Ser Lys Ile Asn Pro Ser Ala Ile
                 515                 520                 525

Leu Ser Ala Ile Tyr Asn Lys Pro Ile Ala Ala Arg Phe Met Gly Asp
                 530                 535                 540

Val Leu Gly Leu Ala Ser Cys Val Thr Ile Asn Gln Thr Ser Val Lys
545                  550                 555                 560

Val Leu Arg Asp Met Asn Val Lys Glu Ser Pro Gly Arg Cys Tyr Ser
                 565                 570                 575

Arg Pro Val Val Ile Phe Asn Phe Ala Asn Ser Ser Tyr Val Gln Tyr
                 580                 585                 590
```

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
        610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
            645                 650                 655

Glu Asn Thr Asp Phe Arg Val Leu Glu Leu Tyr Ser Gln Lys Glu Leu
        660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
        690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
            725                 730                 735

Val Ala Ser Val Val Glu Gly Val Ala Thr Phe Leu Lys Asn Pro Phe
        740                 745                 750

Gly Ala Phe Thr Ile Ile Leu Val Ala Ile Ala Val Val Ile Ile Thr
            755                 760                 765

Tyr Leu Ile Tyr Thr Arg Gln Arg Arg Leu Cys Thr Gln Pro Leu Gln
        770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
            805                 810                 815

Ser Val Tyr Asn Ser Gly Arg Lys Gly Pro Gly Pro Pro Ser Ser Asp
        820                 825                 830

Ala Ser Thr Ala Ala Pro Pro Tyr Thr Asn Glu Gln Ala Tyr Gln Met
            835                 840                 845

Leu Leu Ala Leu Ala Arg Leu Asp Ala Glu Gln Arg Ala Gln Gln Asn
        850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
            885                 890                 895

His Leu Lys Asp Ser Asp Glu Glu Asn Val
            900                 905

<210> SEQ ID NO 2
<211> LENGTH: 33
<212> TYPE: PRT
<213> ORGANISM: Artificial Sequence
<220> FEATURE:
<223> OTHER INFORMATION: GCN4 Leucine Zipper Domain

<400> SEQUENCE: 2

Arg Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu Val Gly Glu
            20                  25                  30

Arg

<210> SEQ ID NO 3
<211> LENGTH: 759
<212> TYPE: PRT
<213> ORGANISM: Artificial Sequence
<220> FEATURE:
<223> OTHER INFORMATION: Modified HCMV gB

<400> SEQUENCE: 3

```
Met Glu Ser Arg Ile Trp Cys Leu Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Gly His Arg Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Ala
225                 230                 235                 240

Phe His Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365
```

```
Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Thr Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Leu Thr His Asn Ser Thr Lys Ser Ser Thr Asp Gly
450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
690                 695                 700

Leu Pro Pro Tyr Leu Lys Gly Leu Asp Asp Leu Met Ser Gly Leu Gly
705                 710                 715                 720

Ala Ala Gly Lys Pro Pro Arg Met Lys Gln Leu Glu Asp Lys Val Glu
                725                 730                 735

Glu Leu Leu Ser Lys Asn Tyr His Leu Glu Asn Glu Val Ala Arg Leu
            740                 745                 750

Lys Lys Leu Val Gly Glu Arg
            755

<210> SEQ ID NO 4
<211> LENGTH: 773
<212> TYPE: PRT
```

<213> ORGANISM: Artificial Sequence
<220> FEATURE:
<223> OTHER INFORMATION: Modified HCMV gB

<400> SEQUENCE: 4

Met Glu Ser Arg Ile Trp Cys Leu Val Val Cys Val Asn Leu Cys Ile
1 5 10 15

Val Cys Leu Gly Ala Ala Val Ser Ser Ser Ser Thr Arg Gly Thr Ser
20 25 30

Ala Thr His Ser His His Ser Ser His Thr Thr Ser Ala Ala His Ser
35 40 45

Arg Ser Gly Ser Val Ser Gln Arg Val Thr Ser Ser Gln Thr Val Ser
50 55 60

His Gly Val Asn Glu Thr Ile Tyr Asn Thr Thr Leu Lys Tyr Gly Asp
65 70 75 80

Val Val Gly Val Asn Thr Thr Lys Tyr Pro Tyr Arg Val Cys Ser Met
85 90 95

Ala Gln Gly Thr Asp Leu Ile Arg Phe Glu Arg Asn Ile Val Cys Thr
100 105 110

Ser Met Lys Pro Ile Asn Glu Asp Leu Asp Glu Gly Ile Met Val Val
115 120 125

Tyr Lys Arg Asn Ile Val Ala His Thr Phe Lys Val Arg Val Tyr Gln
130 135 140

Lys Val Leu Thr Phe Arg Arg Ser Tyr Ala Gly His Arg Thr Thr Tyr
145 150 155 160

Leu Leu Gly Ser Asn Thr Glu Tyr Val Ala Pro Pro Met Trp Glu Ile
165 170 175

His His Ile Asn Ser His Ser Gln Cys Tyr Ser Ser Tyr Ser Arg Val
180 185 190

Ile Ala Gly Thr Val Phe Val Ala Tyr His Arg Asp Ser Tyr Glu Asn
195 200 205

Lys Thr Met Gln Leu Met Pro Asp Asp Tyr Ser Asn Thr His Ser Thr
210 215 220

Arg Tyr Val Thr Val Lys Asp Gln Trp His Ser Arg Gly Ser Thr Ala
225 230 235 240

Phe His Arg Glu Thr Cys Asn Leu Asn Cys Met Val Thr Ile Thr Thr
245 250 255

Ala Arg Ser Lys Tyr Pro Tyr His Phe Phe Ala Thr Ser Thr Gly Asp
260 265 270

Val Val Asp Ile Ser Pro Phe Tyr Asn Gly Thr Asn Arg Asn Ala Ser
275 280 285

Tyr Phe Gly Glu Asn Ala Asp Lys Phe Phe Ile Phe Pro Asn Tyr Thr
290 295 300

Ile Val Ser Asp Phe Gly Arg Pro Asn Ser Ala Leu Glu Thr His Arg
305 310 315 320

Leu Val Ala Phe Leu Glu Arg Ala Asp Ser Val Ile Ser Trp Asp Ile
325 330 335

Gln Asp Glu Lys Asn Val Thr Cys Gln Leu Thr Phe Trp Glu Ala Ser
340 345 350

Glu Arg Thr Ile Arg Ser Glu Ala Glu Asp Ser Tyr His Phe Ser Ser
355 360 365

Ala Lys Met Thr Ala Thr Phe Leu Ser Lys Lys Gln Glu Val Asn Met
370 375 380

Ser Asp Ser Ala Leu Asp Cys Val Arg Asp Glu Ala Ile Asn Lys Leu

```
                385                 390                 395                 400
        Gln Gln Ile Phe Asn Thr Ser Tyr Asn Gln Thr Tyr Glu Lys Tyr Gly
                        405                 410                 415

Asn Val Ser Val Phe Glu Thr Thr Gly Gly Leu Val Val Phe Trp Gln
                        420                 425                 430

Gly Ile Lys Gln Lys Ser Leu Val Glu Leu Glu Arg Leu Ala Asn Arg
                        435                 440                 445

Ser Ser Leu Asn Leu Thr His Asn Ser Thr Lys Ser Ser Thr Asp Gly
        450                 455                 460

Asn Asn Ala Thr His Leu Ser Asn Met Glu Ser Val His Asn Leu Val
        465                 470                 475                 480

Tyr Ala Gln Leu Gln Phe Thr Tyr Asp Thr Leu Arg Gly Tyr Ile Asn
                        485                 490                 495

Arg Ala Leu Ala Gln Ile Ala Glu Ala Trp Cys Val Asp Gln Arg Arg
                        500                 505                 510

Thr Leu Glu Val Phe Lys Glu Leu Ser Lys Ile Asn Pro Ser Ala Ile
                        515                 520                 525

Leu Ser Ala Ile Tyr Asn Lys Pro Ile Ala Arg Phe Met Gly Asp
        530                 535                 540

Val Leu Gly Leu Ala Ser Cys Val Thr Ile Asn Gln Thr Ser Val Lys
        545                 550                 555                 560

Val Leu Arg Asp Met Asn Val Lys Glu Ser Pro Gly Arg Cys Tyr Ser
                        565                 570                 575

Arg Pro Val Val Ile Phe Asn Phe Ala Asn Ser Ser Tyr Val Gln Tyr
                        580                 585                 590

Gly Gln Leu Gly Glu Asp Asn Glu Ile Leu Leu Gly Asn His Arg Thr
                        595                 600                 605

Glu Glu Cys Gln Leu Pro Ser Leu Lys Ile Phe Ile Ala Gly Asn Ser
                        610                 615                 620

Ala Tyr Glu Tyr Val Asp Tyr Leu Phe Lys Arg Met Ile Asp Leu Ser
        625                 630                 635                 640

Ser Ile Ser Thr Val Asp Ser Met Ile Ala Leu Asp Ile Asp Pro Leu
                        645                 650                 655

Glu Asn Thr Asp Phe Arg Val Leu Glu Leu Tyr Ser Gln Lys Glu Leu
                        660                 665                 670

Arg Ser Ser Asn Val Phe Asp Leu Glu Glu Ile Met Arg Glu Phe Asn
                        675                 680                 685

Ser Tyr Lys Gln Arg Val Lys Tyr Val Glu Asp Lys Val Asp Pro
        690                 695                 700

Leu Pro Pro Tyr Leu Lys Gly Leu Asp Asp Leu Met Ser Gly Leu Gly
        705                 710                 715                 720

Ala Ala Gly Lys Pro Pro Arg Met Lys Gln Leu Glu Asp Lys Val Glu
                        725                 730                 735

Glu Leu Leu Ser Lys Asn Tyr His Leu Glu Asn Glu Val Ala Arg Leu
                        740                 745                 750

Lys Lys Leu Val Gly Glu Arg Glu Asn Leu Tyr Phe Gln Gly Gly His
                        755                 760                 765

His His His His His
                770

<210> SEQ ID NO 5
<211> LENGTH: 14
<212> TYPE: PRT
<213> ORGANISM: Artificial Sequence
```

<220> FEATURE:
<223> OTHER INFORMATION: TEV cleavage site and 6xHis tag

<400> SEQUENCE: 5

Glu Asn Leu Tyr Phe Gln Gly Gly His His His His His His
1               5                   10

<210> SEQ ID NO 6
<211> LENGTH: 906
<212> TYPE: PRT
<213> ORGANISM: Human cytomegalovirus

<400> SEQUENCE: 6

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

```
Gln Asp Glu Lys Asn Val Thr Cys Gln Leu Thr Phe Trp Glu Ala Ser
                340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
        370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
```

```
                        755                 760                 765
Leu Ile Tyr Thr Arg Gln Arg Arg Leu Cys Thr Gln Pro Leu Gln Asn
            770                 775                 780
Leu Phe Pro Tyr Leu Val Ser Ala Asp Gly Thr Thr Val Thr Ser Gly
785                 790                 795                 800
Ser Thr Lys Asp Thr Ser Leu Gln Ala Pro Pro Ser Tyr Glu Glu Ser
                805                 810                 815
Val Tyr Asn Ser Gly Arg Lys Gly Pro Gly Pro Pro Ser Ser Asp Ala
            820                 825                 830
Ser Thr Ala Ala Pro Pro Tyr Thr Asn Glu Gln Ala Tyr Gln Met Leu
        835                 840                 845
Leu Ala Leu Ala Arg Leu Asp Ala Glu Gln Arg Ala Gln Gln Asn Gly
    850                 855                 860
Thr Asp Ser Leu Asp Gly Gln Thr Gly Thr Gln Asp Lys Gly Gln Lys
865                 870                 875                 880
Pro Asn Leu Leu Asp Arg Leu Arg His Arg Lys Asn Gly Tyr Arg His
                885                 890                 895
Leu Lys Asp Ser Asp Glu Glu Glu Asn Val
            900                 905

<210> SEQ ID NO 7
<211> LENGTH: 8
<212> TYPE: PRT
<213> ORGANISM: Artificial Sequence
<220> FEATURE:
<223> OTHER INFORMATION: FLAG Tag

<400> SEQUENCE: 7

Asp Tyr Lys Asp Asp Asp Asp Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Streptavidin Tag

<400> SEQUENCE: 8

Ala Trp Arg His Pro Gln Phe Gly Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Streptavidin tag

<400> SEQUENCE: 9

Trp Ser His Pro Gln Phe Glu Lys
1               5

<210> SEQ ID NO 10
<211> LENGTH: 28
<212> TYPE: PRT
<213> ORGANISM: Artificial Sequence
<220> FEATURE:
<223> OTHER INFORMATION: Streptavidin tag

<400> SEQUENCE: 10

Trp Ser His Pro Gln Phe Glu Lys Gly Gly Gly Ser Gly Gly Gly Ser
```

```
                1               5                    10                  15
            Gly Gly Gly Ser Trp Ser His Pro Gln Phe Glu Lys
                            20                  25
```

<210> SEQ ID NO 11
<211> LENGTH: 747
<212> TYPE: PRT
<213> ORGANISM: Artificial Sequence
<220> FEATURE:
<223> OTHER INFORMATION: a modified gB sequence

<400> SEQUENCE: 11

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Gly His Arg Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Ala
225                 230                 235                 240

Phe His Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
```

```
                340                 345                 350
Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Ser Thr Lys Ser Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Pro Pro Arg Met Lys Gln
    690                 695                 700

Leu Glu Asp Lys Val Glu Glu Leu Leu Ser Lys Asn Tyr His Leu Glu
705                 710                 715                 720

Asn Glu Val Ala Arg Leu Lys Lys Leu Val Gly Glu Arg Glu Asn Leu
                725                 730                 735

Tyr Phe Gln Gly Gly His His His His His His
            740                 745

<210> SEQ ID NO 12
```

<211> LENGTH: 857
<212> TYPE: PRT
<213> ORGANISM: Artificial Sequence
<220> FEATURE:
<223> OTHER INFORMATION: a modified gB sequence

<400> SEQUENCE: 12

```
Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Ala
            20                  25                  30

Thr Thr Val Gln Pro Th

```
Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Ala Pro Ser
            405                 410                 415

Ala Ala Arg Gly Ser Thr Pro Ala Ala Val Leu Arg Arg Arg Arg
            420                 425                 430

Asp Ala Gly Asn Ala Thr Thr Pro Val Pro Pro Thr Ala Pro Gly Lys
            435                 440                 445

Ser Leu Gly Thr Leu Asn Asn Pro Ala Thr Val Gln Ile Gln Phe Ala
450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
                500                 505                 510

Ala Val Ala Ala Lys Arg Leu Gly Asp Val Ile Ser Val Ser Gln Cys
            515                 520                 525

Val Pro Val Asn Gln Ala Thr Val Thr Leu Arg Lys Ser Met Arg Val
530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
            580                 585                 590

Gln Tyr Tyr Phe Gln Ser Gly Asn Glu Ile His Val Tyr Asn Asp Tyr
            595                 600                 605

His His Phe Lys Thr Ile Glu Leu Asp Gly Ile Ala Thr Leu Gln Thr
        610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
            660                 665                 670

Gly Leu Arg Lys Asp Leu Asp Asn Ala Val Ser Asn Gly Arg Asn Gln
        675                 680                 685

Phe Val Asp Gly Leu Gly Glu Leu Met Asp Ser Leu Gly Ser Val Gly
            690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735

Leu Ile Leu Val Leu Val Ala Gly Val Val Ile Leu Val Ile Ser Leu
            740                 745                 750

Thr Arg Arg Thr Arg Gln Met Ser Gln Gln Pro Val Gln Met Leu Tyr
            755                 760                 765

Pro Gly Ile Asp Glu Leu Ala Gln Gln His Ala Ser Gly Glu Gly Pro
        770                 775                 780

Gly Ile Asn Pro Ile Ser Lys Thr Glu Leu Gln Ala Ile Met Leu Ala
785                 790                 795                 800
```

-continued

```
Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
            820                 825                 830

Pro Gly Leu Arg Arg Arg Tyr His Asp Pro Glu Thr Ala Ala Ala
        835                 840                 845

Leu Leu Gly Glu Ala Glu Thr Glu Phe
850                 855

<210> SEQ ID NO 13
<211> LENGTH: 754
<212> TYPE: PRT
<213> ORGANISM: Artificial Sequence
<220> FEATURE:
<223> OTHER INFORMATION: a modified gB sequence

<400> SEQUENCE: 13

Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Pro Ala
                20                  25                  30

Thr Thr Val Gln Pro Thr Ala Thr Arg Gln Gln Thr Ser Phe Pro Phe
            35                  40                  45

Arg Val Cys Glu Leu Ser Ser His Gly Asp Leu Phe Arg Phe Ser Ser
50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly His
                100                 105                 110

Arg Ala Asp Ser Val Thr Asn Arg His Glu Glu Lys Phe Ser Val Asp
            115                 120                 125

Ser Tyr Glu Thr Asp Gln Met Asp Thr Ile Tyr Gln Cys Tyr Asn Ala
130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
            180                 185                 190

Arg Val Glu Ala Thr Tyr Arg Thr Arg Thr Thr Val Asn Cys Leu Ile
        195                 200                 205

Thr Asp Met Met Ala Lys Ser Asn Ser Pro Phe Asp Phe Val Thr
210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
290                 295                 300
```

```
Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Ala Trp Leu Pro
370                 375                 380

Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Ala Pro Ser
            405                 410                 415

Ala Ala Arg Gly Ser Thr Pro Ala Ala Val Leu Ser Ser Arg Ser Arg
                420                 425                 430

Asp Ala Gly Asn Ala Thr Thr Pro Val Pro Pro Thr Ala Pro Gly Lys
                435                 440                 445

Ser Leu Gly Thr Leu Asn Asn Pro Ala Thr Val Gln Ile Gln Phe Ala
450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
                500                 505                 510

Ala Val Ala Ala Lys Arg Leu Gly Asp Val Ile Ser Val Ser Gln Cys
                515                 520                 525

Val Pro Val Asn Gln Ala Thr Val Thr Leu Arg Lys Ser Met Arg Val
            530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
            580                 585                 590

Gln Tyr Tyr Phe Gln Ser Gly Asn Glu Ile His Val Tyr Asn Asp Tyr
        595                 600                 605

His His Phe Lys Thr Ile Glu Leu Asp Gly Ile Ala Thr Leu Gln Thr
610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
                660                 665                 670

Gly Leu Arg Lys Asp Leu Asp Asn Ala Val Ser Asn Gly Arg Asn Gln
                675                 680                 685

Phe Val Asp Gly Leu Gly Glu Leu Met Asp Ser Leu Gly Ser Val Gly
                690                 695                 700

Gln Pro Pro Arg Met Lys Gln Leu Glu Asp Lys Val Glu Glu Leu Leu
705                 710                 715                 720

Ser Lys Asn Tyr His Leu Glu Asn Glu Val Ala Arg Leu Lys Lys Leu
```

```
                        725                 730                 735
Val Gly Glu Arg Glu Asn Leu Tyr Phe Gln Gly Gly His His His His
                740                 745                 750

His His

<210> SEQ ID NO 14
<211> LENGTH: 772
<212> TYPE: PRT
<213> ORGANISM: Artificial Sequence
<220> FEATURE:
<223> OTHER INFORMATION: a modified gB sequence

<400> SEQUENCE: 14

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
                20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Ser Glu Ala Val Ser
        50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Gly His Arg Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Ala
225                 230                 235                 240

Phe His Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335
```

```
Gln Asp Glu Lys Asn Val Thr Cys Gln Leu Thr Phe Trp Glu Ala Ser
                340                 345                 350

Glu Arg Thr Ile Arg Ser Glu Ala Asp Ser Tyr His Phe Ser Ser
            355                 360                 365

Ala Lys Met Thr Ala Thr Phe Leu Ser Lys Lys Gln Glu Val Asn Met
        370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Thr Thr Gln Thr Ser Thr Ser Asp Asn
    450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Arg Phe Met Gly Asp Val
    530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
    690                 695                 700

Pro Pro Tyr Leu Lys Gly Leu Asp Asp Leu Met Ser Gly Leu Gly Ala
705                 710                 715                 720

Ala Gly Lys Pro Pro Arg Met Lys Gln Leu Glu Asp Lys Val Glu Glu
                725                 730                 735

Leu Leu Ser Lys Asn Tyr His Leu Glu Asn Glu Val Ala Arg Leu Lys
            740                 745                 750
```

Lys Leu Val Gly Glu Arg Glu Asn Leu Tyr Phe Gln Gly Gly His His
            755                 760                 765

His His His His
    770

<210> SEQ ID NO 15
<211> LENGTH: 737
<212> TYPE: PRT
<213> ORGANISM: Artificial Sequence
<220> FEATURE:
<223> OTHER INFORMATION: a modified gB sequence

<400> SEQUENCE: 15

Val Ser Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
                20                  25                  30

Gln Arg Val Thr Ser Ser Gln Thr Val Ser His Gly Val Asn Glu Thr
            35                  40                  45

Ile Tyr Asn Thr Thr Leu Lys Tyr Gly Asp Val Val Gly Val Asn Thr
    50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Ser Met Lys Pro Ile Asn
                85                  90                  95

Glu Asp Leu Asp Glu Gly Ile Met Val Val Tyr Lys Arg Asn Ile Val
            100                 105                 110

Ala His Thr Phe Lys Val Arg Val Tyr Gln Lys Val Leu Thr Phe Arg
        115                 120                 125

Arg Ser Tyr Ala Gly His Arg Thr Thr Tyr Leu Leu Gly Ser Asn Thr
    130                 135                 140

Glu Tyr Val Ala Pro Pro Met Trp Glu Ile His His Ile Asn Ser His
145                 150                 155                 160

Ser Gln Cys Tyr Ser Ser Tyr Ser Arg Val Ile Ala Gly Thr Val Phe
                165                 170                 175

Val Ala Tyr His Arg Asp Ser Tyr Glu Asn Lys Thr Met Gln Leu Met
            180                 185                 190

Pro Asp Asp Tyr Ser Asn Thr His Ser Thr Arg Tyr Val Thr Val Lys
        195                 200                 205

Asp Gln Trp His Ser Arg Gly Ser Thr Ala Phe His Arg Glu Thr Cys
    210                 215                 220

Asn Leu Asn Cys Met Val Thr Ile Thr Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Ala Ser Tyr Phe Gly Glu Asn Ala
            260                 265                 270

Asp Lys Phe Phe Ile Phe Pro Asn Tyr Thr Ile Val Ser Asp Phe Gly
        275                 280                 285

Arg Pro Asn Ser Ala Leu Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
                340                 345                 350

Phe Leu Ser Lys Lys Gln Glu Val Asn Met Ser Asp Ser Ala Leu Asp
        355                 360                 365

Cys Val Arg Asp Glu Ala Ile Asn Lys Leu Gln Gln Ile Phe Asn Thr
    370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Leu Thr
        420                 425                 430

His Asn Ser Thr Lys Ser Ser Thr Asp Gly Asn Asn Ala Thr His Leu
    435                 440                 445

Ser Asn Met Glu Ser Val His Asn Leu Val Tyr Ala Gln Leu Gln Phe
450                 455                 460

Thr Tyr Asp Thr Leu Arg Gly Tyr Ile Asn Pro Ala Leu Ala Gln Ile
465                 470                 475                 480

Ala Glu Ala Trp Cys Val Asp Gln Arg Arg Thr Leu Glu Val Phe Lys
                485                 490                 495

Glu Leu Ser Lys Ile Asn Pro Ser Ala Ile Leu Ser Ala Ile Tyr Asn
        500                 505                 510

Lys Pro Ile Ala Ala Arg Phe Met Gly Asp Val Leu Gly Leu Ala Ser
    515                 520                 525

Cys Val Thr Ile Asn Gln Thr Ser Val Lys Val Leu Arg Asp Met Asn
530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
        580                 585                 590

Ser Leu Lys Ile Phe Ile Ala Gly Asn Ser Ala Tyr Glu Tyr Val Asp
    595                 600                 605

Tyr Leu Phe Lys Arg Met Ile Asp Leu Ser Ser Ile Ser Thr Val Asp
610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
        660                 665                 670

Lys Tyr Val Glu Asp Lys Val Val Asp Pro Leu Pro Pro Tyr Leu Lys
    675                 680                 685

Gly Leu Asp Asp Leu Met Ser Gly Leu Gly Ala Ala Gly Lys Pro Pro
690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg

<210> SEQ ID NO 16

-continued

```
<211> LENGTH: 737
<212> TYPE: PRT
<213> ORGANISM: Artificial Sequence
<220> FEATURE:
<223> OTHER INFORMATION: a modified gB sequence

<400> SEQUENCE: 16

Val Ser Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
            20                  25                  30

Gln Arg Val Thr Ser Ser Gln

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
            405                 410                 415

Leu Val Glu Leu Glu Arg Leu Ala Asn Arg Ser Ser Leu Asn Leu Thr
        420                 425                 430

His Asn Ser Thr Lys Ser Ser Thr Asp Gly Asn Asn Ala Thr His Leu
            435                 440                 445

Ser Asn Met Glu Ser Val His Asn Leu Val Tyr Ala Gln Leu Gln Phe
        450                 455                 460

Thr Tyr Asp Thr Leu Arg Gly Tyr Ile Asn Arg Ala Leu Ala Gln Ile
465                 470                 475                 480

Ala Glu Ala Pro Cys Val Asp Gln Arg Arg Thr Leu Glu Val Phe Lys
            485                 490                 495

Glu Leu Ser Lys Ile Asn Pro Ser Ala Ile Leu Ser Ala Ile Tyr Asn
        500                 505                 510

Lys Pro Ile Ala Ala Arg Phe Met Gly Asp Val Leu Gly Leu Ala Ser
            515                 520                 525

Cys Val Thr Ile Asn Gln Thr Ser Val Lys Val Leu Arg Asp Met Asn
530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
            565                 570                 575

Asn Glu Ile Leu Leu Gly Asn His Arg Thr Glu Glu Cys Gln Leu Pro
        580                 585                 590

Ser Leu Lys Ile Phe Ile Ala Gly Asn Ser Ala Tyr Glu Tyr Val Asp
            595                 600                 605

Tyr Leu Phe Lys Arg Met Ile Asp Leu Ser Ser Ile Ser Thr Val Asp
610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
            645                 650                 655

Asp Leu Glu Glu Ile Met Arg Glu Phe Asn Ser Tyr Lys Gln Arg Val
        660                 665                 670

Lys Tyr Val Glu Asp Lys Val Val Asp Pro Leu Pro Pro Tyr Leu Lys
            675                 680                 685

Gly Leu Asp Asp Leu Met Ser Gly Leu Gly Ala Ala Gly Lys Pro Pro
        690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
            725                 730                 735

Arg

<210> SEQ ID NO 17
<211> LENGTH: 737
<212> TYPE: PRT
<213> ORGANISM: Artificial Sequence
<220> FEATURE:
<223> OTHER INFORMATION: a modified gB sequence

<400> SEQUENCE: 17

-continued

```
Val Ser Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
            20                  25                  30

Gln Arg Val Thr Ser Ser Gln Thr Val Ser His Gly Val Asn Glu Thr
            35                  40                  45

Ile Tyr Asn Thr Thr Leu Lys Tyr Gly Asp Val Val Gly Val Asn Thr
50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Ser Met Lys Pro Ile Asn
                85                  90                  95

Glu Asp Leu Asp Glu Gly Ile Met Val Val Tyr Lys Arg Asn Ile Val
                100                 105                 110

Ala His Thr Phe Lys Val Arg Val Tyr Gln Lys Val Leu Thr Phe Arg
            115                 120                 125

Arg Ser Tyr Ala Gly His Arg Thr Thr Tyr Leu Leu Gly Ser Asn Thr
            130                 135                 140

Glu Tyr Val Ala Pro Pro Met Trp Glu Ile His Ile Asn Ser His
145                 150                 155                 160

Ser Gln Cys Tyr Ser Ser Tyr Ser Arg Val Ile Ala Gly Thr Val Phe
                165                 170                 175

Val Ala Tyr His Arg Asp Ser Tyr Glu Asn Lys Thr Met Gln Leu Met
                180                 185                 190

Pro Asp Asp Tyr Ser Asn Thr His Ser Thr Arg Tyr Val Thr Val Lys
                195                 200                 205

Asp Gln Trp His Ser Arg Gly Ser Thr Ala Phe His Arg Glu Thr Cys
210                 215                 220

Asn Leu Asn Cys Met Val Thr Ile Thr Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Ala Ser Tyr Phe Gly Glu Asn Ala
                260                 265                 270

Asp Lys Phe Phe Ile Phe Pro Asn Tyr Thr Ile Val Ser Asp Phe Gly
            275                 280                 285

Arg Pro Asn Ser Ala Leu Glu Thr His Arg Leu Val Ala Phe Leu Glu
            290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
            340                 345                 350

Phe Leu Ser Lys Lys Gln Glu Val Asn Met Ser Asp Ser Ala Leu Asp
            355                 360                 365

Cys Val Arg Asp Glu Ala Ile Asn Lys Leu Gln Gln Ile Phe Asn Thr
            370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Leu Thr
```

```
                420             425             430
His Asn Ser Thr Lys Ser Ser Thr Asp Gly Asn Asn Ala Thr His Leu
            435                 440                 445

Ser Asn Met Glu Ser Val His Asn Leu Val Tyr Ala Gln Leu Gln Phe
        450                 455                 460

Thr Tyr Asp Thr Leu Arg Gly Tyr Ile Asn Arg Ala Leu Ala Gln Ile
465                 470                 475                 480

Ala Glu Ala Trp Pro Val Asp Gln Arg Arg Thr Leu Glu Val Phe Lys
                485                 490                 495

Glu Leu Ser Lys Ile Asn Pro Ser Ala Ile Leu Ser Ala Ile Tyr Asn
            500                 505                 510

Lys Pro Ile Ala Ala Arg Phe Met Gly Asp Val Leu Gly Leu Ala Ser
        515                 520                 525

Cys Val Thr Ile Asn Gln Thr Ser Val Lys Val Leu Arg Asp Met Asn
    530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
            580                 585                 590

Ser Leu Lys Ile Phe Ile Ala Gly Asn Ser Ala Tyr Glu Tyr Val Asp
        595                 600                 605

Tyr Leu Phe Lys Arg Met Ile Asp Leu Ser Ser Ile Ser Thr Val Asp
    610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
            660                 665                 670

Lys Tyr Val Glu Asp Lys Val Val Asp Pro Leu Pro Pro Tyr Leu Lys
        675                 680                 685

Gly Leu Asp Asp Leu Met Ser Gly Leu Gly Ala Ala Gly Lys Pro Pro
    690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg

<210> SEQ ID NO 18
<211> LENGTH: 737
<212> TYPE: PRT
<213> ORGANISM: Artificial Sequence
<220> FEATURE:
<223> OTHER INFORMATION: a modified gB sequence

<400> SEQUENCE: 18

Val Ser Ser Ser Thr Arg Gly Thr Ser Ala Thr His Ser His His
1

```
Ile Tyr Asn Thr Thr Leu Lys Tyr Gly Asp Val Val Gly Val Asn Thr
    50                  55                  60
Thr Lys Tyr Pro Tyr Arg Val Cys Ser Met Ala Gln Gly Thr Asp Leu
 65                  70                  75                  80
Ile Arg Phe Glu Arg Asn Ile Val Cys Thr Ser Met Lys Pro Ile Asn
                 85                  90                  95
Glu Asp Leu Asp Glu Gly Ile Met Val Val Tyr Lys Arg Asn Ile Val
            100                 105                 110
Ala His Thr Phe Lys Val Arg Val Tyr Gln Lys Val Leu Thr Phe Arg
        115                 120                 125
Arg Ser Tyr Ala Gly His Arg Thr Thr Tyr Leu Leu Gly Ser Asn Thr
    130                 135                 140
Glu Tyr Val Ala Pro Pro Met Trp Glu Ile His Ile Asn Ser His
145                 150                 155                 160
Ser Gln Cys Tyr Ser Ser Tyr Ser Arg Val Ile Ala Gly Thr Val Phe
                165                 170                 175
Val Ala Tyr His Arg Asp Ser Tyr Glu Asn Lys Thr Met Gln Leu Met
            180                 185                 190
Pro Asp Asp Tyr Ser Asn Thr His Ser Thr Arg Tyr Val Thr Val Lys
        195                 200                 205
Asp Gln Trp His Ser Arg Gly Ser Thr Ala Phe His Arg Glu Thr Cys
    210                 215                 220
Asn Leu Asn Cys Met Val Thr Ile Thr Thr Ala Arg Ser Lys Tyr Pro
225                 230                 235                 240
Tyr His Phe Phe Ala Thr Ser Thr Gly Asp Val Val Asp Ile Ser Pro
                245                 250                 255
Phe Tyr Asn Gly Thr Asn Arg Asn Ala Ser Tyr Phe Gly Glu Asn Ala
            260                 265                 270
Asp Lys Phe Phe Ile Phe Pro Asn Tyr Thr Ile Val Ser Asp Phe Gly
        275                 280                 285
Arg Pro Asn Ser Ala Leu Glu Thr His Arg Leu Val Ala Phe Leu Glu
    290                 295                 300
Arg Ala Asp Ser Val Ile Ser Trp Asp Ile Gln Asp Glu Lys Asn Val
305                 310                 315                 320
Thr Cys Gln Leu Thr Phe Trp Glu Ala Ser Glu Arg Thr Ile Arg Ser
                325                 330                 335
Glu Ala Glu Asp Ser Tyr His Phe Ser Ser Ala Lys Met Thr Ala Thr
            340                 345                 350
Phe Leu Ser Lys Lys Gln Glu Val Asn Met Ser Asp Ser Ala Leu Asp
        355                 360                 365
Cys Val Arg Asp Glu Ala Ile Asn Lys Leu Gln Gln Ile Phe Asn Thr
    370                 375                 380
Ser Tyr Asn Gln Thr Tyr Glu Lys Tyr Gly Asn Val Ser Val Phe Glu
385                 390                 395                 400
Thr Thr Gly Gly Leu Val Val Phe Trp Gln Gly Ile Lys Gln Lys Ser
                405                 410                 415
Leu Val Glu Leu Glu Arg Leu Ala Asn Arg Ser Ser Leu Asn Leu Thr
            420                 425                 430
His Asn Ser Thr Lys Ser Ser Thr Asp Gly Asn Asn Ala Thr His Leu
        435                 440                 445
Ser Asn Met Glu Ser Val His Asn Leu Val Tyr Ala Gln Leu Gln Phe
    450                 455                 460
```

```
Thr Tyr Asp Thr Leu Arg Gly Tyr Ile Asn Arg Ala Leu Ala Gln Ile
465                 470                 475                 480

Ala Glu Ala Trp Cys Val Pro Gln Arg Arg Thr Leu Glu Val Phe Lys
                485                 490                 495

Glu Leu Ser Lys Ile Asn Pro Ser Ala Ile Leu Ser Ala Ile Tyr Asn
            500                 505                 510

Lys Pro Ile Ala Ala Arg Phe Met Gly Asp Val Leu Gly Leu Ala Ser
        515                 520                 525

Cys Val Thr Ile Asn Gln Thr Ser Val Lys Val Leu Arg Asp Met Asn
    530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
            580                 585                 590

Ser Leu Lys Ile Phe Ile Ala Gly Asn Ser Ala Tyr Glu Tyr Val Asp
        595                 600                 605

Tyr Leu Phe Lys Arg Met Ile Asp Leu Ser Ser Ile Ser Thr Val Asp
    610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
            660                 665                 670

Lys Tyr Val Glu Asp Lys Val Val Asp Pro Leu Pro Pro Tyr Leu Lys
        675                 680                 685

Gly Leu Asp Asp Leu Met Ser Gly Leu Gly Ala Ala Gly Lys Pro Pro
    690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg

<210> SEQ ID NO 19
<211> LENGTH: 737
<212> TYPE: PRT
<213> ORGANISM: Artificial Sequence
<220> FEATURE:
<223> OTHER INFORMATION: a modified gB sequence

<400> SEQUENCE: 19

Val Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
            20                  25                  30

Gln Arg Val Thr Ser Ser Gln Thr Val Ser His Gly Val As

```
                    85                  90                  95
Glu Asp Leu Asp Glu Gly Ile Met Val Val Tyr Lys Arg Asn Ile Val
                100                 105                 110
Ala His Thr Phe Lys Val Arg Val Tyr Gln Lys Val Leu Thr Phe Arg
                115                 120                 125
Arg Ser Tyr Ala Gly His Arg Thr Thr Tyr Leu Leu Gly Ser Asn Thr
                130                 135                 140
Glu Tyr Val Ala Pro Pro Met Trp Glu Ile His His Ile Asn Ser His
145                 150                 155                 160
Ser Gln Cys Tyr Ser Ser Tyr Ser Arg Val Ile Ala Gly Thr Val Phe
                165                 170                 175
Val Ala Tyr His Arg Asp Ser Tyr Glu Asn Lys Thr Met Gln Leu Met
                180                 185                 190
Pro Asp Asp Tyr Ser Asn Thr His Ser Thr Arg Tyr Val Thr Val Lys
                195                 200                 205
Asp Gln Trp His Ser Arg Gly Ser Thr Ala Phe His Arg Glu Thr Cys
                210                 215                 220
Asn Leu Asn Cys Met Val Thr Ile Thr Thr Ala Arg Ser Lys Tyr Pro
225                 230                 235                 240
Tyr His Phe Phe Ala Thr Ser Thr Gly Asp Val Val Asp Ile Ser Pro
                245                 250                 255
Phe Tyr Asn Gly Thr Asn Arg Asn Ala Ser Tyr Phe Gly Glu Asn Ala
                260                 265                 270
Asp Lys Phe Phe Ile Phe Pro Asn Tyr Thr Ile Val Ser Asp Phe Gly
                275                 280                 285
Arg Pro Asn Ser Ala Leu Glu Thr His Arg Leu Val Ala Phe Leu Glu
                290                 295                 300
Arg Ala Asp Ser Val Ile Ser Trp Asp Ile Gln Asp Glu Lys Asn Val
305                 310                 315                 320
Thr Cys Gln Leu Thr Phe Trp Glu Ala Ser Glu Arg Thr Ile Arg Ser
                325                 330                 335
Glu Ala Glu Asp Ser Tyr His Phe Ser Ser Ala Lys Met Thr Ala Thr
                340                 345                 350
Phe Leu Ser Lys Lys Gln Glu Val Asn Met Ser Asp Ser Ala Leu Asp
                355                 360                 365
Cys Val Arg Asp Glu Ala Ile Asn Lys Leu Gln Ile Phe Asn Thr
370                 375                 380
Ser Tyr Asn Gln Thr Tyr Glu Lys Tyr Gly Asn Val Ser Val Phe Glu
385                 390                 395                 400
Thr Thr Gly Gly Leu Val Val Phe Trp Gln Gly Ile Lys Gln Lys Ser
                405                 410                 415
Leu Val Glu Leu Glu Arg Leu Ala Asn Arg Ser Ser Leu Asn Leu Thr
                420                 425                 430
His Asn Ser Thr Lys Ser Ser Thr Asp Gly Asn Asn Ala Thr His Leu
                435                 440                 445
Ser Asn Met Glu Ser Val His Asn Leu Val Tyr Ala Gln Leu Gln Phe
450                 455                 460
Thr Tyr Asp Thr Leu Arg Gly Tyr Ile Asn Arg Ala Leu Ala Gln Ile
465                 470                 475                 480
Ala Glu Ala Trp Cys Val Asp Pro Arg Arg Thr Leu Glu Val Phe Lys
                485                 490                 495
Glu Leu Ser Lys Ile Asn Pro Ser Ala Ile Leu Ser Ala Ile Tyr Asn
                500                 505                 510
```

```
Lys Pro Ile Ala Ala Arg Phe Met Gly Asp Val Leu Gly Leu Ala Ser
            515                 520                 525

Cys Val Thr Ile Asn Gln Thr Ser Val Lys Val Leu Arg Asp Met Asn
    530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
            580                 585                 590

Ser Leu Lys Ile Phe Ile Ala Gly Asn Ser Ala Tyr Glu Tyr Val Asp
        595                 600                 605

Tyr Leu Phe Lys Arg Met Ile Asp Leu Ser Ser Ile Ser Thr Val Asp
610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
            660                 665                 670

Lys Tyr Val Glu Asp Lys Val Val Asp Pro Leu Pro Pro Tyr Leu Lys
        675                 680                 685

Gly Leu Asp Asp Leu Met Ser Gly Leu Gly Ala Ala Gly Lys Pro Pro
    690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg
```

<210> SEQ ID NO 20
<211> LENGTH: 737
<212> TYPE: PRT
<213> ORGANISM: Artificial Sequence
<220> FEATURE:
<223> OTHER INFORMATION: a modified gB sequence

<400> SEQUENCE: 20

```
Val Ser Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
                20                  25                  30

Gln Arg Val Thr Ser Ser Gln Thr Val Ser His Gly Val Asn Glu Thr
            35                  40                  45

Ile Tyr Asn Thr Thr Leu Lys Tyr Gly Asp Val Val Gly Val Asn Thr
        50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Ser Met Lys Pro Ile Asn
                85                  90                  95

Glu Asp Leu Asp Glu Gly Ile Met Val Val Tyr Lys Arg Asn Ile Val
            100                 105                 110

Ala His Thr Phe Lys Val Arg Val Tyr Gln Lys Val Leu Thr Phe Arg
        115                 120                 125
```

```
Arg Ser Tyr Ala Gly His Arg Thr Thr Tyr Leu Leu Gly Ser Asn Thr
    130                 135                 140

Glu Tyr Val Ala Pro Pro Met Trp Glu Ile His His Ile Asn Ser His
145                 150                 155                 160

Ser Gln Cys Tyr Ser Ser Tyr Ser Arg Val Ile Ala Gly Thr Val Phe
                165                 170                 175

Val Ala Tyr His Arg Asp Ser Tyr Glu Asn Lys Thr Met Gln Leu Met
            180                 185                 190

Pro Asp Asp Tyr Ser Asn Thr His Ser Thr Arg Tyr Val Thr Val Lys
        195                 200                 205

Asp Gln Trp His Ser Arg Gly Ser Thr Ala Phe His Arg Glu Thr Cys
    210                 215                 220

Asn Leu Asn Cys Met Val Thr Ile Thr Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Ala Ser Tyr Phe Gly Glu Asn Ala
            260                 265                 270

Asp Lys Phe Phe Ile Phe Pro Asn Tyr Thr Ile Val Ser Asp Phe Gly
        275                 280                 285

Arg Pro Asn Ser Ala Leu Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
            340                 345                 350

Phe Leu Ser Lys Lys Gln Glu Val Asn Met Ser Asp Ser Ala Leu Asp
        355                 360                 365

Cys Val Arg Asp Glu Ala Ile Asn Lys Leu Gln Gln Ile Phe Asn Thr
370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Leu Thr
            420                 425                 430

His Asn Ser Thr Lys Ser Ser Thr Asp Gly Asn Asn Ala Thr His Leu
        435                 440                 445

Ser Asn Met Glu Ser Val His Asn Leu Val Tyr Ala Gln Leu Gln Phe
450                 455                 460

Thr Tyr Asp Thr Leu Arg Gly Tyr Ile Asn Arg Ala Leu Ala Gln Ile
465                 470                 475                 480

Ala Glu Ala Trp Cys Val Asp Gln Pro Arg Thr Leu Glu Val Phe Lys
                485                 490                 495

Glu Leu Ser Lys Ile Asn Pro Ser Ala Ile Leu Ser Ala Ile Tyr Asn
            500                 505                 510

Lys Pro Ile Ala Ala Arg Phe Met Gly Asp Val Leu Gly Leu Ala Ser
        515                 520                 525

Cys Val Thr Ile Asn Gln Thr Ser Val Lys Val Leu Arg Asp Met Asn
530                 535                 540

Val Lys Glu Ser Pro Gly Arg Cys Tyr Ser Arg Pro Val Val Ile Phe
```

```
545                 550                 555                 560
Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
                580                 585                 590

Ser Leu Lys Ile Phe Ile Ala Gly Asn Ser Ala Tyr Glu Tyr Val Asp
                595                 600                 605

Tyr Leu Phe Lys Arg Met Ile Asp Leu Ser Ser Ile Ser Thr Val Asp
                610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
                660                 665                 670

Lys Tyr Val Glu Asp Lys Val Val Asp Pro Leu Pro Pro Tyr Leu Lys
                675                 680                 685

Gly Leu Asp Asp Leu Met Ser Gly Leu Gly Ala Ala Gly Lys Pro Pro
                690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg

<210> SEQ ID NO 21
<211> LENGTH: 737
<212> TYPE: PRT
<213> ORGANISM: Artificial Sequence
<220> FEATURE:
<223> OTHER INFORMATION: a modified gB sequence

<400> SEQUENCE: 21

Val Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
                20                  25                  30

Gln Arg Val Thr Ser Ser Gln Thr Val Ser His Gly Val Asn Glu Thr
                35                  40                  45

Ile Tyr Asn Thr Thr Leu Lys Tyr Gly Asp Val Val Gly Val Asn Thr
            50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Ser Met Lys Pro Ile Asn
                85                  90                  95

Glu Asp Leu Asp Glu Gly Ile Met Val Val Tyr Lys Arg Asn Ile Val
                100                 105                 110

Ala His Thr Phe Lys Val Arg Val Tyr Gln Lys Val Leu Thr Phe Arg
                115                 120                 125

Arg Ser Tyr Ala Gly His Arg Thr Thr Tyr Leu Leu Gly Ser Asn Thr
                130                 135                 140

Glu Tyr Val Ala Pro Pro Met Trp Glu Ile His His Ile Asn Ser His
145                 150                 155                 160

Ser Gln Cys Tyr Ser Ser Tyr Ser Arg Val Ile Ala Gly Thr Val Phe
                165                 170                 175
```

-continued

Val Ala Tyr His Arg Asp Ser Tyr Glu Asn Lys Thr Met Gln Leu Met
                180                 185                 190

Pro Asp Asp Tyr Ser Asn Thr His Ser Thr Arg Tyr Val Thr Val Lys
            195                 200                 205

Asp Gln Trp His Ser Arg Gly Ser Thr Ala Phe His Arg Glu Thr Cys
        210                 215                 220

Asn Leu Asn Cys Met Val Thr Ile Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Ala Ser Tyr Phe Gly Glu Asn Ala
            260                 265                 270

Asp Lys Phe Phe Ile Phe Pro Asn Tyr Thr Ile Val Ser Asp Phe Gly
        275                 280                 285

Arg Pro Asn Ser Ala Leu Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
            340                 345                 350

Phe Leu Ser Lys Lys Gln Glu Val Asn Met Ser Asp Ser Ala Leu Asp
        355                 360                 365

Cys Val Arg Asp Glu Ala Ile Asn Lys Leu Gln Gln Ile Phe Asn Thr
    370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Leu Thr
            420                 425                 430

His Asn Ser Thr Lys Ser Ser Thr Asp Gly Asn Asn Ala Thr His Leu
        435                 440                 445

Ser Asn Met Glu Ser Val His Asn Leu Val Tyr Ala Gln Leu Gln Phe
    450                 455                 460

Thr Tyr Asp Thr Leu Arg Gly Tyr Ile Asn Arg Ala Leu Ala Gln Ile
465                 470                 475                 480

Ala Glu Ala Pro Cys Val Asp Pro Arg Arg Thr Leu Glu Val Phe Lys
                485                 490                 495

Glu Leu Ser Lys Ile Asn Pro Ser Ala Ile Leu Ser Ala Ile Tyr Asn
            500                 505                 510

Lys Pro Ile Ala Ala Arg Phe Met Gly Asp Val Leu Gly Leu Ala Ser
        515                 520                 525

Cys Val Thr Ile Asn Gln Thr Ser Val Lys Val Leu Arg Asp Met Asn
    530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
            580                 585                 590

```
Ser Leu Lys Ile Phe Ile Ala Gly Asn Ser Ala Tyr Glu Tyr Val Asp
            595                 600                 605

Tyr Leu Phe Lys Arg Met Ile Asp Leu Ser Ser Ile Ser Thr Val Asp
        610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
            660                 665                 670

Lys Tyr Val Glu Asp Lys Val Val Asp Pro Leu Pro Pro Tyr Leu Lys
        675                 680                 685

Gly Leu Asp Asp Leu Met Ser Gly Leu Gly Ala Ala Gly Lys Pro Pro
690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg

<210> SEQ ID NO 22
<211> LENGTH: 1474
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: a modified gB sequence

<400> SEQUENCE: 22

Val Ser Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
            20                  25                  30

Gln Arg Val Thr Ser Ser Gln Thr Val Ser His Gly Val Asn Glu Thr
        35                  40                  45

Ile Tyr Asn Thr Thr Leu Lys Tyr Gly Asp Val Val Gly Val Asn Thr
    50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Ser Met Lys Pro Ile Asn
                85                  90                  95

Glu Asp Leu Asp Glu Gly Ile Met Val Val Tyr Lys Arg Asn Ile Val
            100                 105                 110

Ala His Thr Phe Lys Val Arg Val Tyr Gln Lys Val Leu Thr Phe Arg
        115                 120                 125

Arg Ser Tyr Ala Gly His Arg Thr Thr Tyr Leu Leu Gly Ser Asn Thr
    130                 135                 140

Glu Tyr Val Ala Pro Pro Met Trp Glu Ile His His Ile Asn Ser His
145                 150                 155                 160

Ser Gln Cys Tyr Ser Ser Tyr Ser Arg Val Ile Ala Gly Thr Val Phe
                165                 170                 175

Val Ala Tyr His Arg Asp Ser Tyr Glu Asn Lys Thr Met Gln Leu Met
            180                 185                 190

Pro Asp Asp Tyr Ser Asn Thr His Ser Thr Arg Tyr Val Thr Val Lys
```

```
              195                 200                 205
Asp Gln Trp His Ser Arg Gly Ser Thr Ala Phe His Arg Glu Thr Cys
    210                 215                 220

Asn Leu Asn Cys Met Val Thr Ile Thr Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Ala Ser Tyr Phe Gly Glu Asn Ala
                260                 265                 270

Asp Lys Phe Phe Ile Phe Pro Asn Tyr Thr Ile Val Ser Asp Phe Gly
                275                 280                 285

Arg Pro Asn Ser Ala Leu Glu Thr His Arg Leu Val Ala Phe Leu Glu
                290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
                340                 345                 350

Phe Leu Ser Lys Lys Gln Glu Val Asn Met Ser Asp Ser Ala Leu Asp
                355                 360                 365

Cys Val Arg Asp Glu Ala Ile Asn Lys Leu Gln Ile Phe Asn Thr
370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Leu Thr
                420                 425                 430

His Asn Ser Thr Lys Ser Ser Thr Asp Gly Asn Asn Ala Thr His Leu
                435                 440                 445

Ser Asn Met Glu Ser Val His Asn Leu Val Tyr Ala Gln Leu Gln Phe
450                 455                 460

Thr Tyr Asp Thr Leu Arg Gly Tyr Ile Asn Arg Ala Leu Ala Gln Ile
465                 470                 475                 480

Ala Glu Ala Trp Cys Val Pro Pro Arg Arg Thr Leu Glu Val Phe Lys
                485                 490                 495

Glu Leu Ser Lys Ile Asn Pro Ser Ala Ile Leu Ser Ala Ile Tyr Asn
                500                 505                 510

Lys Pro Ile Ala Ala Arg Phe Met Gly Asp Val Leu Gly Leu Ala Ser
                515                 520                 525

Cys Val Thr Ile Asn Gln Thr Ser Val Lys Val Leu Arg Asp Met Asn
530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
                580                 585                 590

Ser Leu Lys Ile Phe Ile Ala Gly Asn Ser Ala Tyr Glu Tyr Val Asp
                595                 600                 605

Tyr Leu Phe Lys Arg Met Ile Asp Leu Ser Ser Ile Ser Thr Val Asp
                610                 615                 620
```

```
Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
            645                 650                 655

Asp Leu Glu Glu Ile Met Arg Glu Phe Asn Ser Tyr Lys Gln Arg Val
            660                 665                 670

Lys Tyr Val Glu Asp Lys Val Val Asp Pro Leu Pro Pro Tyr Leu Lys
            675                 680                 685

Gly Leu Asp Asp Leu Met Ser Gly Leu Gly Ala Ala Gly Lys Pro Pro
            690                 695                 700

Arg Met Lys Gln Leu Glu Asp Lys Val Glu Glu Leu Leu Ser Lys Asn
705                 710                 715                 720

Tyr His Leu Glu Asn Glu Val Ala Arg Leu Lys Lys Leu Val Gly Glu
                725                 730                 735

Arg Val Ser Ser Ser Thr Arg Gly Thr Ser Ala Thr His Ser His
            740                 745                 750

His Ser Ser His Thr Thr Ser Ala Ala His Ser Arg Ser Gly Ser Val
        755                 760                 765

Ser Gln Arg Val Thr Ser Ser Gln Thr Val Ser His Gly Val Asn Glu
770                 775                 780

Thr Ile Tyr Asn Thr Thr Leu Lys Tyr Gly Asp Val Val Gly Val Asn
785                 790                 795                 800

Thr Thr Lys Tyr Pro Tyr Arg Val Cys Ser Met Ala Gln Gly Thr Asp
                805                 810                 815

Leu Ile Arg Phe Glu Arg Asn Ile Val Cys Thr Ser Met Lys Pro Ile
                820                 825                 830

Asn Glu Asp Leu Asp Glu Gly Ile Met Val Val Tyr Lys Arg Asn Ile
            835                 840                 845

Val Ala His Thr Phe Lys Val Arg Val Tyr Gln Lys Val Leu Thr Phe
850                 855                 860

Arg Arg Ser Tyr Ala Gly His Arg Thr Thr Tyr Leu Leu Gly Ser Asn
865                 870                 875                 880

Thr Glu Tyr Val Ala Pro Pro Met Trp Glu Ile His His Ile Asn Ser
                885                 890                 895

His Ser Gln Cys Tyr Ser Ser Tyr Ser Arg Val Ile Ala Gly Thr Val
            900                 905                 910

Phe Val Ala Tyr His Arg Asp Ser Tyr Glu Asn Lys Thr Met Gln Leu
            915                 920                 925

Met Pro Asp Asp Tyr Ser Asn Thr His Ser Thr Arg Tyr Val Thr Val
            930                 935                 940

Lys Asp Gln Trp His Ser Arg Gly Ser Thr Ala Phe His Arg Glu Thr
945                 950                 955                 960

Cys Asn Leu Asn Cys Met Val Thr Ile Thr Ala Arg Ser Lys Tyr
                965                 970                 975

Pro Tyr His Phe Phe Ala Thr Ser Thr Gly Asp Val Val Asp Ile Ser
            980                 985                 990

Pro Phe Tyr Asn Gly Thr Asn Arg Asn Ala Ser Tyr Phe Gly Glu Asn
            995                 1000                1005

Ala Asp Lys Phe Phe Ile Phe Pro Asn Tyr Thr Ile Val Ser Asp
        1010                1015                1020

Phe Gly Arg Pro Asn Ser Ala Leu Glu Thr His Arg Leu Val Ala
        1025                1030                1035
```

```
Phe Leu Glu Arg Ala Asp Ser Val Ile Ser Trp Asp Ile Gln Asp
    1040                1045                1050

Glu Lys Asn Val Thr Cys Gln Leu Thr Phe Trp Glu Ala Ser Glu
    1055                1060                1065

Arg Thr Ile Arg Ser Glu Ala Glu Asp Ser Tyr His Phe Ser Ser
    1070                1075                1080

Ala Lys Met Thr Ala Thr Phe Leu Ser Lys Lys Gln Glu Val Asn
    1085                1090                1095

Met Ser Asp Ser Ala Leu Asp Cys Val Arg Asp Glu Ala Ile Asn
    1100                1105                1110

Lys Leu Gln Gln Ile Phe Asn Thr Ser Tyr Asn Gln Thr Tyr Glu
    1115                1120                1125

Lys Tyr Gly Asn Val Ser Val Phe Glu Thr Thr Gly Gly Leu Val
    1130                1135                1140

Val Phe Trp Gln Gly Ile Lys Gln Lys Ser Leu Val Glu Leu Glu
    1145                1150                1155

Arg Leu Ala Asn Arg Ser Ser Leu Asn Leu Thr His Asn Ser Thr
    1160                1165                1170

Lys Ser Ser Thr Asp Gly Asn Asn Ala Thr His Leu Ser Asn Met
    1175                1180                1185

Glu Ser Val His Asn Leu Val Tyr Ala Gln Leu Gln Phe Thr Tyr
    1190                1195                1200

Asp Thr Leu Arg Gly Tyr Ile Asn Arg Ala Leu Ala Gln Ile Ala
    1205                1210                1215

Glu Ala Trp Cys Val Pro Pro Arg Arg Thr Leu Glu Val Phe Lys
    1220                1225                1230

Glu Leu Ser Lys Ile Asn Pro Ser Ala Ile Leu Ser Ala Ile Tyr
    1235                1240                1245

Asn Lys Pro Ile Ala Ala Arg Phe Met Gly Asp Val Leu Gly Leu
    1250                1255                1260

Ala Ser Cys Val Thr Ile Asn Gln Thr Ser Val Lys Val Leu Arg
    1265                1270                1275

Asp Met Asn Val Lys Glu Ser Pro Gly Arg Cys Tyr Ser Arg Pro
    1280                1285                1290

Val Val Ile Phe Asn Phe Ala Asn Ser Ser Tyr Val Gln Tyr Gly
    1295                1300                1305

Gln Leu Gly Glu Asp Asn Glu Ile Leu Leu Gly Asn His Arg Thr
    1310                1315                1320

Glu Glu Cys Gln Leu Pro Ser Leu Lys Ile Phe Ile Ala Gly Asn
    1325                1330                1335

Ser Ala Tyr Glu Tyr Val Asp Tyr Leu Phe Lys Arg Met Ile Asp
    1340                1345                1350

Leu Ser Ser Ile Ser Thr Val Asp Ser Met Ile Ala Leu Asp Ile
    1355                1360                1365

Asp Pro Leu Glu Asn Thr Asp Phe Arg Val Leu Glu Leu Tyr Ser
    1370                1375                1380

Gln Lys Glu Leu Arg Ser Ser Asn Val Phe Asp Leu Glu Glu Ile
    1385                1390                1395

Met Arg Glu Phe Asn Ser Tyr Lys Gln Arg Val Lys Tyr Val Glu
    1400                1405                1410

Asp Lys Val Val Asp Pro Leu Pro Pro Tyr Leu Lys Gly Leu Asp
    1415                1420                1425

Asp Leu Met Ser Gly Leu Gly Ala Ala Gly Lys Pro Pro Arg Met
```

```
            1430               1435               1440
Lys Gln  Leu Glu Asp Lys Val  Glu Glu Leu Leu Ser  Lys Asn Tyr
         1445                 1450                 1455

His Leu  Glu Asn Glu Val Ala  Arg Leu Lys Lys Leu  Val Gly Glu
         1460                 1465                 1470

Arg

<210> SEQ ID NO 23
<211> LENGTH: 736
<212> TYPE: PRT
<213> ORGANISM: Artificial Sequence
<220> FEATURE:
<223> OTHER INFORMATION: a modified gB sequence

<400> SEQUENCE: 23

Val Ser Ser Ser Ser Thr Ser  His Ala Thr Ser Ser  Thr His Asn Gly
1                 5                 10                 15

Ser His Thr Ser Arg Thr Thr  Ser Ala Gln Thr Arg  Ser Val Tyr Ser
             20                  25                  30

Gln His Val Thr Ser Ser Glu  Ala Val Ser His Arg  Ala Asn Glu Thr
             35                  40                  45

Ile Tyr Asn Thr Thr Leu Lys  Tyr Gly Asp Val Val  Gly Val Asn Thr
 50                  55                  60

Thr Lys Tyr Pro Tyr Arg Val  Cys Ser Met Ala Gln  Gly Thr Asp Leu
65                  70                  75                  80

Ile Arg Phe Glu Arg Asn Ile  Ile Cys Thr Ser Met  Lys Pro Ile Asn
                 85                  90                  95

Glu Asp Leu Asp Glu Gly Ile  Met Val Val Tyr Lys  Arg Asn Ile Val
             100                 105                 110

Ala His Thr Phe Lys Val Arg  Val Tyr Gln Lys Val  Leu Thr Phe Arg
             115                 120                 125

Arg Ser Tyr Ala Gly His Arg  Thr Thr Tyr Leu Leu  Gly Ser Asn Thr
130                 135                 140

Glu Tyr Val Ala Pro Pro Met  Trp Glu Ile His His  Ile Asn Lys Phe
145                 150                 155                 160

Ala Gln Cys Tyr Ser Ser Tyr  Ser Arg Val Ile Gly  Gly Thr Val Phe
                 165                 170                 175

Val Ala Tyr His Arg Asp Ser  Tyr Glu Asn Lys Thr  Met Gln Leu Ile
             180                 185                 190

Pro Asp Asp Tyr Ser Asn Thr  His Ser Thr Arg Tyr  Val Thr Val Lys
             195                 200                 205

Asp Gln Trp His Ser Arg Gly  Ser Thr Ala Phe His  Arg Glu Thr Cys
210                 215                 220

Asn Leu Asn Cys Met Leu Thr  Ile Thr Thr Ala Arg  Ser Lys Tyr Pro
225                 230                 235                 240

Tyr His Phe Phe Ala Thr Ser  Thr Gly Asp Val Val  Tyr Ile Ser Pro
                 245                 250                 255

Phe Tyr Asn Gly Thr Asn Arg  Asn Ala Ser Tyr Phe  Gly Glu Asn Ala
             260                 265                 270

Asp Lys Phe Phe Ile Phe Pro  Asn Tyr Thr Ile Val  Ser Asp Phe Gly
             275                 280                 285

Arg Pro Asn Ala Ala Pro Glu  Thr His Arg Leu Val  Ala Phe Leu Glu
             290                 295                 300

Arg Ala Asp Ser Val Ile Ser  Trp Asp Ile Gln Asp  Glu Lys Asn Val
305                 310                 315                 320
```

-continued

```
Thr Cys Gln Leu Thr Phe Trp Glu Ala Ser Glu Arg Thr Ile Arg Ser
            325                 330                 335

Glu Ala Glu Asp Ser Tyr His Phe Ser Ser Ala Lys Met Thr Ala Thr
        340                 345                 350

Phe Leu Ser Lys Lys Gln Glu Val Asn Met Ser Asp Ser Ala Leu Asp
        355                 360                 365

Cys Val Arg Asp Glu Ala Ile Asn Lys Leu Gln Gln Ile Phe Asn Thr
        370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
            420                 425                 430

His Thr Thr Gln Thr Ser Thr Ser Asp Asn Asn Thr Thr His Leu Ser
        435                 440                 445

Ser Met Glu Ser Val His Asn Leu Val Tyr Ala Gln Leu Gln Phe Thr
    450                 455                 460

Tyr Asp Thr Leu Arg Gly Tyr Ile Asn Pro Ala Leu Ala Gln Ile Ala
465                 470                 475                 480

Glu Ala Trp Cys Val Asp Gln Arg Arg Thr Leu Glu Val Phe Lys Glu
                485                 490                 495

Leu Ser Lys Ile Asn Pro Ser Ala Ile Leu Ser Ala Ile Tyr Asn Lys
            500                 505                 510

Pro Ile Ala Ala Arg Phe Met Gly Asp Val Leu Gly Leu Ala Ser Cys
        515                 520                 525

Val Thr Ile Asn Gln Thr Ser Val Lys Val Leu Arg Asp Met Asn Val
    530                 535                 540

Lys Glu Ser Pro Gly Arg Cys Tyr Ser Arg Pro Val Val Ile Phe Asn
545                 550                 555                 560

Phe Ala Asn Ser Ser Tyr Val Gln Tyr Gly Gln Leu Gly Glu Asp Asn
                565                 570                 575

Glu Ile Leu Leu Gly Asn His Arg Thr Glu Glu Cys Gln Leu Pro Ser
            580                 585                 590

Leu Lys Ile Phe Ile Ala Gly Asn Ser Ala Tyr Glu Tyr Val Asp Tyr
        595                 600                 605

Leu Phe Lys Arg Met Ile Asp Leu Ser Ser Ile Ser Thr Val Asp Ser
    610                 615                 620

Met Ile Ala Leu Asp Ile Asp Pro Leu Glu Asn Thr Asp Phe Arg Val
625                 630                 635                 640

Leu Glu Leu Tyr Ser Gln Lys Glu Leu Arg Ser Ser Asn Val Phe Asp
                645                 650                 655

Leu Glu Glu Ile Met Arg Glu Phe Asn Ser Tyr Lys Gln Arg Val Lys
            660                 665                 670

Tyr Val Glu Asp Lys Val Val Asp Pro Leu Pro Pro Tyr Leu Lys Gly
        675                 680                 685

Leu Asp Asp Leu Met Ser Gly Leu Gly Ala Ala Gly Lys Pro Pro Arg
    690                 695                 700

Met Lys Gln Leu Glu Asp Lys Val Glu Glu Leu Leu Ser Lys Asn Tyr
705                 710                 715                 720

His Leu Glu Asn Glu Val Ala Arg Leu Lys Lys Leu Val Gly Glu Arg
                725                 730                 735
```

<210> SEQ ID NO 24
<211> LENGTH: 736
<212> TYPE: PRT
<213> ORGANISM: Artificial Sequence
<220> FEATURE:
<223> OTHER INFORMATION: a modified gB sequence

<400> SEQUENCE: 24

```
Val Ser Ser Ser Ser Thr Ser His Ala Thr Ser Ser Thr His Asn Gly
1               5                   10                  15

Ser His Thr Ser Arg Thr Thr Ser Ala Gln Thr Arg Ser Val Tyr Ser
            20                  25                  30

Gln His Val Th

```
Cys Val Arg Asp Glu Ala Ile Asn Lys Leu Gln Gln Ile Phe Asn Thr
    370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
        420                 425                 430

His Thr Thr Gln Thr Ser Thr Ser Asp Asn Asn Thr His Leu Ser
            435                 440                 445

Ser Met Glu Ser Val His Asn Leu Val Tyr Ala Gln Leu Gln Phe Thr
450                 455                 460

Tyr Asp Thr Leu Arg Gly Tyr Ile Asn Arg Ala Leu Ala Gln Ile Ala
465                 470                 475                 480

Glu Ala Pro Cys Val Asp Gln Arg Arg Thr Leu Glu Val Phe Lys Glu
                485                 490                 495

Leu Ser Lys Ile Asn Pro Ser Ala Ile Leu Ser Ala Ile Tyr Asn Lys
            500                 505                 510

Pro Ile Ala Ala Arg Phe Met Gly Asp Val Leu Gly Leu Ala Ser Cys
        515                 520                 525

Val Thr Ile Asn Gln Thr Ser Val Lys Val Leu Arg Asp Met Asn Val
530                 535                 540

Lys Glu Ser Pro Gly Arg Cys Tyr Ser Arg Pro Val Val Ile Phe Asn
545                 550                 555                 560

Phe Ala Asn Ser Ser Tyr Val Gln Tyr Gly Gln Leu Gly Glu Asp Asn
                565                 570                 575

Glu Ile Leu Leu Gly Asn His Arg Thr Glu Glu Cys Gln Leu Pro Ser
            580                 585                 590

Leu Lys Ile Phe Ile Ala Gly Asn Ser Ala Tyr Glu Tyr Val Asp Tyr
        595                 600                 605

Leu Phe Lys Arg Met Ile Asp Leu Ser Ser Ile Ser Thr Val Asp Ser
610                 615                 620

Met Ile Ala Leu Asp Ile Asp Pro Leu Glu Asn Thr Asp Phe Arg Val
625                 630                 635                 640

Leu Glu Leu Tyr Ser Gln Lys Glu Leu Arg Ser Ser Asn Val Phe Asp
                645                 650                 655

Leu Glu Glu Ile Met Arg Glu Phe Asn Ser Tyr Lys Gln Arg Val Lys
            660                 665                 670

Tyr Val Glu Asp Lys Val Val Asp Pro Leu Pro Pro Tyr Leu Lys Gly
        675                 680                 685

Leu Asp Asp Leu Met Ser Gly Leu Gly Ala Ala Gly Lys Pro Pro Arg
690                 695                 700

Met Lys Gln Leu Glu Asp Lys Val Glu Glu Leu Leu Ser Lys Asn Tyr
705                 710                 715                 720

His Leu Glu Asn Glu Val Ala Arg Leu Lys Lys Leu Val Gly Glu Arg
                725                 730                 735

<210> SEQ ID NO 25
<211> LENGTH: 736
<212> TYPE: PRT
<213> ORGANISM: Artificial Sequence
<220> FEATURE:
<223> OTHER INFORMATION: a modified gB sequence

<400> SEQUENCE: 25
```

```
Val Ser Ser Ser Ser Thr Ser His Ala Thr Ser Ser Thr His Asn Gly
1               5                   10                  15

Ser His Thr Ser Arg Thr Thr Ser Ala Gln Thr Arg Ser Val Tyr Ser
                20                  25                  30

Gln His Val Thr Ser Ser Glu Ala Val Ser His Arg Ala Asn Glu Thr
            35                  40                  45

Ile Tyr Asn Thr Thr Leu Lys Tyr Gly Asp Val Val Gly Val Asn Thr
50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Ile Cys Thr Ser Met Lys Pro Ile Asn
                85                  90                  95

Glu Asp Leu Asp Glu Gly Ile Met Val Val Tyr Lys Arg Asn Ile Val
            100                 105                 110

Ala His Thr Phe Lys Val Arg Val Tyr Gln Lys Val Leu Thr Phe Arg
        115                 120                 125

Arg Ser Tyr Ala Gly His Arg Thr Thr Tyr Leu Leu Gly Ser Asn Thr
    130                 135                 140

Glu Tyr Val Ala Pro Pro Met Trp Glu Ile His His Ile Asn Lys Phe
145                 150                 155                 160

Ala Gln Cys Tyr Ser Ser Tyr Ser Arg Val Ile Gly Gly Thr Val Phe
                165                 170                 175

Val Ala Tyr His Arg Asp Ser Tyr Glu Asn Lys Thr Met Gln Leu Ile
            180                 185                 190

Pro Asp Asp Tyr Ser Asn Thr His Ser Thr Arg Tyr Val Thr Val Lys
        195                 200                 205

Asp Gln Trp His Ser Arg Gly Ser Thr Ala Phe His Arg Glu Thr Cys
    210                 215                 220

Asn Leu Asn Cys Met Leu Thr Ile Thr Thr Ala Arg Ser Lys Tyr Pro
225                 230                 235                 240

Tyr His Phe Phe Ala Thr Ser Thr Gly Asp Val Val Tyr Ile Ser Pro
                245                 250                 255

Phe Tyr Asn Gly Thr Asn Arg Asn Ala Ser Tyr Phe Gly Glu Asn Ala
            260                 265                 270

Asp Lys Phe Phe Ile Phe Pro Asn Tyr Thr Ile Val Ser Asp Phe Gly
        275                 280                 285

Arg Pro Asn Ala Ala Pro Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
            340                 345                 350

Phe Leu Ser Lys Lys Gln Glu Val Asn Met Ser Asp Ser Ala Leu Asp
        355                 360                 365

Cys Val Arg Asp Glu Ala Ile Asn Lys Leu Gln Gln Ile Phe Asn Thr
    370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
```

```
                420             425             430
His Thr Thr Gln Thr Ser Thr Ser Asp Asn Thr Thr His Leu Ser
                435             440             445

Ser Met Glu Ser Val His Asn Leu Val Tyr Ala Gln Leu Gln Phe Thr
    450             455             460

Tyr Asp Thr Leu Arg Gly Tyr Ile Asn Arg Ala Leu Ala Gln Ile Ala
465             470             475             480

Glu Ala Trp Pro Val Asp Gln Arg Arg Thr Leu Glu Val Phe Lys Glu
                485             490             495

Leu Ser Lys Ile Asn Pro Ser Ala Ile Leu Ser Ala Ile Tyr Asn Lys
            500             505             510

Pro Ile Ala Ala Arg Phe Met Gly Asp Val Leu Gly Leu Ala Ser Cys
            515             520             525

Val Thr Ile Asn Gln Thr Ser Val Lys Val Leu Arg Asp Met Asn Val
            530             535             540

Lys Glu Ser Pro Gly Arg Cys Tyr Ser Arg Pro Val Val Ile Phe Asn
545             550             555             560

Phe Ala Asn Ser Ser Tyr Val Gln Tyr Gly Gln Leu Gly Glu Asp Asn
                565             570             575

Glu Ile Leu Leu Gly Asn His Arg Thr Glu Glu Cys Gln Leu Pro Ser
            580             585             590

Leu Lys Ile Phe Ile Ala Gly Asn Ser Ala Tyr Glu Tyr Val Asp Tyr
            595             600             605

Leu Phe Lys Arg Met Ile Asp Leu Ser Ser Ile Ser Thr Val Asp Ser
            610             615             620

Met Ile Ala Leu Asp Ile Asp Pro Leu Glu Asn Thr Asp Phe Arg Val
625             630             635             640

Leu Glu Leu Tyr Ser Gln Lys Glu Leu Arg Ser Ser Asn Val Phe Asp
                645             650             655

Leu Glu Glu Ile Met Arg Glu Phe Asn Ser Tyr Lys Gln Arg Val Lys
                660             665             670

Tyr Val Glu Asp Lys Val Val Asp Pro Leu Pro Pro Tyr Leu Lys Gly
            675             680             685

Leu Asp Asp Leu Met Ser Gly Leu Gly Ala Ala Gly Lys Pro Pro Arg
            690             695             700

Met Lys Gln Leu Glu Asp Lys Val Glu Glu Leu Leu Ser Lys Asn Tyr
705             710             715             720

His Leu Glu Asn Glu Val Ala Arg Leu Lys Lys Leu Val Gly Glu Arg
                725             730             735

<210> SEQ ID NO 26
<211> LENGTH: 736
<212> TYPE: PRT
<213> ORGANISM: Artificial Sequence
<220> FEATURE:
<223> OTHER INFORMATION: a modified gB sequence

<400> SEQUENCE: 26

Val Ser Ser Ser Thr Ser His Ala Thr Ser Ser Thr His Asn Gly
1               5               10              15

Ser His Thr Ser Arg Thr Thr Ser Ala Gln Thr Arg Ser Val Tyr Ser
                20              25              30

Gln His Val Thr Ser Ser Glu Ala Val Ser His Arg Ala

```
                50                  55                  60
Thr Lys Tyr Pro Tyr Arg Val Cys Ser Met Ala Gln Gly Thr Asp Leu
 65                  70                  75                  80

Ile Arg Phe Glu Arg Asn Ile Ile Cys Thr Ser Met Lys Pro Ile Asn
                 85                  90                  95

Glu Asp Leu Asp Glu Gly Ile Met Val Val Tyr Lys Arg Asn Ile Val
                100                 105                 110

Ala His Thr Phe Lys Val Arg Val Tyr Gln Lys Val Leu Thr Phe Arg
                115                 120                 125

Arg Ser Tyr Ala Gly His Arg Thr Thr Tyr Leu Leu Gly Ser Asn Thr
                130                 135                 140

Glu Tyr Val Ala Pro Pro Met Trp Glu Ile His His Ile Asn Lys Phe
145                 150                 155                 160

Ala Gln Cys Tyr Ser Ser Tyr Ser Arg Val Ile Gly Gly Thr Val Phe
                165                 170                 175

Val Ala Tyr His Arg Asp Ser Tyr Glu Asn Lys Thr Met Gln Leu Ile
                180                 185                 190

Pro Asp Asp Tyr Ser Asn Thr His Ser Thr Arg Tyr Val Thr Val Lys
                195                 200                 205

Asp Gln Trp His Ser Arg Gly Ser Thr Ala Phe His Arg Glu Thr Cys
                210                 215                 220

Asn Leu Asn Cys Met Leu Thr Ile Thr Thr Ala Arg Ser Lys Tyr Pro
225                 230                 235                 240

Tyr His Phe Phe Ala Thr Ser Thr Gly Asp Val Val Tyr Ile Ser Pro
                245                 250                 255

Phe Tyr Asn Gly Thr Asn Arg Asn Ala Ser Tyr Phe Gly Glu Asn Ala
                260                 265                 270

Asp Lys Phe Phe Ile Phe Pro Asn Tyr Thr Ile Val Ser Asp Phe Gly
                275                 280                 285

Arg Pro Asn Ala Ala Pro Glu Thr His Arg Leu Val Ala Phe Leu Glu
                290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
                340                 345                 350

Phe Leu Ser Lys Lys Gln Glu Val Asn Met Ser Asp Ser Ala Leu Asp
                355                 360                 365

Cys Val Arg Asp Glu Ala Ile Asn Lys Leu Gln Gln Ile Phe Asn Thr
                370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
                420                 425                 430

His Thr Thr Gln Thr Ser Thr Ser Asp Asn Thr Thr His Leu Ser
                435                 440                 445

Ser Met Glu Ser Val His Asn Leu Val Tyr Ala Gln Leu Gln Phe Thr
450                 455                 460

Tyr Asp Thr Leu Arg Gly Tyr Ile Asn Arg Ala Leu Ala Gln Ile Ala
465                 470                 475                 480
```

```
Glu Ala Trp Cys Val Pro Gln Arg Arg Thr Leu Glu Val Phe Lys Glu
                485                 490                 495

Leu Ser Lys Ile Asn Pro Ser Ala Ile Leu Ser Ala Ile Tyr Asn Lys
            500                 505                 510

Pro Ile Ala Ala Arg Phe Met Gly Asp Val Leu Gly Leu Ala Ser Cys
        515                 520                 525

Val Thr Ile Asn Gln Thr Ser Val Lys Val Leu Arg Asp Met Asn Val
    530                 535                 540

Lys Glu Ser Pro Gly Arg Cys Tyr Ser Arg Pro Val Val Ile Phe Asn
545                 550                 555                 560

Phe Ala Asn Ser Ser Tyr Val Gln Tyr Gly Gln Leu Gly Glu Asp Asn
                565                 570                 575

Glu Ile Leu Leu Gly Asn His Arg Thr Glu Glu Cys Gln Leu Pro Ser
            580                 585                 590

Leu Lys Ile Phe Ile Ala Gly Asn Ser Ala Tyr Glu Tyr Val Asp Tyr
        595                 600                 605

Leu Phe Lys Arg Met Ile Asp Leu Ser Ser Ile Ser Thr Val Asp Ser
    610                 615                 620

Met Ile Ala Leu Asp Ile Asp Pro Leu Glu Asn Thr Asp Phe Arg Val
625                 630                 635                 640

Leu Glu Leu Tyr Ser Gln Lys Glu Leu Arg Ser Ser Asn Val Phe Asp
                645                 650                 655

Leu Glu Glu Ile Met Arg Glu Phe Asn Ser Tyr Lys Gln Arg Val Lys
            660                 665                 670

Tyr Val Glu Asp Lys Val Val Asp Pro Leu Pro Pro Tyr Leu Lys Gly
        675                 680                 685

Leu Asp Asp Leu Met Ser Gly Leu Gly Ala Ala Gly Lys Pro Pro Arg
    690                 695                 700

Met Lys Gln Leu Glu Asp Lys Val Glu Glu Leu Leu Ser Lys Asn Tyr
705                 710                 715                 720

His Leu Glu Asn Glu Val Ala Arg Leu Lys Lys Leu Val Gly Glu Arg
                725                 730                 735

<210> SEQ ID NO 27
<211> LENGTH: 736
<212> TYPE: PRT
<213> ORGANISM: Artificial Sequence
<220> FEATURE:
<223> OTHER INFORMATION: a modified gB sequence

<400> SEQUENCE: 27

Val Ser Ser Ser Thr Ser His Ala Thr Ser Ser Thr His Asn Gly
1               5                   10                  15

Ser His Thr Ser Arg Thr Thr Ser Ala Gln Thr Arg Ser Val Tyr Ser
                20                  25                  30

Gln

```
Ala His Thr Phe Lys Val Arg Val Tyr Gln Lys Val Leu Thr Phe Arg
    115                 120                 125

Arg Ser Tyr Ala Gly His Arg Thr Thr Tyr Leu Leu Gly Ser Asn Thr
130                 135                 140

Glu Tyr Val Ala Pro Pro Met Trp Glu Ile His His Ile Asn Lys Phe
145                 150                 155                 160

Ala Gln Cys Tyr Ser Ser Tyr Ser Arg Val Ile Gly Gly Thr Val Phe
                165                 170                 175

Val Ala Tyr His Arg Asp Ser Tyr Glu Asn Lys Thr Met Gln Leu Ile
                180                 185                 190

Pro Asp Asp Tyr Ser Asn Thr His Ser Thr Arg Tyr Val Thr Val Lys
                195                 200                 205

Asp Gln Trp His Ser Arg Gly Ser Thr Ala Phe His Arg Glu Thr Cys
    210                 215                 220

Asn Leu Asn Cys Met Leu Thr Ile Thr Thr Ala Arg Ser Lys Tyr Pro
225                 230                 235                 240

Tyr His Phe Phe Ala Thr Ser Thr Gly Asp Val Val Tyr Ile Ser Pro
                245                 250                 255

Phe Tyr Asn Gly Thr Asn Arg Asn Ala Ser Tyr Phe Gly Glu Asn Ala
                260                 265                 270

Asp Lys Phe Phe Ile Phe Pro Asn Tyr Thr Ile Val Ser Asp Phe Gly
    275                 280                 285

Arg Pro Asn Ala Ala Pro Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
                340                 345                 350

Phe Leu Ser Lys Lys Gln Glu Val Asn Met Ser Asp Ser Ala Leu Asp
    355                 360                 365

Cys Val Arg Asp Glu Ala Ile Asn Lys Leu Gln Gln Ile Phe Asn Thr
370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
                420                 425                 430

His Thr Thr Gln Thr Ser Thr Ser Asp Asn Asn Thr Thr His Leu Ser
    435                 440                 445

Ser Met Glu Ser Val His Asn Leu Val Tyr Ala Gln Leu Gln Phe Thr
    450                 455                 460

Tyr Asp Thr Leu Arg Gly Tyr Ile Asn Arg Ala Leu Ala Gln Ile Ala
465                 470                 475                 480

Glu Ala Trp Cys Val Asp Pro Arg Arg Thr Leu Glu Val Phe Lys Glu
                485                 490                 495

Leu Ser Lys Ile Asn Pro Ser Ala Ile Leu Ser Ala Ile Tyr Asn Lys
                500                 505                 510

Pro Ile Ala Ala Arg Phe Met Gly Asp Val Leu Gly Leu Ala Ser Cys
    515                 520                 525
```

```
Val Thr Ile Asn Gln Thr Ser Val Lys Val Leu Arg Asp Met Asn Val
            530                 535                 540

Lys Glu Ser Pro Gly Arg Cys Tyr Ser Arg Pro Val Val Ile Phe Asn
545                 550                 555                 560

Phe Ala Asn Ser Ser Tyr Val Gln Tyr Gly Gln Leu Gly Glu Asp Asn
                565                 570                 575

Glu Ile Leu Leu Gly Asn His Arg Thr Glu Glu Cys Gln Leu Pro Ser
            580                 585                 590

Leu Lys Ile Phe Ile Ala Gly Asn Ser Ala Tyr Glu Tyr Val Asp Tyr
            595                 600                 605

Leu Phe Lys Arg Met Ile Asp Leu Ser Ser Ile Ser Thr Val Asp Ser
            610                 615                 620

Met Ile Ala Leu Asp Ile Asp Pro Leu Glu Asn Thr Asp Phe Arg Val
625                 630                 635                 640

Leu Glu Leu Tyr Ser Gln Lys Glu Leu Arg Ser Ser Asn Val Phe Asp
                645                 650                 655

Leu Glu Glu Ile Met Arg Glu Phe Asn Ser Tyr Lys Gln Arg Val Lys
            660                 665                 670

Tyr Val Glu Asp Lys Val Val Asp Pro Leu Pro Pro Tyr Leu Lys Gly
            675                 680                 685

Leu Asp Asp Leu Met Ser Gly Leu Gly Ala Ala Gly Lys Pro Pro Arg
            690                 695                 700

Met Lys Gln Leu Glu Asp Lys Val Glu Leu Leu Ser Lys Asn Tyr
705                 710                 715                 720

His Leu Glu Asn Glu Val Ala Arg Leu Lys Lys Leu Val Gly Glu Arg
                725                 730                 735
```

<210> SEQ ID NO 28
<211> LENGTH: 736
<212> TYPE: PRT
<213> ORGANISM: Artificial Sequence
<220> FEATURE:
<223> OTHER INFORMATION: a modified gB sequence

<400> SEQUENCE: 28

```
Val Ser Ser Ser Ser Thr Ser His Ala Thr Ser Ser Thr His Asn Gly
1               5                   10                  15

```
Ala Gln Cys Tyr Ser Ser Tyr Ser Arg Val Ile Gly Gly Thr Val Phe
                165                 170                 175
Val Ala Tyr His Arg Asp Ser Tyr Glu Asn Lys Thr Met Gln Leu Ile
                180                 185                 190
Pro Asp Asp Tyr Ser Asn Thr His Ser Thr Arg Tyr Val Thr Val Lys
                195                 200                 205
Asp Gln Trp His Ser Arg Gly Ser Thr Ala Phe His Arg Glu Thr Cys
                210                 215                 220
Asn Leu Asn Cys Met Leu Thr Ile Thr Thr Ala Arg Ser Lys Tyr Pro
225                 230                 235                 240
Tyr His Phe Phe Ala Thr Ser Thr Gly Asp Val Val Tyr Ile Ser Pro
                245                 250                 255
Phe Tyr Asn Gly Thr Asn Arg Asn Ala Ser Tyr Phe Gly Glu Asn Ala
                260                 265                 270
Asp Lys Phe Phe Ile Phe Pro Asn Tyr Thr Ile Val Ser Asp Phe Gly
                275                 280                 285
Arg Pro Asn Ala Ala Pro Glu Thr His Arg Leu Val Ala Phe Leu Glu
                290                 295                 300
Arg Ala Asp Ser Val Ile Ser Trp Asp Ile Gln Asp Glu Lys Asn Val
305                 310                 315                 320
Thr Cys Gln Leu Thr Phe Trp Glu Ala Ser Glu Arg Thr Ile Arg Ser
                325                 330                 335
Glu Ala Glu Asp Ser Tyr His Phe Ser Ser Ala Lys Met Thr Ala Thr
                340                 345                 350
Phe Leu Ser Lys Lys Gln Glu Val Asn Met Ser Asp Ser Ala Leu Asp
                355                 360                 365
Cys Val Arg Asp Glu Ala Ile Asn Lys Leu Gln Gln Ile Phe Asn Thr
                370                 375                 380
Ser Tyr Asn Gln Thr Tyr Glu Lys Tyr Gly Asn Val Ser Val Phe Glu
385                 390                 395                 400
Thr Ser Gly Gly Leu Val Val Phe Trp Gln Gly Ile Lys Gln Lys Ser
                405                 410                 415
Leu Val Glu Leu Glu Arg Leu Ala Asn Arg Ser Ser Leu Asn Ile Thr
                420                 425                 430
His Thr Thr Gln Thr Ser Thr Ser Asp Asn Asn Thr Thr His Leu Ser
                435                 440                 445
Ser Met Glu Ser Val His Asn Leu Val Tyr Ala Gln Leu Gln Phe Thr
450                 455                 460
Tyr Asp Thr Leu Arg Gly Tyr Ile Asn Arg Ala Leu Ala Gln Ile Ala
465                 470                 475                 480
Glu Ala Trp Cys Val Asp Gln Pro Arg Thr Leu Glu Val Phe Lys Glu
                485                 490                 495
Leu Ser Lys Ile Asn Pro Ser Ala Ile Leu Ser Ala Ile Tyr Asn Lys
                500                 505                 510
Pro Ile Ala Ala Arg Phe Met Gly Asp Val Leu Gly Leu Ala Ser Cys
                515                 520                 525
Val Thr Ile Asn Gln Thr Ser Val Lys Val Leu Arg Asp Met Asn Val
                530                 535                 540
Lys Glu Ser Pro Gly Arg Cys Tyr Ser Arg Pro Val Val Ile Phe Asn
545                 550                 555                 560
Phe Ala Asn Ser Ser Tyr Val Gln Tyr Gly Gln Leu Gly Glu Asp Asn
                565                 570                 575
Glu Ile Leu Leu Gly Asn His Arg Thr Glu Glu Cys Gln Leu Pro Ser
```

```
                580             585             590
Leu Lys Ile Phe Ile Ala Gly Asn Ser Ala Tyr Glu Tyr Val Asp Tyr
            595                 600                 605
Leu Phe Lys Arg Met Ile Asp Leu Ser Ser Ile Ser Thr Val Asp Ser
            610                 615                 620
Met Ile Ala Leu Asp Ile Asp Pro Leu Glu Asn Thr Asp Phe Arg Val
625                 630                 635                 640
Leu Glu Leu Tyr Ser Gln Lys Glu Leu Arg Ser Ser Asn Val Phe Asp
                645                 650                 655
Leu Glu Glu Ile Met Arg Glu Phe Asn Ser Tyr Lys Gln Arg Val Lys
                660                 665                 670
Tyr Val Glu Asp Lys Val Val Asp Pro Leu Pro Pro Tyr Leu Lys Gly
                675                 680                 685
Leu Asp Asp Leu Met Ser Gly Leu Gly Ala Ala Gly Lys Pro Pro Arg
                690                 695                 700
Met Lys Gln Leu Glu Asp Lys Val Glu Glu Leu Leu Ser Lys Asn Tyr
705                 710                 715                 720
His Leu Glu Asn Glu Val Ala Arg Leu Lys Lys Leu Val Gly Glu Arg
                    725                 730                 735

<210> SEQ ID NO 29
<211> LENGTH: 736
<212> TYPE: PRT
<213> ORGANISM: Artificial Sequence
<220> FEATURE:
<223> OTHER INFORMATION: a modified gB sequence

<400> SEQUENCE: 29

Val Ser Ser Ser Thr Ser His Ala Thr Ser Ser Thr His Asn Gly
1               5                   10                  15
Ser His Thr Ser Arg Thr Thr Ser Ala Gln Thr Arg Ser Val Tyr Ser
                20                  25                  30
Gln His Val Thr Ser Ser Glu Ala Val Ser His Arg Ala Asn Glu Thr
            35                  40                  45
Ile Tyr Asn Thr Thr Leu Lys Tyr Gly Asp Val Val Gly Val Asn Thr
50                  55                  60
Thr Lys Tyr Pro Tyr Arg Val Cys Ser Met Ala Gln Gly Thr Asp Leu
65                  70                  75                  80
Ile Arg Phe Glu Arg Asn Ile Ile Cys Thr Ser Met Lys Pro Ile Asn
                85                  90                  95
Glu Asp Leu Asp Glu Gly Ile Met Val Val Tyr Lys Arg Asn Ile Val
            100                 105                 110
Ala His Thr Phe Lys Val Arg Val Tyr Gln Lys Val Leu Thr Phe Arg
            115                 120                 125
Arg Ser Tyr Ala Gly His Arg Thr Thr Tyr Leu Leu Gly Ser Asn Thr
        130                 135                 140
Glu Tyr Val Ala Pro Pro Met Trp Glu Ile His His Ile Asn Lys Phe
145                 150                 155                 160
Ala Gln Cys Tyr Ser Ser Tyr Ser Arg Val Ile Gly Gly Thr Val Phe
                165                 170                 175
Val Ala Tyr His Arg Asp Ser Tyr Glu Asn Lys Thr Met Gln Leu Ile
            180                 185                 190
Pro Asp Asp Tyr Ser Asn Thr His Ser Thr Arg Tyr Val Thr Val Lys
            195                 200                 205
Asp Gln Trp His Ser Arg Gly Ser Thr Ala Phe His Arg Glu Thr Cys
```

```
              210                 215                 220
Asn Leu Asn Cys Met Leu Thr Ile Thr Thr Ala Arg Ser Lys Tyr Pro
225                 230                 235                 240

Tyr His Phe Phe Ala Thr Ser Thr Gly Asp Val Val Tyr Ile Ser Pro
                245                 250                 255

Phe Tyr Asn Gly Thr Asn Arg Asn Ala Ser Tyr Phe Gly Glu Asn Ala
                260                 265                 270

Asp Lys Phe Phe Ile Phe Pro Asn Tyr Thr Ile Val Ser Asp Phe Gly
                275                 280                 285

Arg Pro Asn Ala Ala Pro Glu Thr His Arg Leu Val Ala Phe Leu Glu
        290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
                340                 345                 350

Phe Leu Ser Lys Lys Gln Glu Val Asn Met Ser Asp Ser Ala Leu Asp
            355                 360                 365

Cys Val Arg Asp Glu Ala Ile Asn Lys Leu Gln Gln Ile Phe Asn Thr
            370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
                420                 425                 430

His Thr Thr Gln Thr Ser Thr Ser Asp Asn Asn Thr Thr His Leu Ser
            435                 440                 445

Ser Met Glu Ser Val His Asn Leu Val Tyr Ala Gln Leu Gln Phe Thr
        450                 455                 460

Tyr Asp Thr Leu Arg Gly Tyr Ile Asn Arg Ala Leu Ala Gln Ile Ala
465                 470                 475                 480

Glu Ala Pro Cys Val Asp Pro Arg Arg Thr Leu Glu Val Phe Lys Glu
                485                 490                 495

Leu Ser Lys Ile Asn Pro Ser Ala Ile Leu Ser Ala Ile Tyr Asn Lys
            500                 505                 510

Pro Ile Ala Ala Arg Phe Met Gly Asp Val Leu Gly Leu Ala Ser Cys
            515                 520                 525

Val Thr Ile Asn Gln Thr Ser Val Lys Val Leu Arg Asp Met Asn Val
        530                 535                 540

Lys Glu Ser Pro Gly Arg Cys Tyr Ser Arg Pro Val Val Ile Phe Asn
545                 550                 555                 560

Phe Ala Asn Ser Ser Tyr Val Gln Tyr Gly Gln Leu Gly Glu Asp Asn
                565                 570                 575

Glu Ile Leu Leu Gly Asn His Arg Thr Glu Glu Cys Gln Leu Pro Ser
            580                 585                 590

Leu Lys Ile Phe Ile Ala Gly Asn Ser Ala Tyr Glu Tyr Val Asp Tyr
            595                 600                 605

Leu Phe Lys Arg Met Ile Asp Leu Ser Ser Ile Ser Thr Val Asp Ser
        610                 615                 620

Met Ile Ala Leu Asp Ile Asp Pro Leu Glu Asn Thr Asp Phe Arg Val
625                 630                 635                 640
```

```
Leu Glu Leu Tyr Ser Gln Lys Glu Leu Arg Ser Ser Asn Val Phe Asp
            645                 650                 655

Leu Glu Glu Ile Met Arg Glu Phe Asn Ser Tyr Lys Gln Arg Val Lys
            660                 665                 670

Tyr Val Glu Asp Lys Val Val Asp Pro Leu Pro Pro Tyr Leu Lys Gly
            675                 680                 685

Leu Asp Asp Leu Met Ser Gly Leu Gly Ala Ala Gly Lys Pro Pro Arg
            690                 695                 700

Met Lys Gln Leu Glu Asp Lys Val Glu Glu Leu Leu Ser Lys Asn Tyr
705                 710                 715                 720

His Leu Glu Asn Glu Val Ala Arg Leu Lys Lys Leu Val Gly Glu Arg
            725                 730                 735
```

<210> SEQ ID NO 30
<211> LENGTH: 736
<212> TYPE: PRT
<213> ORGANISM: Artificial Sequence
<220> FEATURE:
<223> OTHER INFORMATION: a modified gB sequence

<400> SEQUENCE: 30

```
Val

```
Asp Lys Phe Phe Ile Phe Pro Asn Tyr Thr Ile Val Ser Asp Phe Gly
        275                 280                 285

Arg Pro Asn Ala Ala Pro Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

Glu Ala Glu Asp Ser Tyr His Phe Ser Ser Ala Lys Met Thr Ala Thr
            340                 345                 350

Phe Leu Ser Lys Lys Gln Glu Val Asn Met Ser Asp Ser Ala Leu Asp
        355                 360                 365

Cys Val Arg Asp Glu Ala Ile Asn Lys Leu Gln Gln Ile Phe Asn Thr
    370                 375                 380

Ser Tyr Asn Gln Thr Tyr Glu Lys Tyr Gly Asn Val Ser Val Phe Glu
385                 390                 395                 400

Thr Ser Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Ile Thr
            420                 425                 430

His Thr Thr Gln Thr Ser Thr Ser Asp Asn Asn Thr Thr His Leu Ser
        435                 440                 445

Ser Met Glu Ser Val His Asn Leu Val Tyr Ala Gln Leu Gln Phe Thr
    450                 455                 460

Tyr Asp Thr Leu Arg Gly Tyr Ile Asn Arg Ala Leu Ala Gln Ile Ala
465                 470                 475                 480

Glu Ala Trp Cys Val Pro Pro Arg Arg Thr Leu Glu Val Phe Lys Glu
                485                 490                 495

Leu Ser Lys Ile Asn Pro Ser Ala Ile Leu Ser Ala Ile Tyr Asn Lys
            500                 505                 510

Pro Ile Ala Ala Arg Phe Met Gly Asp Val Leu Gly Leu Ala Ser Cys
        515                 520                 525

Val Thr Ile Asn Gln Thr Ser Val Lys Val Leu Arg Asp Met Asn Val
    530                 535                 540

Lys Glu Ser Pro Gly Arg Cys Tyr Ser Arg Pro Val Val Ile Phe Asn
545                 550                 555                 560

Phe Ala Asn Ser Ser Tyr Val Gln Tyr Gly Gln Leu Gly Glu Asp Asn
                565                 570                 575

Glu Ile Leu Leu Gly Asn His Arg Thr Glu Glu Cys Gln Leu Pro Ser
            580                 585                 590

Leu Lys Ile Phe Ile Ala Gly Asn Ser Ala Tyr Glu Tyr Val Asp Tyr
        595                 600                 605

Leu Phe Lys Arg Met Ile Asp Leu Ser Ser Ile Ser Thr Val Asp Ser
    610                 615                 620

Met Ile Ala Leu Asp Ile Asp Pro Leu Glu Asn Thr Asp Phe Arg Val
625                 630                 635                 640

Leu Glu Leu Tyr Ser Gln Lys Glu Leu Arg Ser Ser Asn Val Phe Asp
                645                 650                 655

Leu Glu Glu Ile Met Arg Glu Phe Asn Ser Tyr Lys Gln Arg Val Lys
            660                 665                 670

Tyr Val Glu Asp Lys Val Val Asp Pro Leu Pro Pro Tyr Leu Lys Gly
        675                 680                 685
```

-continued

```
Leu Asp Asp Leu Met Ser Gly Leu Gly Ala Ala Gly Lys Pro Pro Arg
    690             695             700

Met Lys Gln Leu Glu Asp Lys Val Glu Glu Leu Leu Ser Lys Asn Tyr
705             710             715             720

His Leu Glu Asn Glu Val Ala Arg Leu Lys Lys Leu Val Gly Glu Arg
                725             730             735
```